United States Patent
Bays et al.

(10) Patent No.: US 11,278,337 B2
(45) Date of Patent: *Mar. 22, 2022

(54) TARSAL-METATARSAL JOINT PROCEDURE UTILIZING FULCRUM

(71) Applicant: Treace Medical Concepts, Inc., Ponte Vedra, FL (US)

(72) Inventors: F. Barry Bays, Collierville, TN (US); Robert D. Santrock, Morgantown, WV (US); Paul Dayton, Fort Dodge, IA (US); Daniel J. Hatch, Greeley, CO (US); W. Bret Smith, Lexington, SC (US); Carlos Eduardo Gil, Jacksonville Beach, FL (US); Sean F. Scanlan, Jacksonville, FL (US); Joe William Ferguson, Ponte Vedra Beach, FL (US); John T. Treace, Ponte Vedra Beach, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 295 days.

This patent is subject to a terminal disclaimer.

(21) Appl. No.: 16/505,363

(22) Filed: Jul. 8, 2019

(65) Prior Publication Data

US 2019/0328436 A1 Oct. 31, 2019

Related U.S. Application Data

(63) Continuation of application No. 15/236,464, filed on Aug. 14, 2016, now Pat. No. 10,342,590, which is a (Continued)

(51) Int. Cl.
*A61B 17/88* (2006.01)
*A61B 17/80* (2006.01)
(Continued)

(52) U.S. Cl.
CPC ........ *A61B 17/8866* (2013.01); *A61B 17/151* (2013.01); *A61B 17/8061* (2013.01); *A61B 2017/564* (2013.01)

(58) Field of Classification Search
CPC . A61B 17/88; A61B 17/8888; A61B 17/8866; A61B 17/80; A61B 17/8061; A61B 17/02; A61B 17/025
See application file for complete search history.

(56) References Cited

U.S. PATENT DOCUMENTS

| | | | |
|---|---|---|---|
| 3,664,022 | A | 5/1972 | Small |
| 4,069,824 | A | 1/1978 | Weinstock |

(Continued)

FOREIGN PATENT DOCUMENTS

| | | |
|---|---|---|
| AU | 2009227957 B2 | 7/2014 |
| CA | 2491824 A1 | 9/2005 |

(Continued)

OTHER PUBLICATIONS

Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.

(Continued)

*Primary Examiner* — Christopher J Beccia
(74) *Attorney, Agent, or Firm* — Fredrikson & Byron, P.A.

(57) ABSTRACT

A technique for correcting a bone deformity, such as a bunion, may be performed using a fulcrum. In some examples, the technique involves inserting a fulcrum between a first metatarsal that is anatomically misaligned with respect to a second metatarsal. The technique further includes preparing an end of the first metatarsal and preparing an end of a medial cuneiform opposing the end of the (Continued)

first metatarsal. In addition, a distal portion of the first metatarsal is moved toward the second metatarsal in a transverse plane, thereby pivoting a proximal portion of the first metatarsal about the fulcrum and reducing an intermetatarsal angle between the first metatarsal and the second metatarsal.

20 Claims, 49 Drawing Sheets

Related U.S. Application Data continuation-in-part of application No. 14/981,335, filed on Dec. 28, 2015, now Pat. No. 9,622,805.

(60) Provisional application No. 62/293,189, filed on Feb. 9, 2016, provisional application No. 62/205,338, filed on Aug. 14, 2015.

(51) Int. Cl.
*A61B 17/15* (2006.01)
*A61B 17/56* (2006.01)

(56) References Cited

U.S. PATENT DOCUMENTS

| | | | |
|---|---|---|---|
| 4,159,716 A | 7/1979 | Borchers |
| 4,187,840 A | 2/1980 | Watanabe |
| 4,335,715 A | 6/1982 | Kirkley |
| 4,338,927 A | 7/1982 | Volkov et al. |
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,570,624 A | 2/1986 | Wu |
| 4,627,425 A | 12/1986 | Reese |
| 4,628,919 A | 12/1986 | Clyburn |
| 4,632,102 A | 12/1986 | Comparetto |
| 4,664,102 A | 5/1987 | Comparetto |
| 4,708,133 A | 11/1987 | Comparetto |
| 4,736,737 A | 4/1988 | Fargie et al. |
| 4,750,481 A | 6/1988 | Reese |
| 4,757,810 A | 7/1988 | Reese |
| 4,895,141 A | 1/1990 | Koeneman et al. |
| 4,952,214 A | 8/1990 | Comparetto |
| 4,959,066 A | 9/1990 | Dunn et al. |
| 4,978,347 A | 12/1990 | Ilizarov |
| 4,988,349 A | 1/1991 | Pennig |
| 4,995,875 A | 2/1991 | Coes |
| 5,021,056 A | 6/1991 | Hofmann et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,207,676 A | 5/1993 | Canadell et al. |
| 5,246,444 A | 9/1993 | Schreiber |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,374,271 A | 12/1994 | Hwang |
| 5,413,579 A | 5/1995 | Tom Du Toit |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A * | 6/1996 | Clark | A61B 17/683 |
| | | | 128/898 |
| 5,540,695 A | 7/1996 | Levy |
| 5,578,038 A | 11/1996 | Slocum |
| 5,601,565 A | 2/1997 | Huebner |
| 5,613,969 A | 3/1997 | Jenkins, Jr. |
| 5,620,442 A | 4/1997 | Bailey et al. |
| 5,620,448 A | 4/1997 | Puddu |
| 5,643,270 A | 7/1997 | Combs |
| 5,667,510 A | 9/1997 | Combs |
| H1706 H | 1/1998 | Mason |
| 5,722,978 A | 3/1998 | Jenkins |
| 5,749,875 A | 5/1998 | Puddu |
| 5,779,709 A | 7/1998 | Harris et al. |
| 5,788,695 A | 8/1998 | Richardson |
| 5,803,924 A | 9/1998 | Oni et al. |
| 5,810,822 A | 9/1998 | Mortier |
| 5,843,085 A | 12/1998 | Graser |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,980,526 A | 11/1999 | Johnson et al. |
| 5,984,931 A | 11/1999 | Greenfield |
| 6,007,535 A | 12/1999 | Rayhack et al. |
| 6,027,504 A | 2/2000 | McGuire |
| 6,030,391 A | 2/2000 | Brainard et al. |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,416,465 B2 | 7/2002 | Brau |
| 6,478,799 B1 | 11/2002 | Williamson |
| 6,511,481 B2 | 1/2003 | Von Hoffmann et al. |
| 6,547,793 B1 | 4/2003 | McGuire |
| 6,676,662 B1 | 1/2004 | Bagga et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,796,986 B2 | 9/2004 | Duffner |
| 6,859,661 B2 | 2/2005 | Tuke |
| 6,964,645 B1 * | 11/2005 | Smits | A61F 5/019 |
| | | | 602/30 |
| 7,018,383 B2 | 3/2006 | McGuire |
| 7,033,361 B2 | 4/2006 | Collazo |
| 7,112,204 B2 | 9/2006 | Justin et al. |
| 7,182,766 B1 | 2/2007 | Mogul |
| 7,241,298 B2 | 7/2007 | Nemec et al. |
| 7,282,054 B2 | 10/2007 | Steffensmeier et al. |
| 7,377,924 B2 | 5/2008 | Raistrick et al. |
| 7,465,303 B2 | 12/2008 | Riccione et al. |
| 7,540,874 B2 | 6/2009 | Trumble et al. |
| 7,572,258 B2 | 8/2009 | Stiernborg |
| 7,641,660 B2 | 1/2010 | Lakin et al. |
| D610,257 S | 2/2010 | Horton |
| 7,686,811 B2 | 3/2010 | Byrd et al. |
| 7,691,108 B2 | 4/2010 | Lavallee |
| 7,763,026 B2 | 7/2010 | Egger et al. |
| D629,900 S | 12/2010 | Fisher |
| 7,875,058 B2 * | 1/2011 | Holmes, Jr. | A61B 17/842 |
| | | | 606/232 |
| 7,967,823 B2 | 6/2011 | Ammann et al. |
| 7,972,338 B2 | 7/2011 | O'Brien |
| D646,389 S | 10/2011 | Claypool et al. |
| 8,057,478 B2 | 11/2011 | Kuczynski et al. |
| 8,062,301 B2 | 11/2011 | Ammann et al. |
| D651,315 S | 12/2011 | Bertoni et al. |
| D651,316 S | 12/2011 | May et al. |
| 8,080,010 B2 | 12/2011 | Schulz et al. |
| 8,080,045 B2 | 12/2011 | Wotton, III |
| 8,083,746 B2 | 12/2011 | Novak |
| 8,123,753 B2 | 2/2012 | Poncet |
| 8,137,406 B2 | 3/2012 | Novak et al. |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,192,441 B2 | 6/2012 | Collazo |

(56) References Cited

U.S. PATENT DOCUMENTS

| | | |
|---|---|---|
| 8,197,487 B2 | 6/2012 | Poncet et al. |
| 8,231,623 B1 | 7/2012 | Jordan |
| 8,231,663 B2 | 7/2012 | Kay et al. |
| 8,236,000 B2 | 8/2012 | Ammann et al. |
| 8,246,561 B1 | 8/2012 | Agee et al. |
| D666,721 S | 9/2012 | Wright et al. |
| 8,262,664 B2 | 9/2012 | Justin et al. |
| 8,277,459 B2 | 10/2012 | Sand et al. |
| 8,282,644 B2 | 10/2012 | Edwards |
| 8,282,645 B2 | 10/2012 | Lawrence et al. |
| 8,292,966 B2 | 10/2012 | Morton |
| 8,303,596 B2 | 11/2012 | Plassky et al. |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Bscher |
| D679,395 S | 4/2013 | Wright et al. |
| 8,409,209 B2 | 4/2013 | Ammann et al. |
| 8,435,246 B2 | 5/2013 | Fisher et al. |
| 8,475,462 B2 | 7/2013 | Thomas et al. |
| 8,496,662 B2 | 7/2013 | Novak et al. |
| 8,523,870 B2 | 9/2013 | Green, II et al. |
| 8,529,571 B2 | 9/2013 | Horan et al. |
| 8,540,777 B2 | 9/2013 | Ammann et al. |
| 8,545,508 B2 | 10/2013 | Collazo |
| D694,884 S | 12/2013 | Mooradian et al. |
| D695,402 S | 12/2013 | Dacosta et al. |
| 8,652,142 B2 | 2/2014 | Geissler |
| 8,657,820 B2 | 2/2014 | Kubiak et al. |
| D701,303 S | 3/2014 | Cook |
| 8,672,945 B2 | 3/2014 | Lavallee et al. |
| 8,696,716 B2 | 4/2014 | Kartalian et al. |
| 8,702,715 B2 | 4/2014 | Ammann et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,760 B2 | 7/2014 | Metzger et al. |
| 8,764,763 B2 | 7/2014 | Wong et al. |
| 8,771,279 B2 | 7/2014 | Philippon et al. |
| 8,777,948 B2 | 7/2014 | Bernsteiner |
| 8,784,427 B2 | 7/2014 | Fallin et al. |
| 8,784,457 B2 | 7/2014 | Graham |
| 8,795,286 B2 | 8/2014 | Sand et al. |
| 8,801,727 B2 | 8/2014 | Chan et al. |
| 8,808,303 B2 | 8/2014 | Stemniski et al. |
| 8,828,012 B2 | 9/2014 | May et al. |
| 8,858,602 B2 | 10/2014 | Weiner et al. |
| 8,882,778 B2 | 11/2014 | Ranft |
| 8,882,816 B2 | 11/2014 | Kartalian et al. |
| 8,888,785 B2 | 11/2014 | Ammann et al. |
| D720,456 S | 12/2014 | Dacosta et al. |
| 8,900,247 B2 | 12/2014 | Tseng et al. |
| 8,906,026 B2 | 12/2014 | Ammann et al. |
| 8,945,132 B2 | 2/2015 | Plassy et al. |
| 8,998,903 B2 | 4/2015 | Price et al. |
| 8,998,904 B2 | 4/2015 | Zeetser et al. |
| 9,023,052 B2 | 5/2015 | Lietz et al. |
| 9,044,250 B2 | 6/2015 | Olsen et al. |
| 9,060,822 B2 * | 6/2015 | Lewis ................ A61B 17/8061 |
| 9,089,376 B2 | 7/2015 | Medoff et al. |
| 9,101,421 B2 | 8/2015 | Blacklidge |
| 9,107,715 B2 | 8/2015 | Blitz et al. |
| 9,113,920 B2 | 8/2015 | Ammann et al. |
| D740,424 S | 10/2015 | Dacosta et al. |
| D765,844 S | 9/2016 | DaCosta |
| D766,434 S | 9/2016 | DaCosta |
| D766,437 S | 9/2016 | DaCosta |
| D766,438 S | 9/2016 | DaCosta |
| D766,439 S | 9/2016 | DaCosta |
| 9,522,023 B2 | 12/2016 | Haddad et al. |
| 9,750,538 B2 | 9/2017 | Soffiatti et al. |
| 9,785,747 B2 | 10/2017 | Geebelen |
| 10,028,750 B2 | 7/2018 | Rose |
| 10,064,631 B2 | 9/2018 | Dacosta et al. |
| 10,159,499 B2 | 12/2018 | Dacosta et al. |
| 10,292,713 B2 | 5/2019 | Fallin et al. |
| 10,327,829 B2 | 6/2019 | Dacosta et al. |
| 10,342,590 B2 * | 7/2019 | Bays ..................... A61B 17/15 |
| 10,470,779 B2 | 11/2019 | Fallin et al. |
| 10,779,867 B2 | 9/2020 | Penzimer et al. |
| 2002/0099381 A1 | 7/2002 | Maroney |
| 2002/0107519 A1 | 8/2002 | Dixon et al. |
| 2002/0165552 A1 | 11/2002 | Duffner |
| 2002/0198531 A1 | 12/2002 | Millard et al. |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2004/0138669 A1 | 7/2004 | Horn |
| 2005/0004676 A1 | 1/2005 | Schon et al. |
| 2005/0059978 A1 | 3/2005 | Sherry et al. |
| 2005/0070909 A1 | 3/2005 | Egger et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0228389 A1 | 10/2005 | Stiernborg |
| 2005/0251147 A1 | 11/2005 | Novak |
| 2005/0273112 A1 | 12/2005 | McNamara |
| 2006/0129163 A1 | 6/2006 | McGuire |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0010818 A1 | 1/2007 | Stone et al. |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0015603 A1 | 1/2008 | Collazo |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0147073 A1 | 6/2008 | Ammann et al. |
| 2008/0172054 A1 | 7/2008 | Claypool et al. |
| 2008/0195215 A1 | 8/2008 | Morton |
| 2008/0208252 A1 | 8/2008 | Holmes |
| 2008/0262500 A1 | 10/2008 | Collazo |
| 2008/0269908 A1 | 10/2008 | Warburton |
| 2008/0288004 A1 | 11/2008 | Schendel |
| 2009/0036893 A1 * | 2/2009 | Kartalian ........... A61B 17/1775 |
| | | 606/60 |
| 2009/0036931 A1 | 2/2009 | Pech et al. |
| 2009/0054899 A1 | 2/2009 | Ammann et al. |
| 2009/0093849 A1 | 4/2009 | Grabowski |
| 2009/0105767 A1 | 4/2009 | Reiley |
| 2009/0118733 A1 | 5/2009 | Orsak et al. |
| 2009/0198244 A1 | 8/2009 | Leibel |
| 2009/0198279 A1 | 8/2009 | Zhang et al. |
| 2009/0216089 A1 | 8/2009 | Davidson |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0287309 A1 | 11/2009 | Walch et al. |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0249779 A1 | 9/2010 | Hotchkiss et al. |
| 2010/0256687 A1 | 10/2010 | Neufeld et al. |
| 2010/0318088 A1 | 12/2010 | Warne et al. |
| 2010/0324556 A1 | 12/2010 | Tyber et al. |
| 2011/0009865 A1 | 1/2011 | Orfaly |
| 2011/0077656 A1 * | 3/2011 | Sand .................. A61B 17/8861 |
| | | 606/96 |
| 2011/0093084 A1 | 4/2011 | Morton |
| 2011/0118739 A1 | 5/2011 | Tyber et al. |
| 2011/0178524 A1 | 7/2011 | Lawrence et al. |
| 2011/0245835 A1 | 10/2011 | Dodds et al. |

(56) References Cited

U.S. PATENT DOCUMENTS

| | | |
|---|---|---|
| 2011/0288550 A1 | 11/2011 | Orbay et al. |
| 2011/0301648 A1* | 12/2011 | Lofthouse ......... A61B 17/0401 606/300 |
| 2012/0016426 A1* | 1/2012 | Robinson ............. A61B 17/864 606/328 |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130382 A1 | 5/2012 | Iannotti et al. |
| 2012/0130383 A1 | 5/2012 | Budoff |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee et al. |
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0085502 A1 | 4/2013 | Harrold |
| 2013/0096563 A1 | 4/2013 | Meade et al. |
| 2013/0131821 A1 | 5/2013 | Cachia |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Lewis et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Hatch et al. |
| 2013/0226252 A1 | 8/2013 | Mayer |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0135775 A1 | 5/2014 | Maxson et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0188139 A1 | 7/2014 | Fallin et al. |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0249537 A1 | 9/2014 | Wong et al. |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0288562 A1 | 9/2014 | Von Zabern et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |
| 2015/0032168 A1 | 1/2015 | Orsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2016/0015426 A1 | 1/2016 | Dayton et al. |
| 2016/0022315 A1 | 1/2016 | Soffiatti et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |
| 2016/0324532 A1 | 11/2016 | Montoya et al. |
| 2016/0354127 A1 | 12/2016 | Lundquist et al. |
| 2017/0042598 A1 | 2/2017 | Santrock et al. |
| 2017/0079669 A1 | 3/2017 | Bays et al. |
| 2017/0143511 A1 | 5/2017 | Cachia |
| 2017/0164989 A1 | 6/2017 | Weiner et al. |
| 2018/0344334 A1 | 12/2018 | Kim et al. |

FOREIGN PATENT DOCUMENTS

| | | |
|---|---|---|
| CA | 2854997 A1 | 5/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| DE | 202006010241 U1 | 3/2007 |
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 2624764 B1 | 12/2015 |
| FR | 2362616 A1 | 3/1978 |
| FR | 2764183 B1 | 11/1999 |
| FR | 2953120 B1 | 1/2012 |
| FR | 3030221 A1 | 6/2016 |
| GB | 2154143 A | 9/1985 |
| GB | 2154144 A | 9/1985 |
| GB | 2334214 B | 1/2003 |
| IN | 200903719 P1 | 6/2009 |
| IN | 200904479 P2 | 5/2010 |

(56) References Cited

FOREIGN PATENT DOCUMENTS

| | | |
|---|---|---|
| IN | 140/DELNP/2012 P1 | 2/2013 |
| IN | 2004/KOLNP/2013 P2 | 11/2013 |
| JP | 2006158972 A | 6/2006 |
| JP | 4134243 B2 | 8/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 03075775 A1 | 9/2003 |
| WO | 2004089227 A2 | 10/2004 |
| WO | 2008051064 A1 | 5/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015094409 A1 | 6/2015 |
| WO | 2015105880 A1 | 7/2015 |
| WO | 2015127515 A2 | 9/2015 |
| WO | 2016134160 A1 | 8/2016 |

OTHER PUBLICATIONS

Anderson et al., "Uncemented STAR Total Ankle Prostheses," The Journal of Bone and Joint Surgery, vol. 86(1, Suppl 2), Sep. 2004, pp. 103-111, (Abstract Only).

Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.

Dayton et al., "Relationship Of Frontal Plane Rotation Of First Metatarsal To Proximal Articular Set Angle And Hallux Alignment In Patients Undergoing Tarsometatarsal Arthrodesis For Hallux Abducto Valgus: A Case Series And Critical Review Of The Literature," The Journal of Foot and Ankle Surgery, vol. 52, No. 3, May/Jun. 2013, pp. 348-354.

Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.

De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.

DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.

Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).

EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.

Garthwait, "Accu-Cut System Facilitates Enhanced Precision," Podiatry Today, vol. 18, No. 6, Jun. 2005, 6 pages.

Gonzalez Del Pino et al., "Variable Angle Locking Intercarpal Fusion System for Four-Corner Arthrodesis Indications and Surgical Technique," Journal of Wrist Surgery, vol. 1, No. 1, Aug. 2012, pp. 73-78.

Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).

"HAT-TRICK Lesser Toe Repair System," Smith & Nephew, Brochure, Aug. 2014, 12 pages.

"Hoffmann II Compact External Fixation System," Stryker, Brochure, Literature No. 5075-1-500, 2006, 12 pages.

"Hoffmann II Micro Lengthener," Stryker, Operative Technique, Literature No. 5075-2-002, 2008, 12 pages.

"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.

Kim et al., "A New Measure of Tibial Sesamoid Position in Hallux Valgus in Relation to the Coronal Rotation of the Firsl Metatarsal in CT Scans," Foot and Ankle International, vol. 36, No. 8, 2015, pp. 944-952.

"Lag Screw Target Bow," Stryker Leibinger GmbH & Co. KG, Germany 2004, 8 pages.

MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.

Michelangelo Bunion System, Surgical Technique, Instratek Incorporated, publication date unknown, 4 pages.

Mini Joint Distractor, Arthrex, retrieved Dec. 19, 2014, from the Internet: <http://www.arthrex.com/foot-ankle/mini-joint-distractor/products>, 2 pages.

MiniRail System, Small Bone Innovations, Surgical Technique, 2010, 24 pages.

Modular Rail System: External Fixator, Smith & Nephew, Surgical Technique, 2013, 44 pages.

Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).

Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).

Mortier et al., "Axial Rotation of the First Metatarsal Head in a Normal Population and Hallux Valgus Patients," Orthopaedics and Traumatology: Surgery and Research, vol. 98, 2012, pp. 677-683.

Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.

Rx-Fix Mini Rail External Fixator, Wright Medical Technology, Brochure, Aug. 15, 2014, 2 pages.

Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).

(56) References Cited

OTHER PUBLICATIONS

Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.
Siddiqui et al. "Fixation Of Metatarsal Fracture With Bone Plate In A Dromedary Heifer," Open Veterinary Journal, vol. 3, No. 1, 2013, pp. 17-20.
Sidekick Siealth Rearfoot Fixator, Wright Medical Technology, Surgical Technique, Dec. 2, 2013, 20 pages.
Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
Stableloc External Fixation System, Acumed, Product Overview, Effective date Sep. 2015, 4 pages.
Stahl et al., "Derotation Of Post-Traumatic Femoral Deformities By Closed Intramedullary Sawing," Injury, vol. 37, No. 2, Feb. 2006, pp. 145-151, (Abstract Only).
Talbot et al.,"Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Weber et al., "A Simple System For Navigation Of Bone Alignment Osteotomies Of The Tibia," International Congress Series, vol. 1268, Jan. 2004, pp. 608-613, (Abstract Only).
Whipple et al., "Zimmer Herbert Whipple Bone Screw System: Surgical Techniques for Fixation of Scaphoid and Other Small Bone Fractures," Zimmer, 2003, 59 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.
International Patent Application No. PCT/US2016/046953, International Search Report and Written Opinion dated Dec. 27, 2016, 13 pages.
European Patent Application No. 16837624.2, Extended European Search Report dated Apr. 17, 2019, 8 pages.
Gregg et al., "Plantar plate repair and Weil osteotomy for metatarsophalangeal joint instability," Foot and Ankle Surgery, vol. 13, 2007, pp. 116-121.
Weil et al., "Anatomic Plantar Plate Repair Using the Weil Metatarsal Osteotomy Approach," Foot & Ankle Specialist, vol. 4, No. 3, 2011, pp. 145-150.
Alvine et al., "Peg and Dowel Fusion of the Proximal Interphalangeal Joint," Foot & Ankle, vol. 1, No. 2, 1980, pp. 90-94.
Bednarz et al., "Modified Lapidus Procedure for the Treatment of Hypermobile Hallux Valgus," Foot & Ankle International, vol. 21, No. 10, Oct. 2000, pp. 816-821.
Carr et al., "Correctional Osteotomy for Metatarsus Primus Varus and Hallux Valgus," The Journal of Bone and Joint Surgery, vol. 50-A, No. 7, Oct. 1968, pp. 1353-1367.
Coetzee et al.," I he Lapidus Procedure: A Prospective Cohort Outcome Study," Foot & Ankle International, vol. 25, No. 8, Aug. 2004, pp. 526-531.
Doty et al., "Hallux valgus and hypermobility of the first ray: facts and fiction," International Orthopaedics, vol. 37, 2013, pp. 1655-1660.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online Nov. 21, 2014, pp. 437-440.
Lapidus, "The Author's Bunion Operation From 1931 to 1959," Clinical Orthopaedics, vol. 16, 1960, pp. 119-135.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online Jun. 3, 2014, pp. 548-556.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
"Accu-Cut Osteotomy Guide System," BioPro, Brochure, Oct. 2018, 2 pages.
"Acumed Osteotomiesystem Operationstechnik," Acumed, 2014, 19 pages (including 3 pages English translation).
Blomer, "Knieendoprothetik—Herstellerische Probleme und technologische Entwicklungen," Orthopade, vol. 29, 2000, pp. 688-696, including English Abstract on p. 689.
Bouaicha et al., "Fixation of Maximal Shift Scarf Osteotomy with Inside-Out Plating: Technique Tip," Foot & Ankle International Journal, vol. 32, No. 5, May 2011, pp. 567-569.
"Futura Forefoot Implant Arthroplasty Products," Tornier, Inc., 2008, 14 pages.
Gotte, "Entwicklung eines Assistenzrobotersystems fur die Knieendoprothetik," Forschungsberichte, Technische Universitat Munchen, 165, 2002, 11 pages, including partial English Translation.
"HAT-TRICK Lesser Toe Repair System, Foot and Ankle Technique Guide, Metatarsal Shortening Osteotomy Surgical Technique," Smith & Nephew, 2014, 16 pages.
Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
Lieske et al., "Implantation einer Sprunggelenktotalendo-prothese vom Typ Salto 2," Operative Orthopadie und Traumatologie, vol. 26, No. 4, 2014, pp. 401-413, including English Abstract on p. 403.
Magin, "Computemavigierter Gelenkersatz am Knie mit dem Orthopilot," Operative Orthopädie und Traumatologie, vol. 22, No. 1, 2010, pp. 63-80, including English Abstract on p. 64.
Magin, "Die belastungsstabile Lapidus-Arthrodese bei Hallux-valgus-Deformitat mittels IVP-Plattenfixateur (V-TEK-System)," Operative Orthopadie und Traumatologie, vol. 26, No. 2, 2014, pp. 184-195, including English Abstract on p. 186.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Odenbring et al., "A guide instrument for high tibial osteotomy," Acta Orthopaedica Scandinavica, vol. 60, No. 4, 1989, pp. 449-451.
Otsuki et al., "Developing a novel custom cutting guide for curved per-acetabular osteotomy," International Orthopaedics (SICOT), vol. 37, 2013, pp. 1033-1038.
"Patient to Patient Precision, Accu-Cut, Osteotomy Guide System," BioPro, Foot & Ankle International, vol. 23, No. 8, Aug. 2002, 2 pages.
Peters et al., "Flexor Hallucis Longus Tendon Laceration as a Complication of Total Ankle Arthroplasty," Foot & Ankle International, vol. 34, No. 1, 2013, pp. 148-149.

(56) References Cited

OTHER PUBLICATIONS

"Prophecy Inbone Preoperative Navigation Guides," Wright Medical Technology, Inc., Nov. 2013, 6 pages.

"TRAYHACK Ulnar Shortening Generation II Low-Profile Locking System Surgical Technique," Wright Medical Technology, Inc., Dec. 2013, 20 pages.

Saltzman et al., "Prospective Controlled Trial of STAR Total Ankle Replacement Versus Ankle Fusion: Initial Results," Foot & Ankle International, vol. 30, No. 7, Jul. 2009, pp. 579-596.

"Smith & Nephew scores a HAT-TRICK with its entry into the high-growth hammertoe repair market," Smith & Nephew, Jul. 31, 2014, 2 pages.

Tricot et al., "3D-corrective osteotomy using surgical guides for posttraumatic distal humeral deformity," Acta Orthopaedica Belgica, vol. 78, No. 4, 2012, pp. 538-542.

Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.

Vitek, "Neue Techniken in der Fußchirurgie Das V-tek-System," ABW Wissenschaftsverlag GmbH, 2009, 11 pages, including English Abstract.

Wendl et al., "Navigation in der Knieendoprothetik," OP-Journal, vol. 17, 2002, pp. 22-27, including English Abstract.

\* cited by examiner

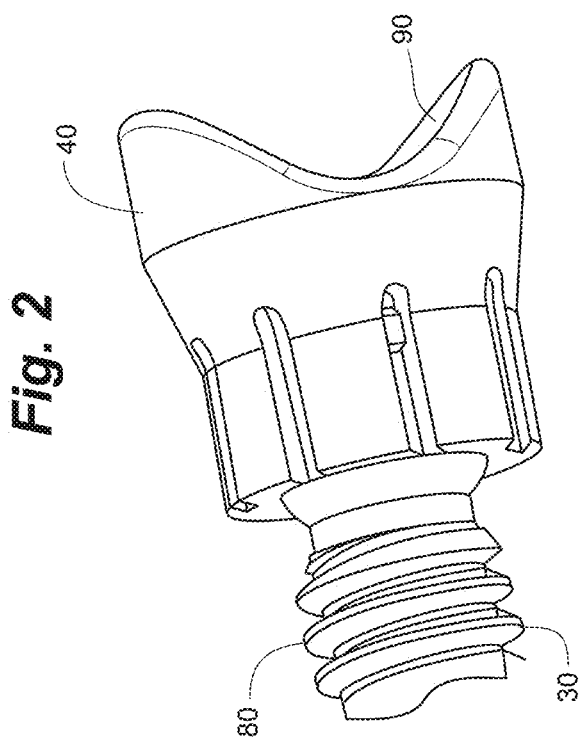

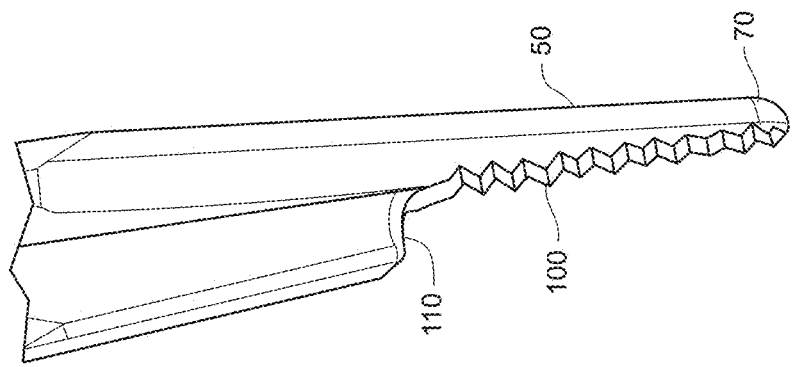

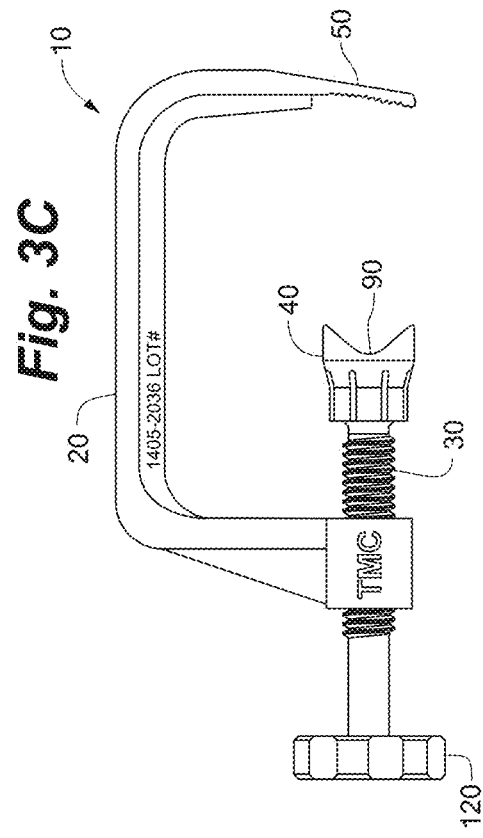
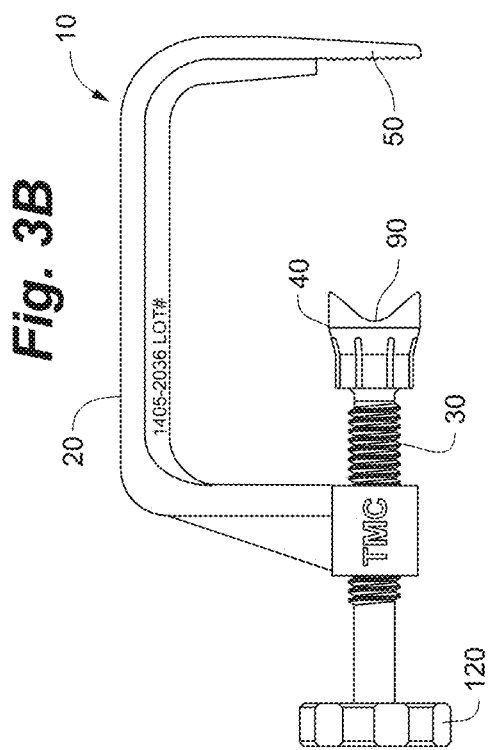

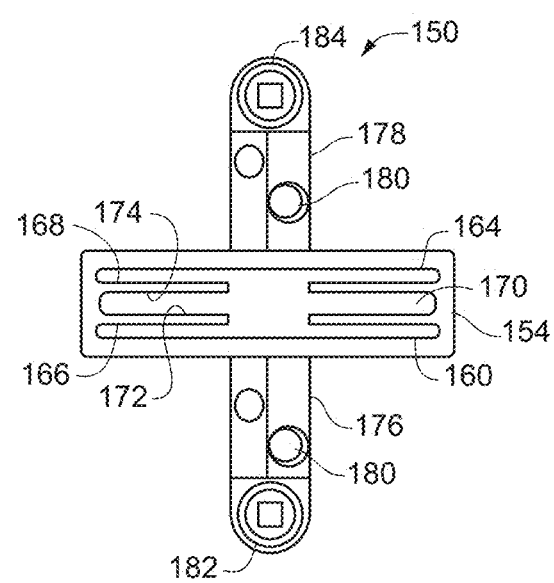

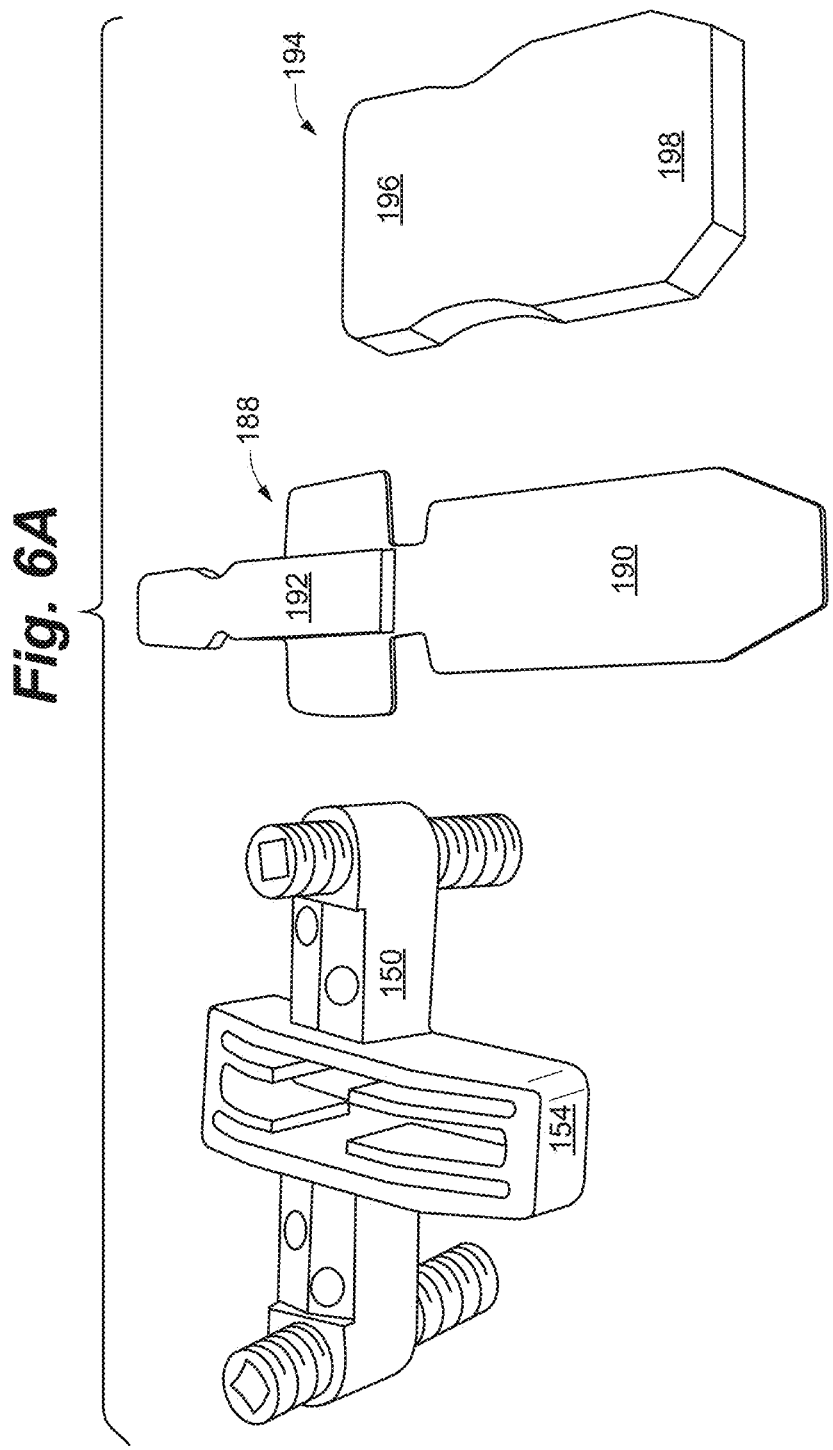

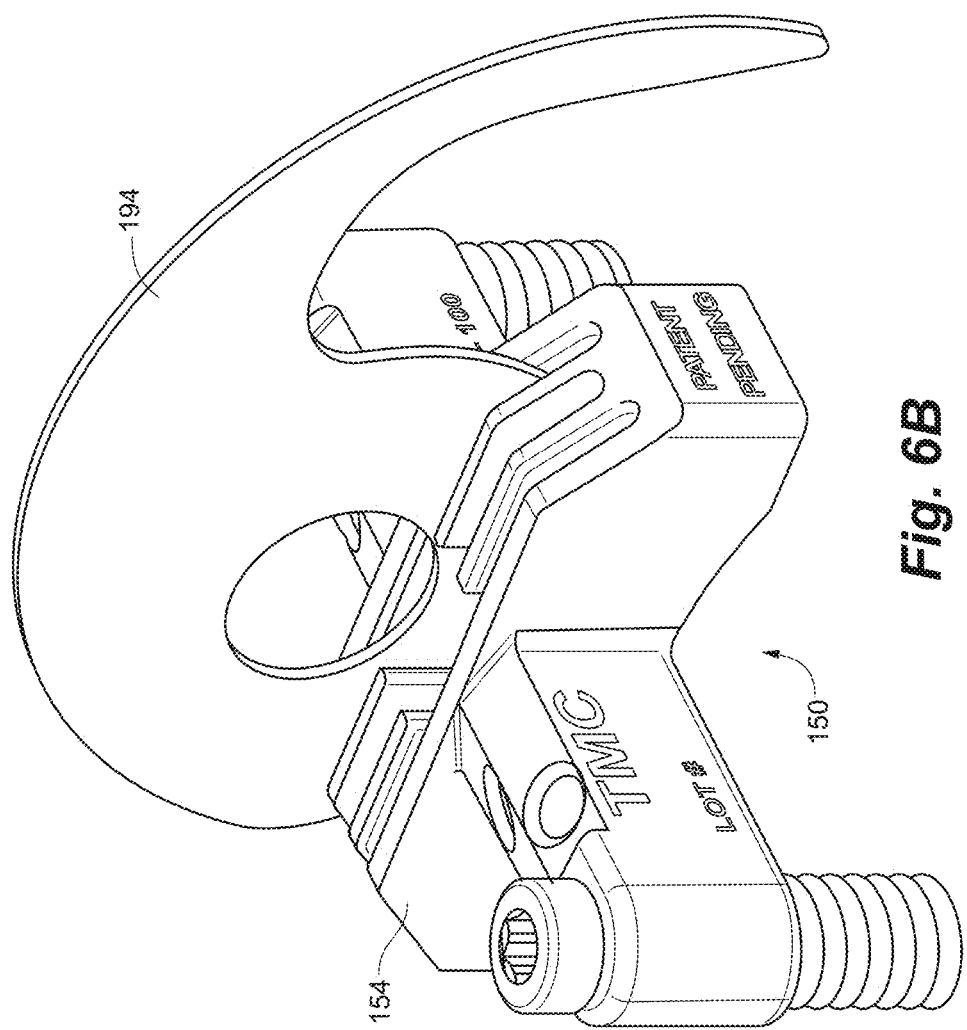

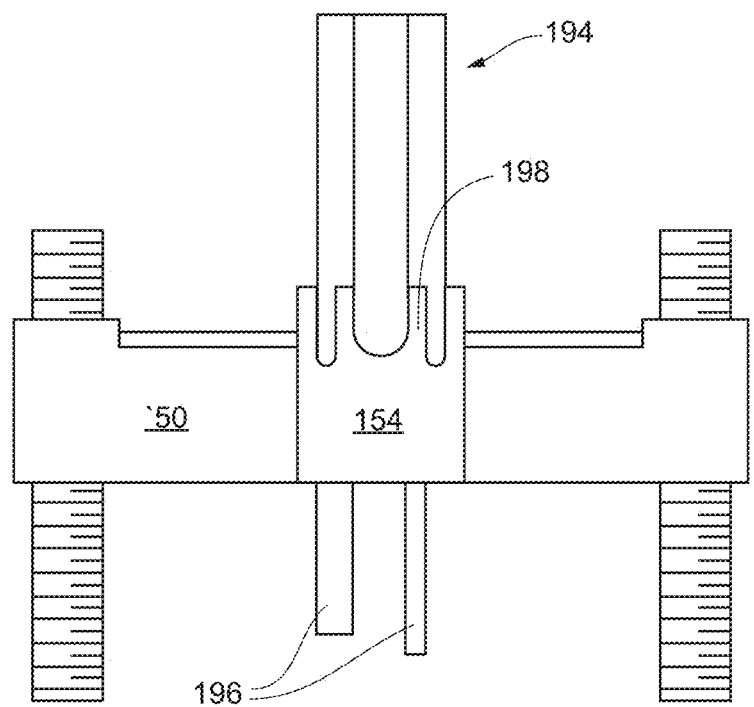

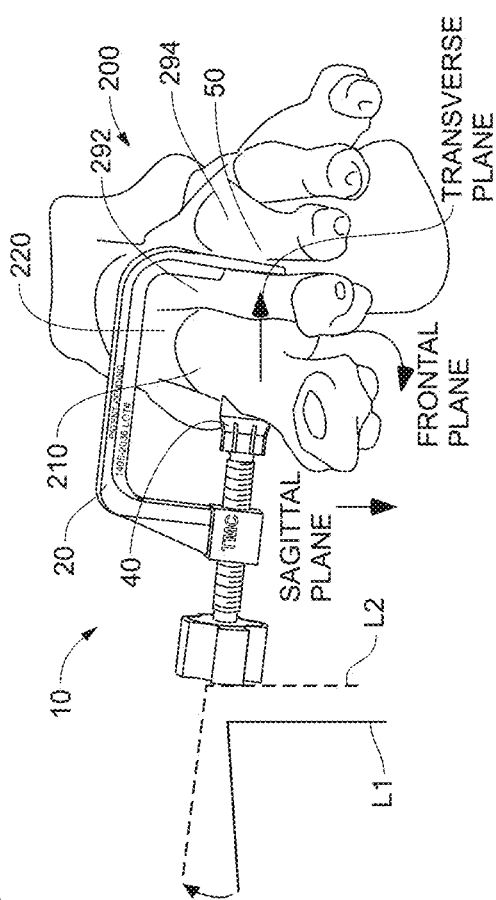
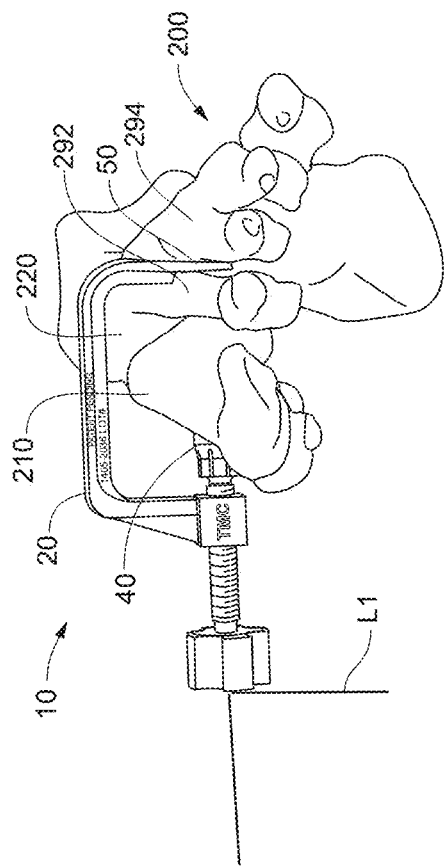
Fig. 9A
Fig. 9B

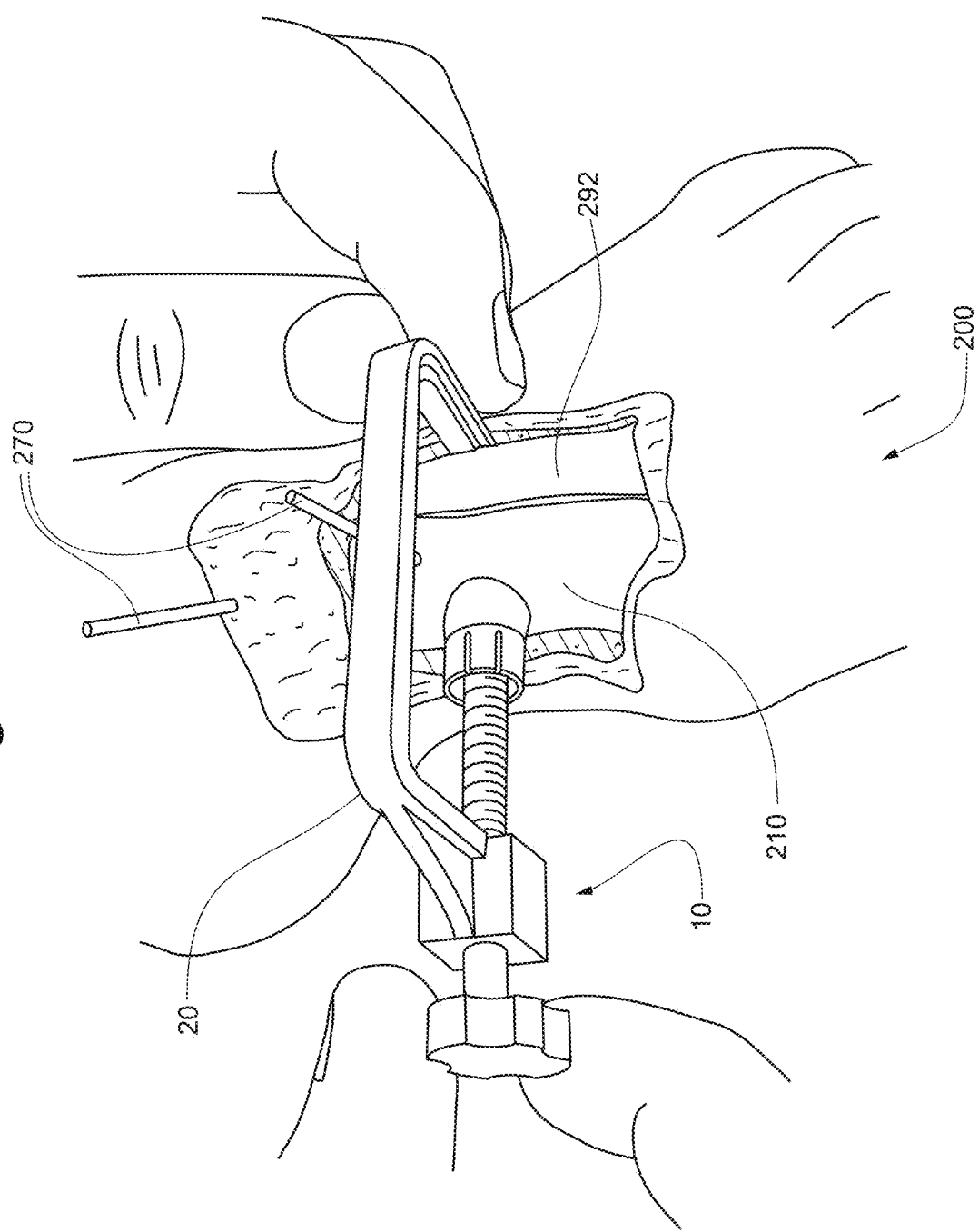

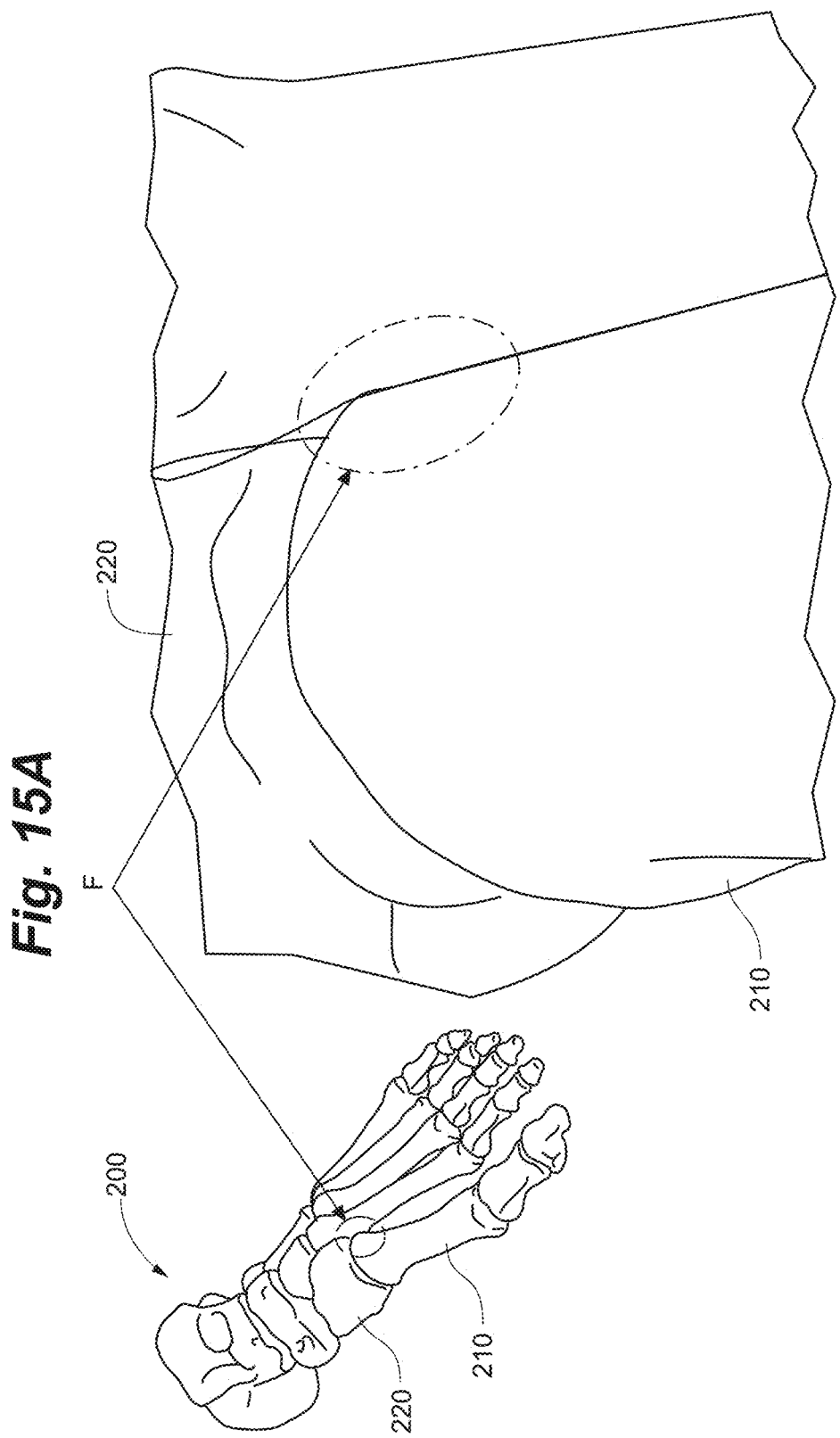

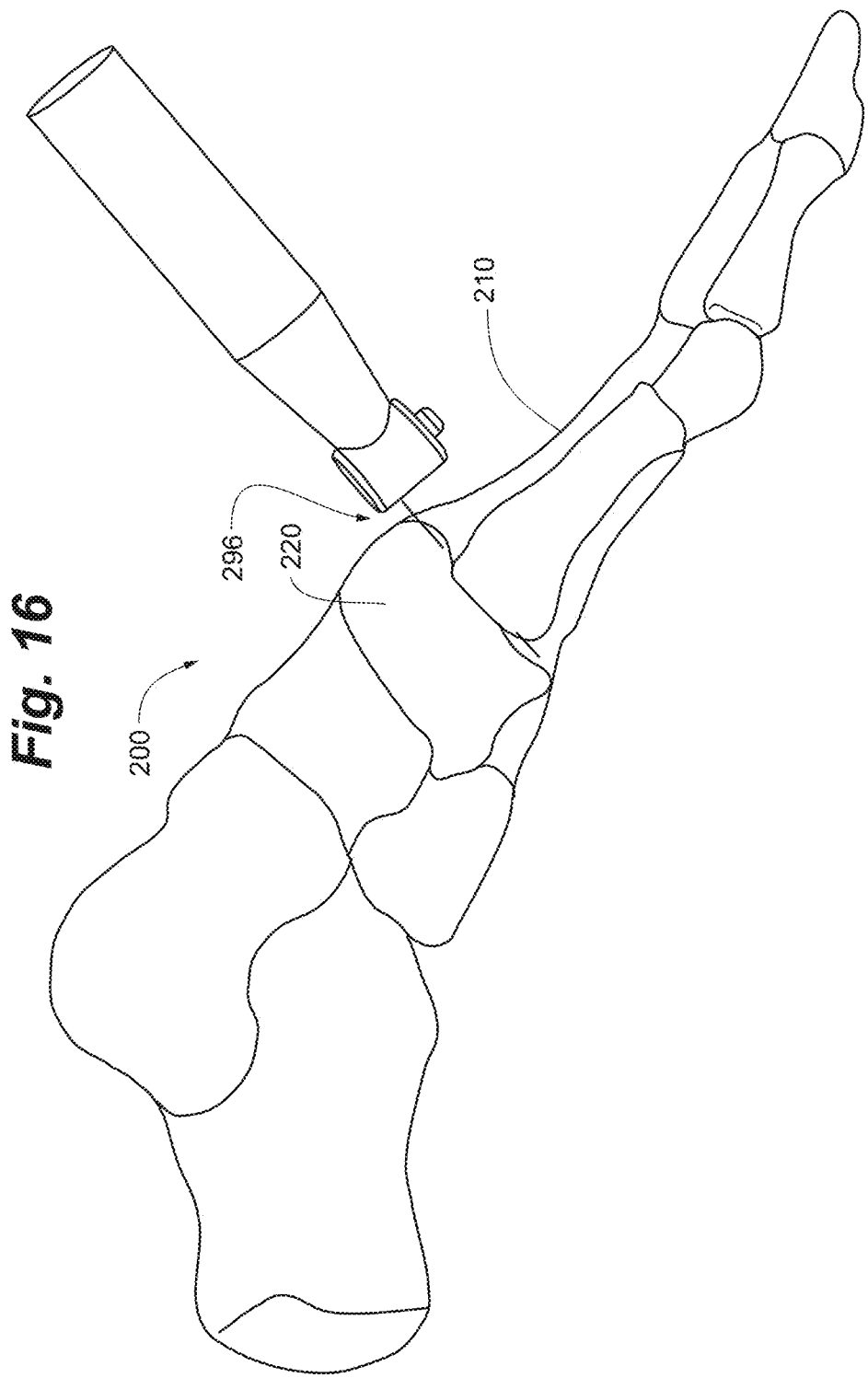

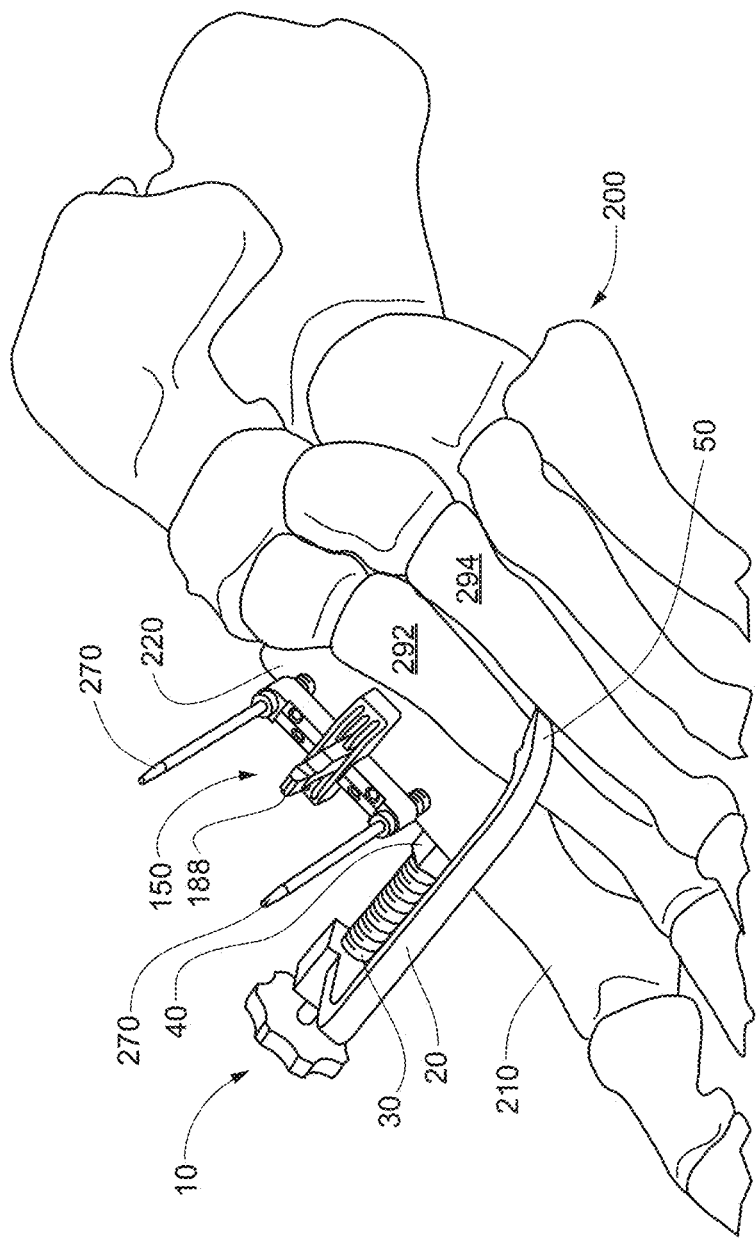

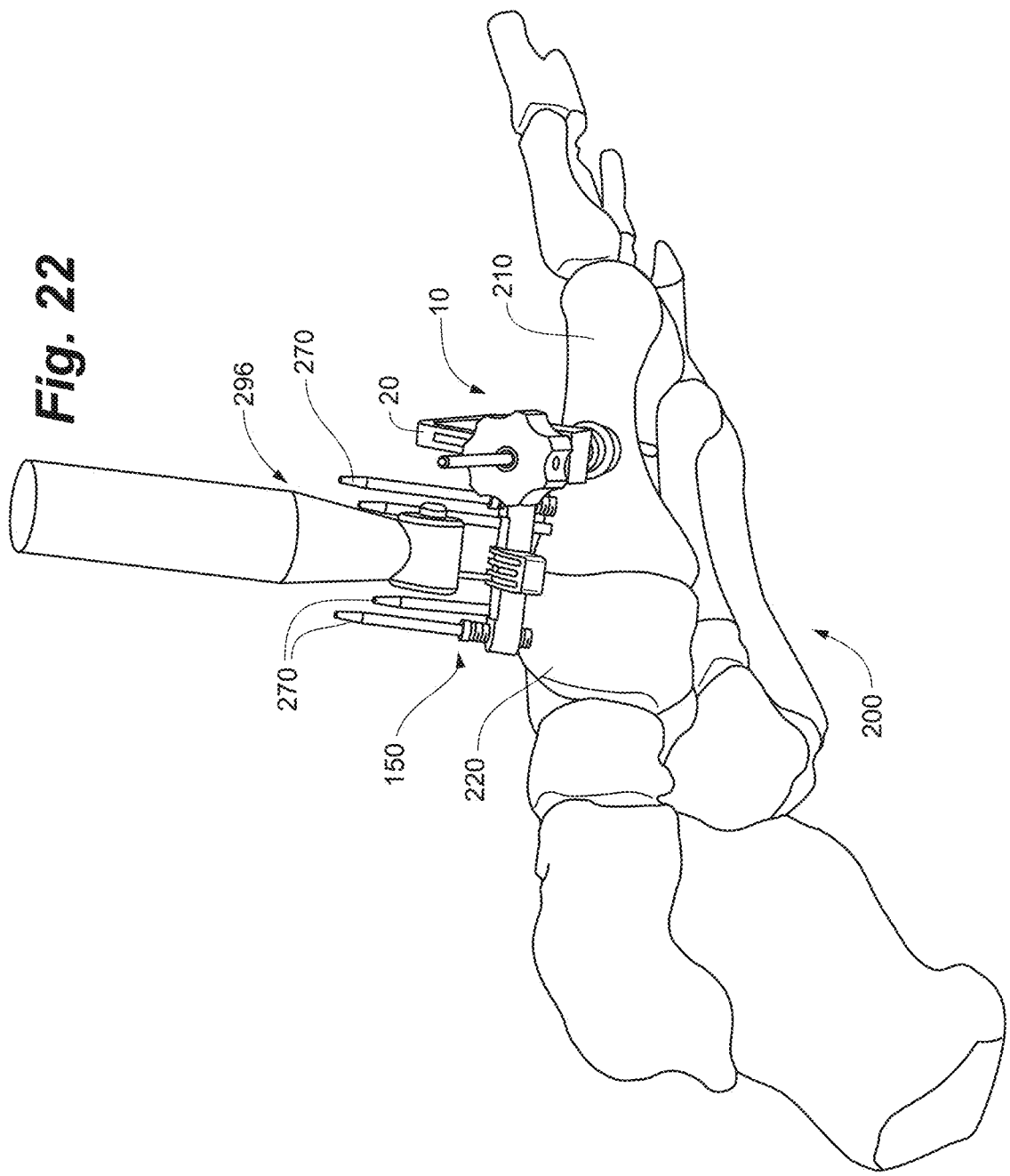

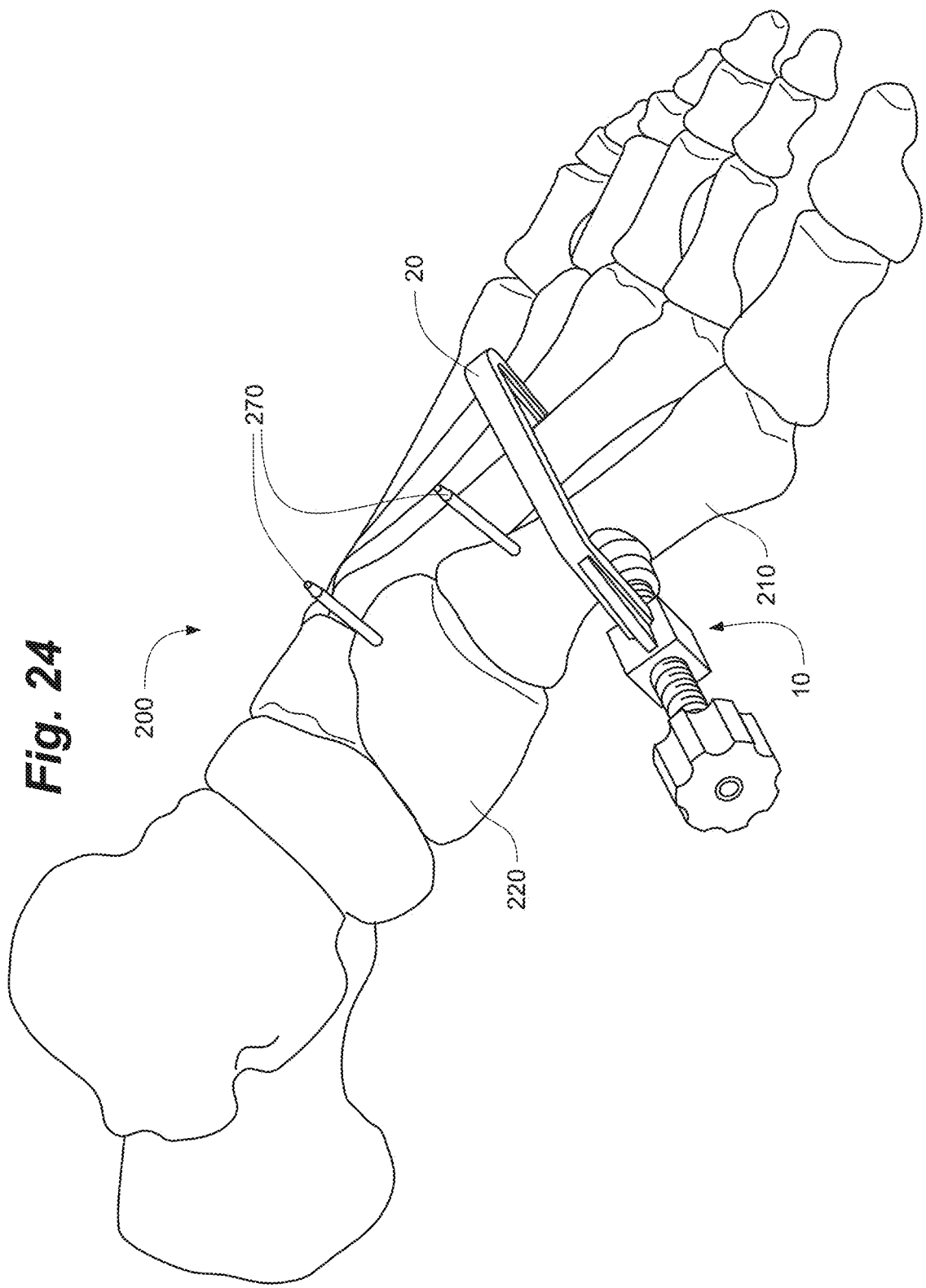

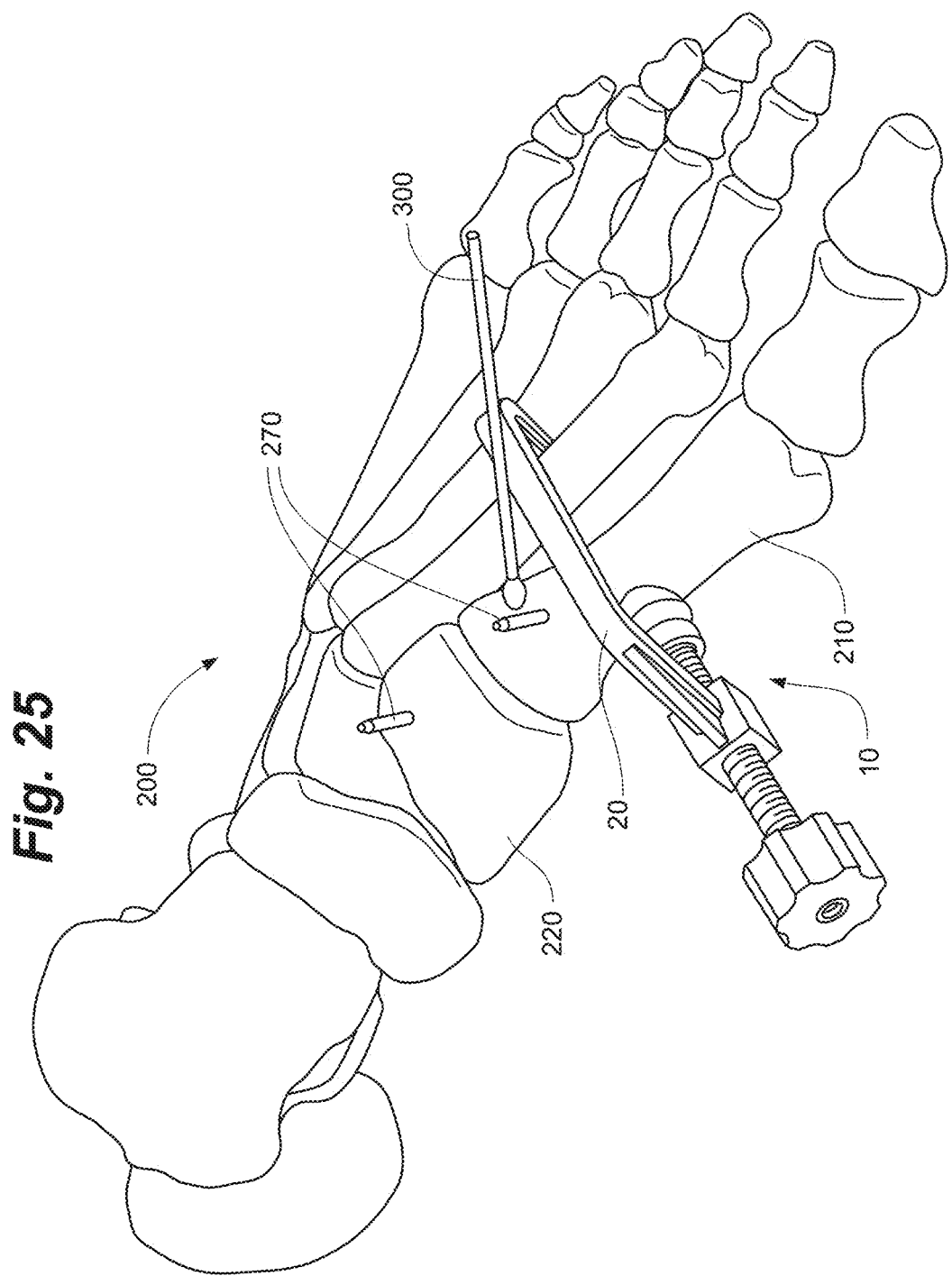

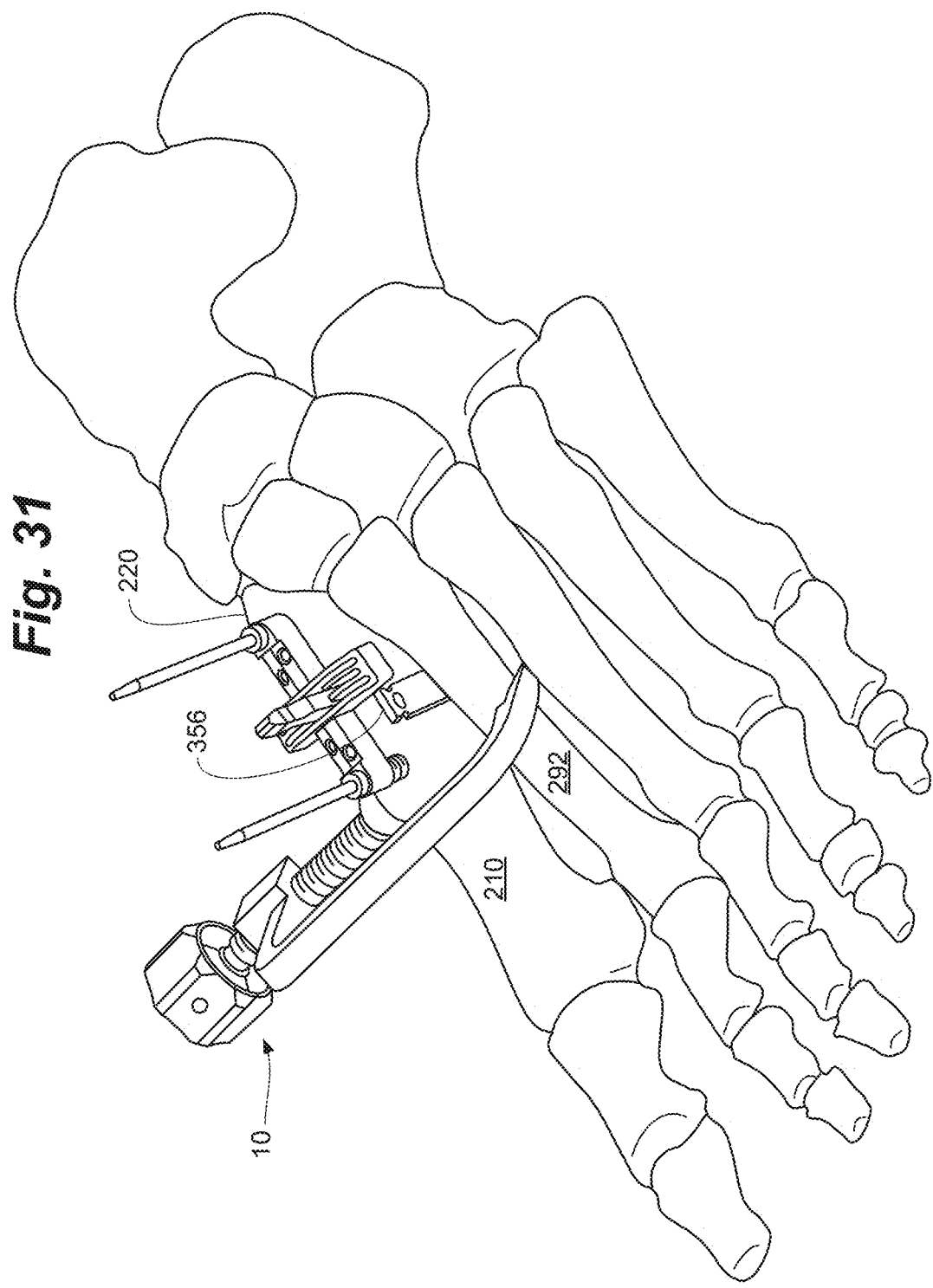

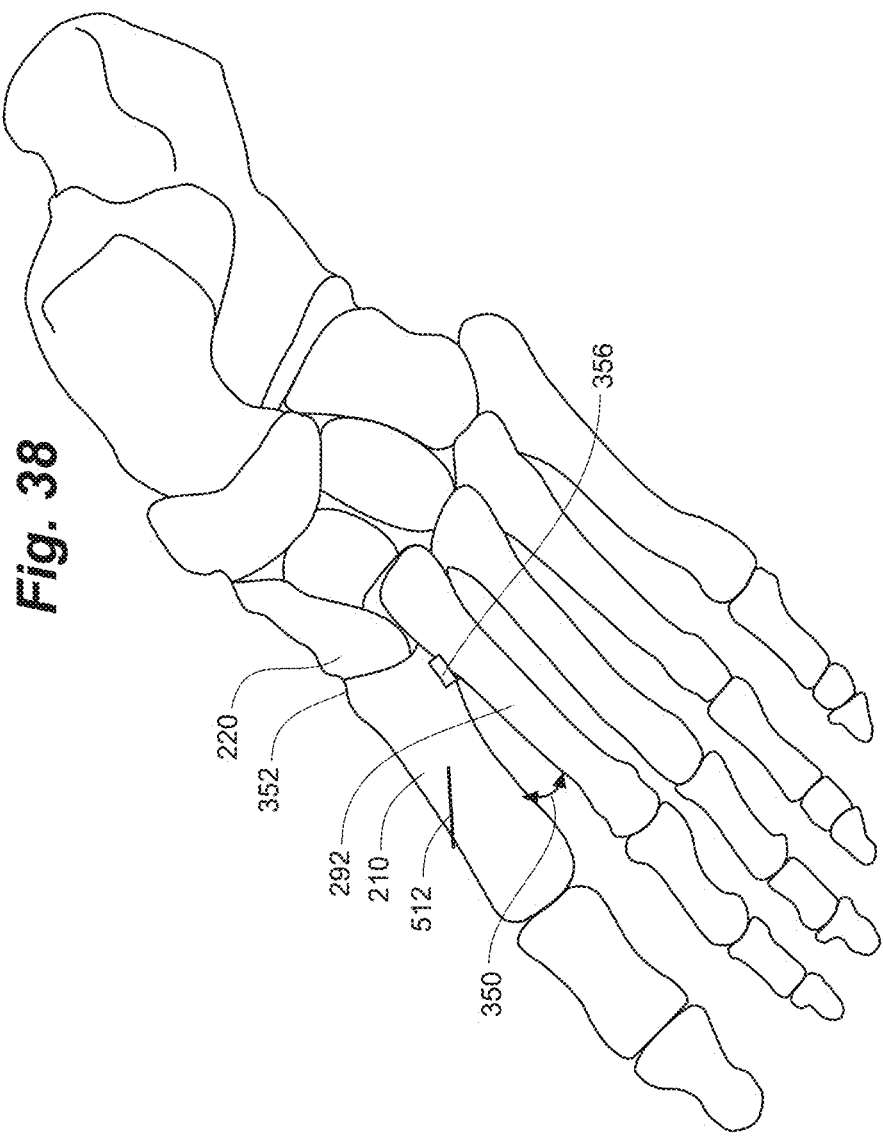

TARSAL-METATARSAL JOINT PROCEDURE UTILIZING FULCRUM

RELATED APPLICATIONS

This application is a continuation of U.S. patent application Ser. No. 15/236,464, filed Aug. 14, 2016, which in turn claims the benefit of U.S. Provisional Application No. 62/293,189, filed Feb. 9, 2016, and is a continuation-in-part of U.S. patent application Ser. No. 14/981,335, filed Dec. 28, 2015, now U.S. Pat. No. 9,622,805, issued Apr. 18, 2017, which claims the benefit of U.S. Provisional Application No. 62/205,338, filed Aug. 14, 2015. The entire contents of all these applications are incorporated herein by reference.

TECHNICAL FIELD

This disclosure relates generally to devices and methods for positioning and/or preparing bones.

BACKGROUND

Bones, such as the bones of a foot, may be anatomically misaligned. In certain circumstances, surgical intervention is required to correctly align the bones to reduce patient discomfort and improve patient quality of life.

SUMMARY

Embodiments of the present invention include methods for fixing an orientation of a bone or bones. In general, the method of positioning a bone includes the steps of moving a bone from an anatomically misaligned position to an anatomically aligned position with respect to another bone and preparing an end of the bone and a facing end of another bone. In some embodiments, at least one bone end is prepared after the bone is moved into the aligned position. In some embodiments, the bone is anatomically aligned in more than one plane such that the bone both translates and rotates in response to a moving force.

One embodiment includes a method of correcting a bunion deformity. The method includes inserting a fulcrum between a first metatarsal and a second metatarsal, where the first metatarsal is anatomically misaligned with respect to the second metatarsal. The method further includes preparing an end of the first metatarsal and preparing an end of a medial cuneiform opposing the end of the first metatarsal. In addition, the method involves moving a distal portion of the first metatarsal toward the second metatarsal in a transverse plane, thereby pivoting a proximal portion of the first metatarsal about the fulcrum and reducing the intermetatarsal angle between the first metatarsal and the second metatarsal.

In one example, a fulcrum is described for use in a bone realignment procedure. The fulcrum includes a body and a handle. The body is configured to be inserted in an intermetatarsal space between adjacent metatarsals. The handle is operatively connected to the body. The example specifies that the handle projects at a non-zero degree angle from the body to define a tissue retraction space between the handle and the body.

In another example, a multidimensional fulcrum is described that includes a fulcrum body having a length extending from a first end to a second end, a width, and a thickness. The first end of the fulcrum has a first thickness and is configured to be inserted into an intermetatarsal space between adjacent metatarsals of a first size. The second end of the fulcrum has a second thickness and is configured to be inserted into an intermetatarsal space between adjacent metatarsals of a second size. The example specifies that the second thickness is greater than the first thickness.

The details of one or more examples are set forth in the accompanying drawings and the description below. Other features, objects, and advantages will be apparent from the description and drawings, and from the claims.

BRIEF DESCRIPTION OF THE DRAWINGS

The following drawings are illustrative of particular embodiments of the present invention and, therefore, in no way limit the scope of the invention. The drawings are not necessarily to scale (unless otherwise stated) and are intended for use in conjunction with the explanations in the following detailed description. Embodiments of the invention will hereinafter be described with respect to the appended drawings, wherein like numerals denote like elements.

FIG. 2 is a side perspective view of a bone engagement member of a bone positioning guide in accordance with an embodiment of the invention.

FIG. 3A is a side perspective view of a tip of a bone positioning guide in accordance with an embodiment of the invention.

FIG. 3B is a side view of a bone positioning guide with a straight tip in accordance with an embodiment of the invention.

FIG. 3C is a side view of a bone positioning guide with a nonlinear tip in accordance with an embodiment of the invention.

FIG. 5 is a top plan view of a bone preparing guide in accordance with an embodiment of the invention.

FIG. 6A is a perspective view of a bone preparing guide, a spacer, and a tissue removing instrument location check member in accordance with an embodiment of the invention.

FIG. 6B is a perspective view of another embodiment of a tissue removing instrument check location member engaged with a bone preparing guide.

FIG. 8 is a perspective view of a bone preparing guide engaged with a tissue removal instrument location check member in accordance with an embodiment of the invention.

FIG. 9A is a front view of a bone positioning guide on a deformed foot in accordance with an embodiment of the invention.

FIG. 9B is a front view of a bone positioning guide on a foot with a corrected alignment in accordance with an embodiment of the invention.

FIGS. 11A-C depict a sequence of a bone positioning operation using a bone positioning guide on a foot at first, second, and third positions in accordance with an embodiment of the invention.

FIG. 15A is a perspective view and an enlarged view of a foot.

FIG. 16 is a side perspective view of a foot depicting a bone preparation instrument inserted into a joint.

FIG. 21B is another perspective view of a foot depicting a bone positioning guide on the foot after an alignment of a first metatarsal and a positioning of a bone preparation guide with pins.

FIG. 22 is a perspective view of a foot depicting a bone preparation instrument preparing a bone of the foot guided by a guide surface of a bone preparation guide.

FIG. 24 is a perspective view of a foot depicting a bone positioning guide on the foot and pins.

FIG. 25 is a perspective view of a foot depicting a bone positioning guide on the foot and a compression pin.

FIG. 31 illustrates an example bone positioning operation in which a fulcrum is positioned at an intersection between a first bone and a second bone.

FIG. 38 is a perspective view of a foot showing an example position of a fulcrum during a bone correction procedure according to the method of FIG. 37.

DETAILED DESCRIPTION

The following detailed description is exemplary in nature and is not intended to limit the scope, applicability, or configuration of the invention. Rather, the following description provides practical illustrations for implementing exemplary embodiments of the disclosure. Examples of constructions, materials, and dimensions are provided for selected elements, and all other elements employ that which is known to those of ordinary skill in the field of the invention. Those skilled in the art will recognize that many of the noted examples have a variety of suitable alternatives.

Embodiments of the invention include a bone positioning guide and method of positioning bones in a medical procedure. In an exemplary application, embodiments of the bone positioning guide can be useful during a surgical procedure, such as a bone alignment, osteotomy, fusion procedure, and/or other procedures where one or more bones are to be prepared (e.g., cartilage or bone removal and/or cut). Such a procedure can be performed, for example, on bones (e.g., adjacent bones separated by a joint or different portions of a single bone) in the foot or hand, where bones are relatively smaller compared to bones in other parts of the human anatomy. In one example, a procedure utilizing an embodiment of the bone positioning guide can be performed to correct an alignment between a metatarsal (e.g., a first metatarsal) and a second metatarsal and/or a cuneiform (e.g., a medial, or first, cuneiform), such as in a bunion correction surgery. An example of such a procedure is a Lapidus procedure (also known as a first tarsal-metatarsal fusion). In another example, the procedure can be performed by modifying an alignment of a metatarsal (e.g., a first metatarsal). An example of such a procedure is a basilar metatarsal osteotomy procedure.

Figure 1:
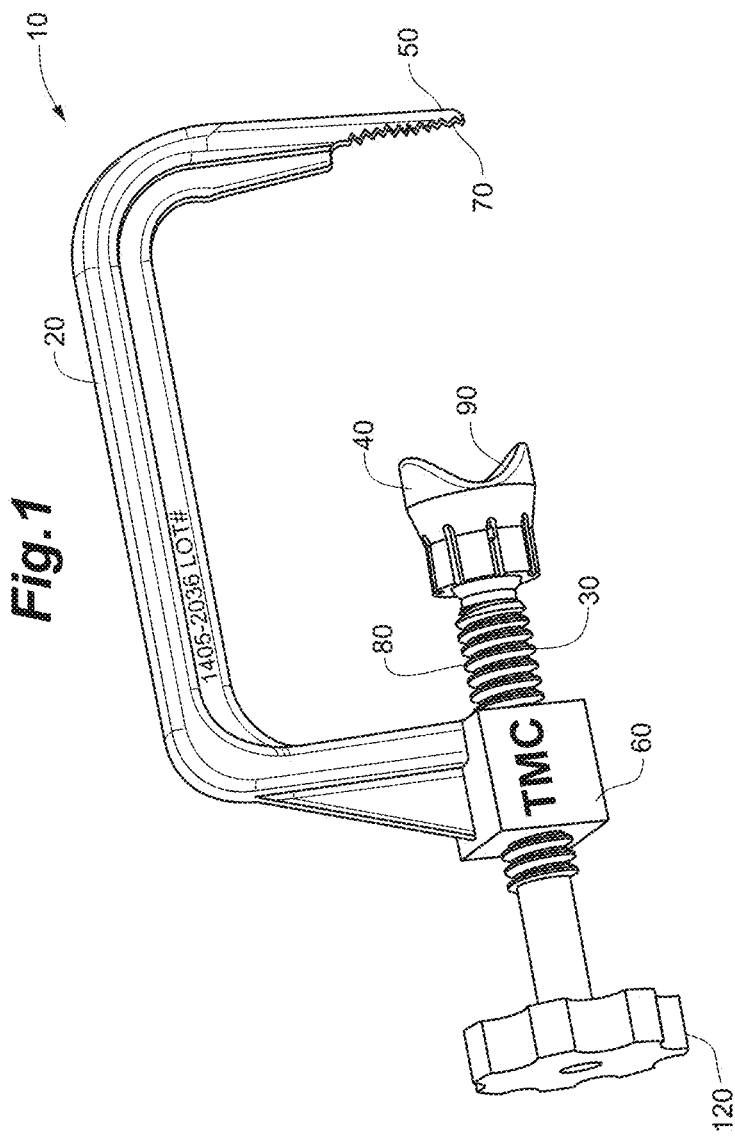
FIG. 1 is a side perspective view of a bone positioning guide in accordance with an embodiment of the invention.

FIG. 1 shows a side perspective view of a bone positioning guide 10 in accordance with an embodiment of the invention. The bone positioning guide 10 can be useful for positioning a bone (e.g., orientating and/or translating) during a medical procedure. In some embodiments, the bone positioning guide includes a bone engagement member, a tip, a mechanism to urge the bone engagement member and the tip towards each other (e.g. moving the bone engagement member towards the tip, moving the tip towards the bone engagement member, or moving both simultaneously), and an actuator to actuate the mechanism. When the mechanism is actuated it causes a first bone engaged with the bone engagement member to move to correct an alignment in more than one plane with respect to a second bone in contact with the tip. In some embodiments, the correction in more than one plane includes a correction about an axis in a frontal plane.

In the embodiment of FIG. 1, bone positioning guide 10 includes a main body member 20 and a shaft 30, and the bone engagement member 40 is connected to the shaft and the tip 50 is connected to the main body member. In general, the main body member 20 can be sized and shaped to clear anatomy or other instrumentation (e.g., pins and guides) while positioned on a patient. In the embodiment of FIG. 1, the main body member 20 includes a generally C-shaped configuration with a first end 60 and a second end 70. In some embodiments, the main body is sized and configured to engage bones of a human foot. In addition, although bone positioning guide 10 is illustrated as being formed of two components, main body member 20 and shaft 30, the guide can be fabricated from more components (e.g., 3, 4, or more) that are joined together to form the guide.

A shaft 30 can be movably connected to the main body member 20 proximate its first end 60. In some embodiments, the shaft 30 includes threads 80 that engage with the main body member 20 such that rotation of the shaft translates the shaft with respect to the main body member. In other embodiments, the shaft can slide within the main body member and can be secured thereto at a desired location with a set screw. In yet other embodiments, the shaft can be moved with respect to the main body by a ratchet mechanism. In the embodiment shown, the shaft moves along an axis that intersects the tip 50. In other embodiments, such as that described with respect to FIG. 34, the shaft 30 and/or bone engagement member 40 is offset from tip 50.

As shown in FIG. 2, embodiments of the bone positioning device can have a bone engagement member 40. In some embodiments, the bone engagement member includes a surface 90 configured to contact a bone, such as a metatarsal or a cuneiform. In the embodiment shown, the surface 90 is concave. Such a surface is adapted to promote surface contact with a generally cylindrical bone, such as a metatarsal. Other embodiments of surface shapes include planar surfaces and V-shaped surfaces. When using a concave or V-shaped bone engagement member 40, the sidewalls of the concavity or V-shaped groove may be symmetrical or asymmetrical. In a symmetrical configuration, the bottom of the concavity or groove can be centered between upwardly extending sidewalls configured to receive a bone. Each sidewall can extend upwardly to the same height and/or at the same slope. In the asymmetrical configuration, one sidewall can have a different configuration than the opposing sidewall. For example, one of the sidewalls may extend upwardly from the bottom of the concavity or groove to a lower height than the opposing sidewall. As another example, one sidewall may extend upwardly at a different angle than the opposing sidewall. The asymmetrical configuration can be useful for applying a force that is biased laterally instead of only being linear toward tip 50.

In some embodiments, bone engagement member 40 includes a pin or a clamp. Independent of whether bone engagement member 40 includes such pin or clamp, the bone engagement member can engage an anatomical feature of a bone, such as a ridge (e.g., a medial ridge of a first metatarsal). In such embodiments, the engagement generally prohibits rotational movement of the bone with respect to the bone engagement member. In other embodiments, bone may be allowed to rotate with respect to the bone engagement member.

In the embodiment shown, the bone engagement member 40 is provided on an end of the shaft 30. In the embodiment of the shaft shown having threads 80, the bone engagement member 40 can be rotatably coupled to the shaft 30. In such embodiments, as the shaft is rotated relative to the main body member the bone engagement member 40 may or may not rotate with respect to the main body member even as it translates with respect to the main body member along with the shaft 30 and rotates with respect to the shaft. The bone engagement member may oscillate about the shaft 30, but generally does not rotate with respect to bone after contact with the bone.

FIGS. 3A-C depict a tip 50 of bone positioning guide 10, which can be at a second end 70 of the main body member opposite the first end. The tip 50 can be useful for contacting a bone, generally a bone distinct from a bone contacting the bone engagement member. For example, if the bone engagement member is in contact with a first metatarsal, the tip can be in contact with a metatarsal other than the first metatarsal (e.g., the second, third, fourth, or fifth metatarsal). In some embodiments, the tip is tapered to facilitate percutaneous insertion and contact with bone. The tip can also include a textured surface 100, such as serrated, roughened, crosshatched, knurled, etc., to reduce slippage between the tip and bone. In the embodiment shown, the tip further includes a stop 110 to limit a depth of insertion. The shape of the tip can be configured to stably contact bone. For example, FIG. 3B shows a side view of the bone positioning guide with a generally straight tip 50, while FIG. 3C shows a side view of the bone positioning guide with a nonlinear tip 50 (e.g., a tip that is angled or curved). In some embodiments, the tip is configured to restrict translational movement between it and a bone, but to allow rotational movement between it and the bone.

Figure 4:
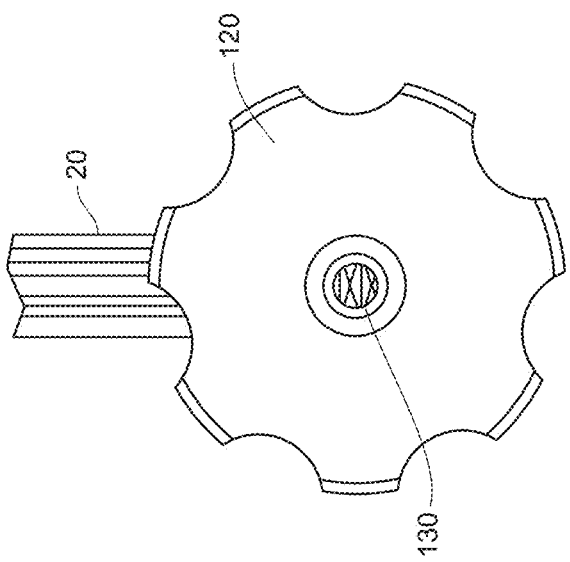
FIG. 4 is an end view of an actuator of a bone positioning guide in accordance with an embodiment of the invention.

As shown in FIG. 4, bone positioning guide 10 can also include an actuator (e.g., a knob or a handle) 120 to actuate the mechanism, in this embodiment associated with the shaft. In the embodiment shown, the actuator can be useful for allowing a user to rotate the shaft with respect to the main body member 20. Also as shown in FIG. 4, the actuator, shaft, and bone engagement member may include a cannulation 130 to allow the placement of a fixation wire (e.g., K-wire) through these components and into contact with or through a bone engaged with the bone engagement member. For example, the fixation wire can be placed into the bone engaged with bone engagement member 40 to fix the position of the bone engagement member with respect to the bone. In another example, the fixation wire can be placed through the bone in contact with the bone engagement member and into an adjacent bone to maintain a bone position of the bone in contact with the bone engagement member and the adjacent bone.

In other embodiments, the mechanism to urge the bone engagement member and the tip towards each other can include a tenaculum or tong structure. In such embodiments, the guide can include a first shaft pivotably connected to a second shaft. A first end of each shaft can include an actuator, such as a handle. A second end of the first shaft can include a bone engagement member, as described above. And a second end of the second shaft can include a tip, as described above. In use, the actuator can be actuated (e.g., squeezed together) to move the bone engagement member and the tip closer together to position bone. Other embodiments of this type may include another set of shafts and another pivoting connection such that the bone engagement member and tip translate towards each other when the actuator is actuated.

In other embodiments, the mechanism to urge the bone engagement member and the tip towards each other can include a rack and pinion structure. In such embodiments, the rack can include a tip, as described above. And the pinion can include a bone engagement member, as described above, and an actuator (e.g., a knob). In use, the actuator can be actuated (e.g., turned about an axis generally perpendicular to a direction of travel) to move the bone engagement member and the tip closer together to position bone.

Embodiments of the bone positioning guide may include any suitable materials. In certain embodiments, the bone positioning guide is fabricated from a radiolucent material such that it is relatively penetrable by X-rays and other forms of radiation, such as thermoplastics and carbon-fiber materials. Such materials are useful for not obstructing visualization of bones using an imaging device when the bone positioning guide is positioned on bones.

Embodiments of the bone positioning guide can be useful in operation for positioning a bone or bones during a medical procedure. Bone positioning can be useful, for instance, to correct an anatomical misalignment of bones and maintain an anatomically aligned position, such as in a bone alignment and/or fusion procedure. In some embodiments, the bone positioning guide is capable of reducing an angle between the first metatarsal and the second metatarsal from over 10 degrees (e.g., up to about 35 degrees) to about 10 degrees or less (e.g., to about 1-5 degrees), including to negative angles of about −5 degrees. In some embodiments, the bone positioning guide is also capable of rotating the first metatarsal about its long axis with respect to the medial cuneiform from a rotational angle of over 4 degrees to a rotational angle of less than 4 degrees (e.g., to about 0 to 2 degrees).

In some embodiments, a bone preparation guide may be provided to facilitate the preparation of a bone. The bone preparation guide can be provided with a bone positioning guide, or either device can be provided or used independently. An example of a bone preparation guide 150 is shown in FIG. 5. In some embodiments, the bone preparation guide 150 includes a body 154 defining a first guide surface 160 to define a first preparing plane and a second guide surface 164 to define a second preparing plane. A tissue removing instrument (e.g., a saw, rotary bur, osteotome, etc., not shown) can be aligned with the surfaces to remove tissue (e.g., remove cartilage or bone and/or make cuts to bone). The first and second guide surfaces 160, 164 can be spaced from each other by a distance, (e.g., between about 2 millimeters and about 10 millimeters, such as between about 4 and about 7 millimeters). In the embodiment shown, the first and second guide surfaces are parallel, such that cuts to adjacent bones using the guide surfaces will be generally parallel.

In some embodiments, as shown in FIG. 5, a first facing surface 166 is positioned adjacent the first guide surface 160 and/or a second facing surface 168 is positioned adjacent the second guide surface 164. In such embodiments, the distance between the first guide surface and the first facing surface defines a first guide slot, and the distance between the second guide surface and the second facing surface defines a second guide slot. Each slot can be sized to receive a tissue removing instrument to prepare the bone ends. The first and second slots may be parallel or skewed. In the illustrated embodiment, the facing surfaces each contain a gap, such that the surface is not a single, continuous surface. In other embodiments, the facing surfaces can be a single, continuous surface lacking any such gap.

An opening 170 can be defined by the body 154 between the first and second guide surfaces. The opening can be an area between the guide surfaces useful for allowing a practitioner to have a visual path to bones during bone preparation and/or to receive instruments. In the embodiment shown, the opening extends across the body and a distance from a surface 172 opposite of the first facing surface 166 to a surface 174 opposite of the second facing surface 168.

The embodiment shown also includes a first end 176 extending from the body 154 in a first direction and a second end 178 extending from the body in a second direction. The second direction can be different than the first direction (e.g., an opposite direction). As shown, each of the first end and the second end can include at least one fixation aperture 180 configured to receive a fixation pin (not shown in FIG. 5) to secure the guide to a bone. As shown, such apertures may extend through the end at a vertical or skewed angle relative to a top surface of the guide.

The bone preparation guide 150 can also include a first adjustable stabilization member 182 engaged with the first end 176. In some embodiments, the bone preparation guide can include a second adjustable stabilization member 184 engaged with the second end 178. Each of the members can be threaded and engage a threaded aperture defined by the ends. The elevation of each end can be adjusted with respect to a bone by adjusting the stabilization member. In some embodiments, as shown, the stabilization members are cannulated such that they can receive a fixation pin.

Figure 7:
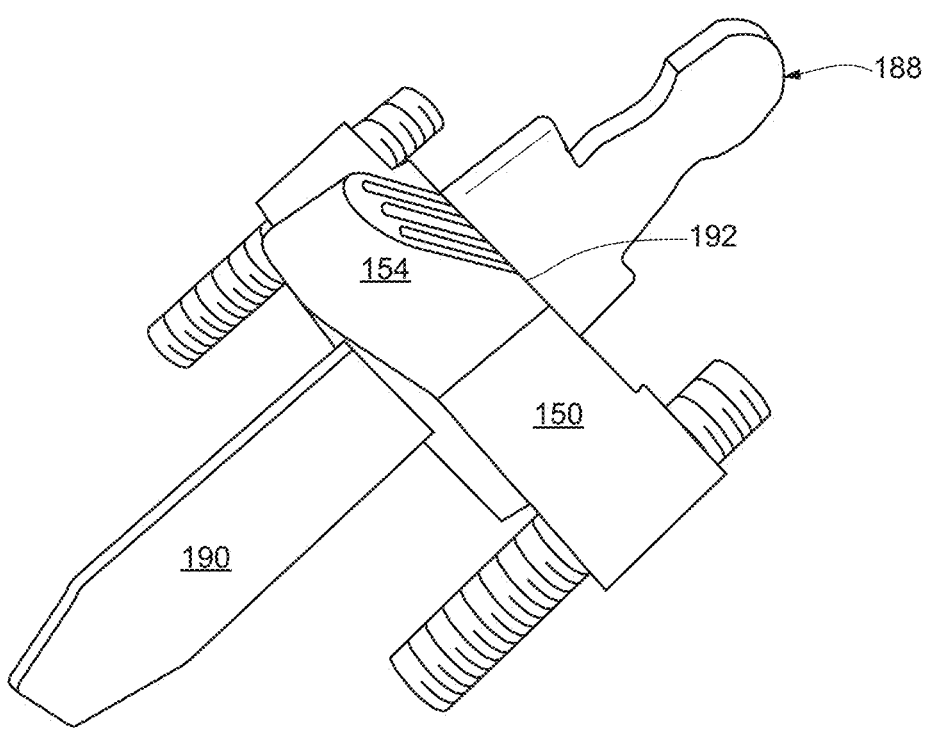
FIG. 7 is a perspective view of a bone preparing guide engaged with a spacer in accordance with an embodiment of the invention.

As shown in FIGS. 6A and 7, the bone preparation guide can also include a spacer 188 extending downward from the body 154 and configured to be placed into a joint. In some embodiments, the spacer 188 is selectively engageable with the body. The spacer can have a first portion 190 configured to extend into a joint space and a second portion 192 engageable with the body 154. In the embodiment shown, the spacer can be received within opening 170, such that the spacer extends from the body in between the first and second guide surfaces. Such a spacer can be useful for positioning the body at a desired position with respect to a joint and for properly positioning the guide with respect to bones to be cut in more than one plane (e.g., three planes selected from more than one of a frontal plane, a transverse plane, and a sagittal plane). The distance between the spacer and the first guide surface can define a length of tissue removal (e.g., bone or cartilage to be cut) from a first bone, and the distance between the spacer and the second guide surface can define a length of tissue removal (e.g., bone or cartilage to be cut) from a second bone.

As shown in FIGS. 6A/B and 8, the bone preparation guide can also include a tissue removal location check member 194 engageable with the body 154 and configured to extend to a first bone and a second bone. The tissue removal location check member can have a first portion 196 configured to extend into contact with first and second bones and a second portion 198 engageable with the body. In the embodiments shown in FIGS. 6A and 8, the tissue removal location check member extends from the body at both the first and second guiding surfaces. In other embodiments, such as the embodiment shown in FIG. 6B, separate tissue removal location check members are provided for independent insertion into respective slots of the guide. Accordingly, embodiments of tissue removal location check members are useful for allowing a practitioner to see where a tissue removing instrument guided by the surfaces will contact the bone to be prepared.

Embodiments of the bone preparation guide can be useful in operation for guiding a preparation of a bone or bones at a targeted anatomy. Bone preparation can be useful, for instance, to facilitate contact between leading edges of adjacent bones, separated by a joint, or different portions of a single bone, separated by a fracture, such as in a bone alignment and/or fusion procedure. A bone may be prepared using one or more bone preparation techniques. In some applications, a bone is prepared by cutting the bone. The bone may be cut transversely to establish a new bone end facing an opposing bone portion. Additionally or alternatively, the bone may be prepared by morselizing an end of the bone. The bone end can be morselized using any suitable tool, such as a rotary bur, osteotome, or drill. The bone end may be morselized by masticating, fenestrating, crushing, pulping, and/or breaking the bone end into smaller bits to facilitate deformable contact with an opposing bone portion.

Embodiments of the present invention also include methods for temporarily fixing an orientation of a bone or bones, for example, prior to or in conjunction with permanently fixing the orientation of the bone or bones. In general, the method of positioning a bone includes the steps of moving a bone from an anatomically misaligned position to an anatomically aligned position with respect to another bone and preparing an end of the moved bone and a facing end of another bone. In some embodiments, the end of at least one of the moved bone and the other bone is prepared after moving the bone into the aligned position. In certain embodiments, the bone is anatomically aligned in more than one plane with respect to another bone by applying a force to one bone at a single location, such that the bone both translates and rotates in response to the force. In certain embodiments, the moving step can be accomplished with a bone positioning device and/or the preparing step can be accomplished with a bone preparation guide, as described herein. In other embodiments, the moving step can be accomplished by a clinician physically grasping a bone, either through direct contact with the bone or indirectly (e.g., by inserting a K-wire, grasping with a tenaculum, or the like), and moving his hand to move the bone. In these applications, a fulcrum may be used to control movement of the bone, as also described herein.

Figure 10B:
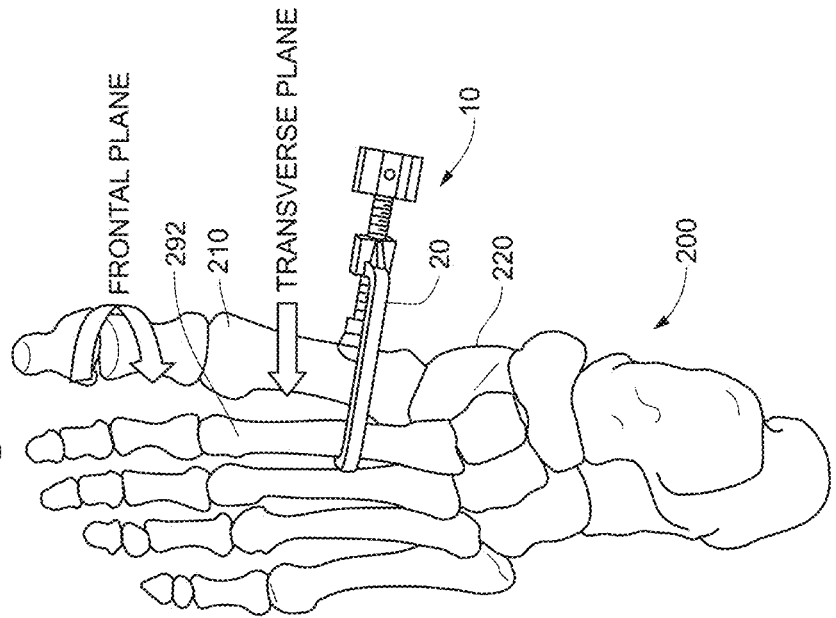
FIG. 10B is a top view of a bone positioning guide on a foot with a corrected alignment in accordance with an embodiment of the invention.
Figure 10A:
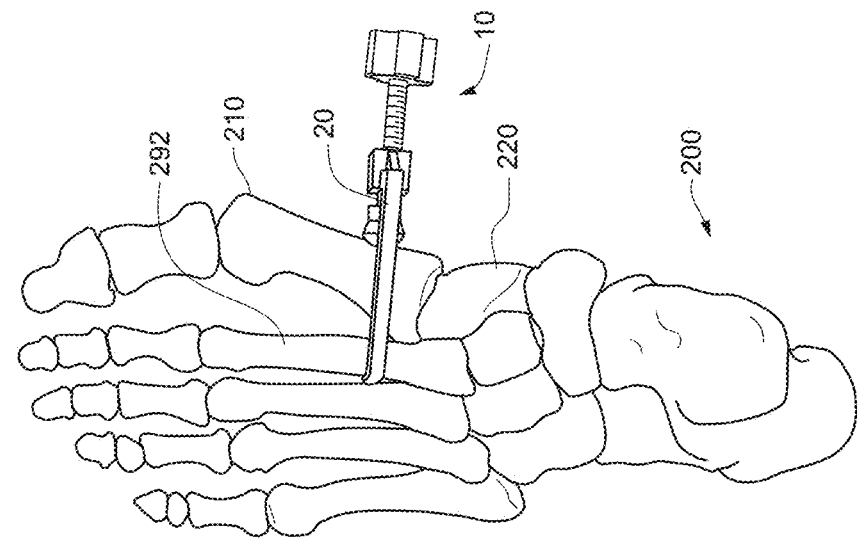
FIG. 10A is a top view of a bone positioning guide on a deformed foot in accordance with an embodiment of the invention.

FIGS. 9A-B depict fontal views of a bone positioning guide 10 on a foot 200 having a first metatarsal 210, a medial cuneiform 220, a second metatarsal 292, and a third metatarsal 294. FIG. 9A depicts a foot 200 with an uncorrected bunion deformity, while FIG. 9B depicts the foot 200 with an alignment corrected by the bone positioning guide 10. Solid line L1 represents the starting location of the bone positioning guide 10 and dotted line L2 represents the finishing location of the bone positioning guide. As shown, as the bone positioning guide 10 is actuated it rotates with the first metatarsal 210 about an axis extending through the frontal plane as it pushes the first metatarsal 210 laterally in the transverse plane and plantarly in the sagittal plane. Accordingly, in this example, the position of the first metatarsal 210 is corrected with respect to the second metatarsal 292 generally in three planes by actuating a single bone positioning guide 10 to urge a bone engagement member 40 toward a tip 50. FIG. 10A shows a top view of a foot 200 with an uncorrected bunion deformity, while FIG. 10B shows a top view of the foot 200 with an alignment corrected by the bone positioning guide 10, emphasizing the rotational correction in the frontal plane and the lateral correction in the transverse plane.

Figure 11A:
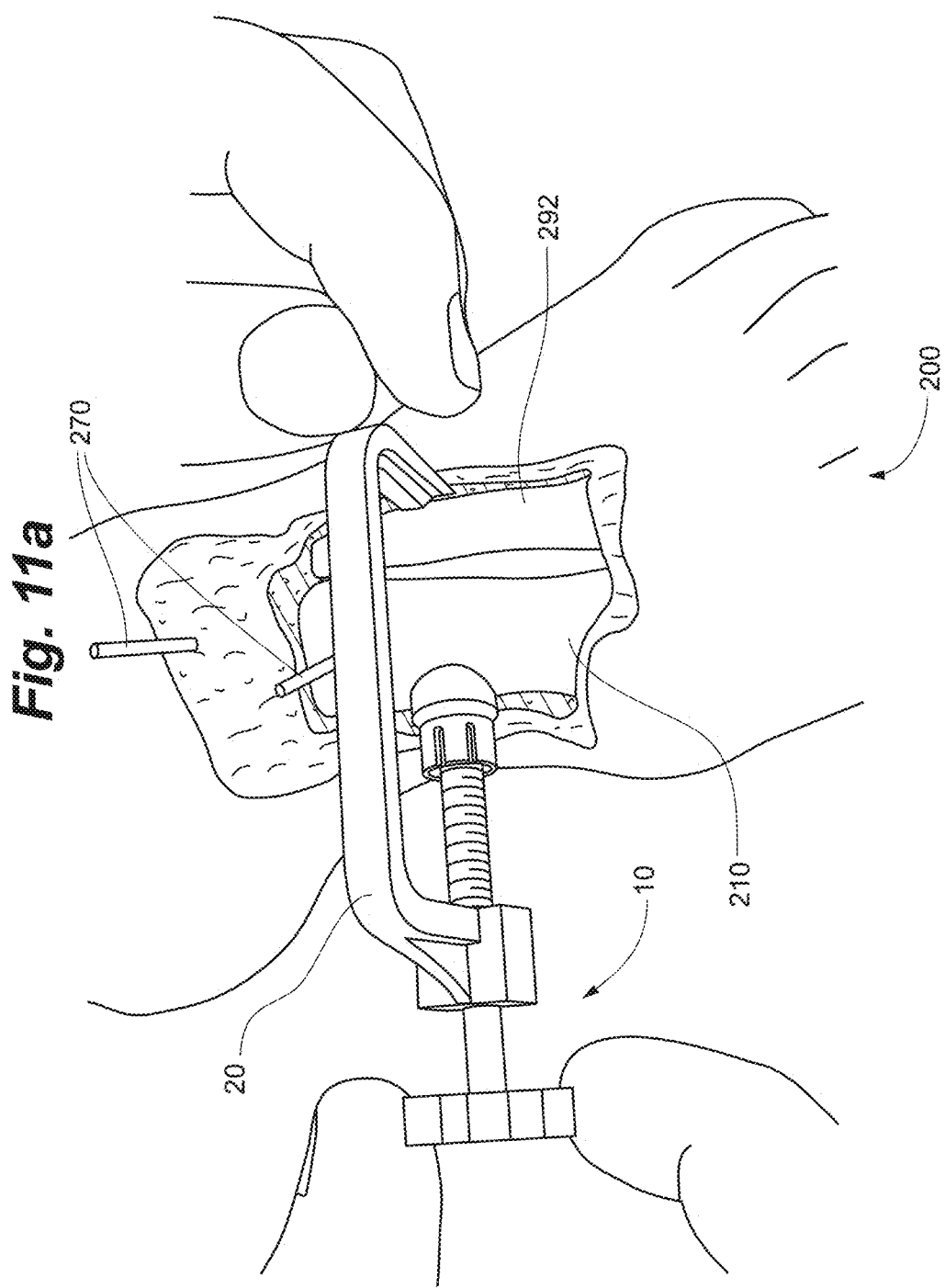
Figure 11B:
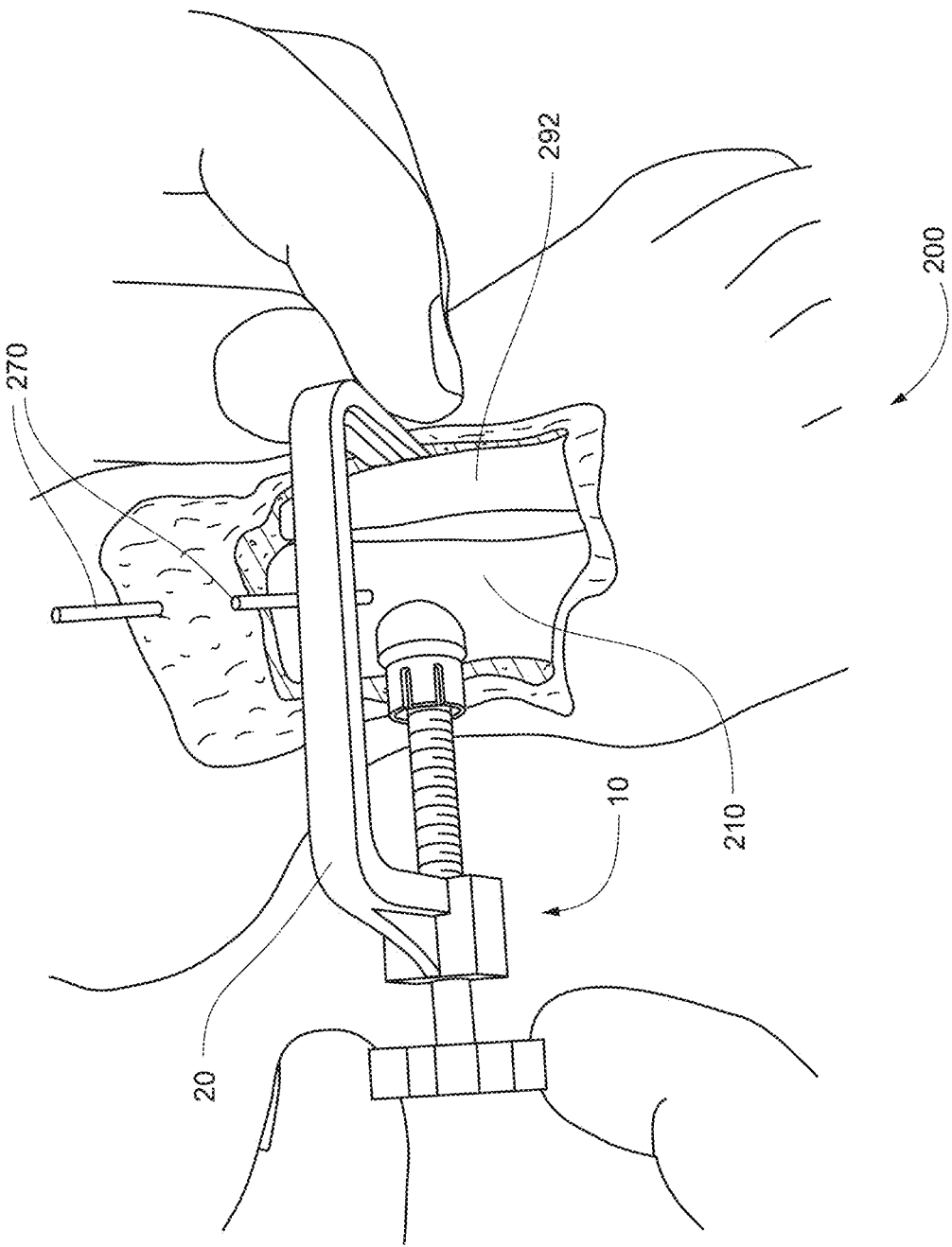

FIGS. 11A-C show three sequential images of a bone positioning guide 10 on a foot 200 positioning a first metatarsal 210 with respect to a second metatarsal 292. FIG. 11A represents the beginning of the procedure, FIG. 11B the middle, and FIG. 11C the end. The orientation of the pins 270 is useful for visualizing the amount of rotation of the first metatarsal 210 in each image. With respect to FIGS. 11A-C, it can be seen the bone positioning guide 10 and the first metatarsal 210 are rotating in the frontal plane in response to actuation of bone positioning guide 10. Further, the angle between the first metatarsal 210 and second metatarsal 292 is reduced, as the space that can be seen between the first and second metatarsals in FIG. 11A is eliminated in FIG. 11C.

Figure 12B:
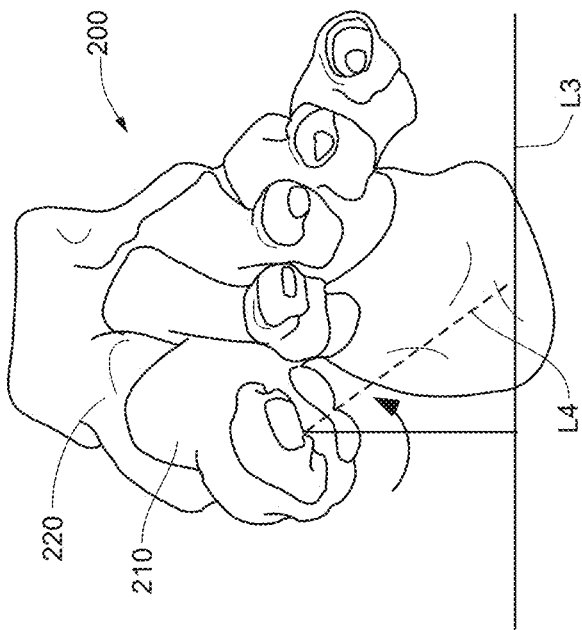
FIG. 12B is a front view of a foot with an isolated first metatarsal rotation bunion deformity.
Figure 12A:
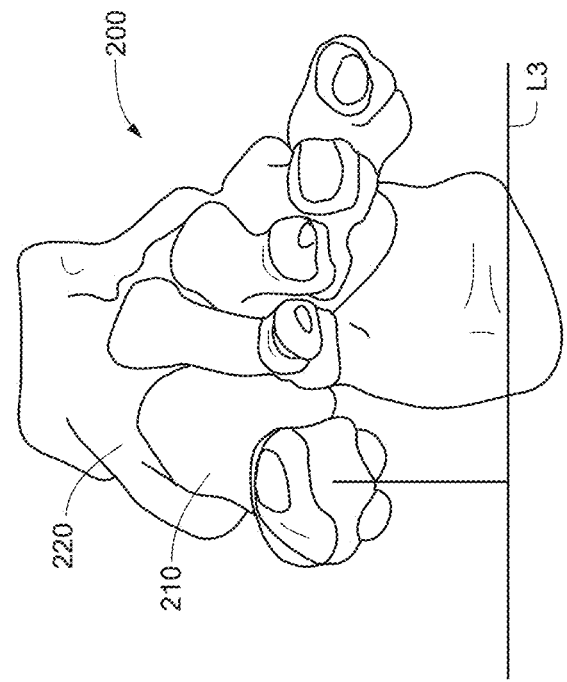
FIG. 12A is a front view of a foot with a normal first metatarsal position.

Each of the three potential planes of deformity will now be described in isolation. FIGS. 12A and 12B show frontal plane views of a foot 200. In FIG. 12A, the foot 200 is normal, while in FIG. 12B the foot is depicted with an uncorrected bunion deformity showing an isolated axial rotation of the first metatarsal 210. Solid line L3 indicates the alignment of the first metatarsal 210 relative to ground, while dotted line L4 in FIG. 12B indicates the extent of axial rotation in the frontal plane.

Figure 13B:
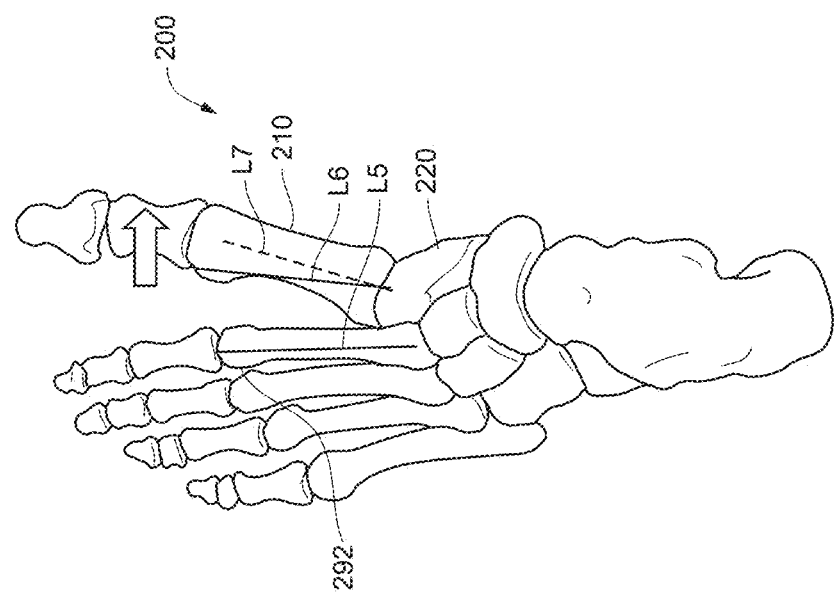
FIG. 13B is a top view of a foot with an isolated first metatarsal transverse plane bunion deformity.
Figure 13A:
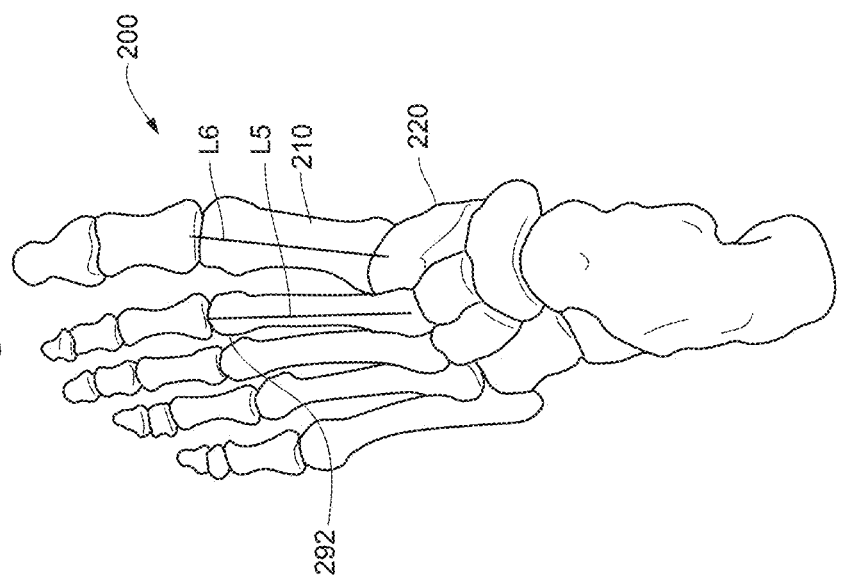
FIG. 13A is a top view of a foot with a normal first metatarsal position.

FIGS. 13A and 13B show transverse plane views of a foot 200. In FIG. 13A, the foot 200 is normal, while in FIG. 13B the foot is depicted with an uncorrected bunion deformity showing an isolated transverse plane first metatarsal 210 deviation. Solid line L5 indicates the alignment of the second metatarsal 292 and solid line L6 indicates the proper alignment of the first metatarsal 210 relative to the second metatarsal 292. The angle between these two lines forms the intermetatarsal angle (IMA). Dotted line L7 in FIG. 13B indicates the extent of transverse deviation.

Figure 14A:
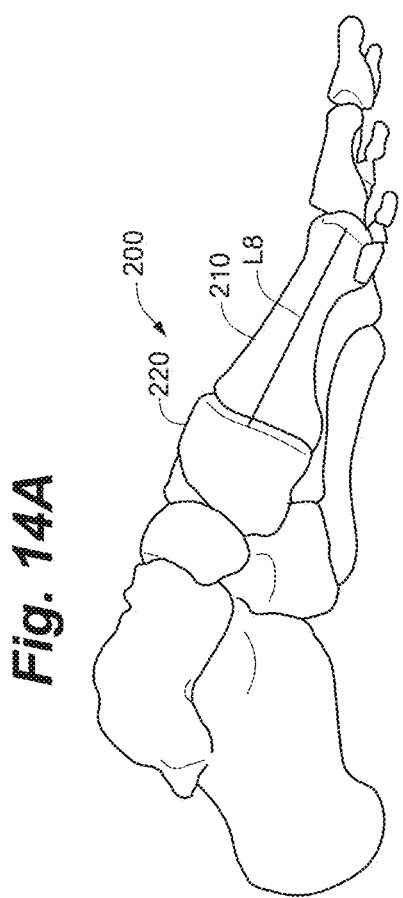
FIG. 14A is a side view of a foot with a normal first metatarsal position.
Figure 14B:
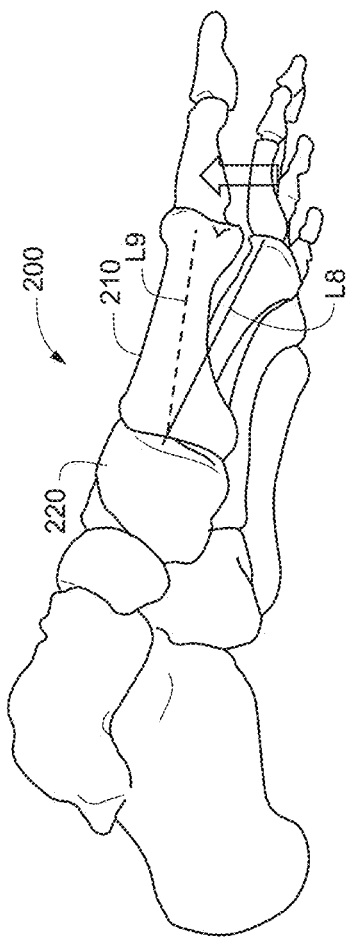
FIG. 14B is a side view of a foot with an isolated first metatarsal sagittal plane bunion deformity.

FIGS. 14A and 14B show sagittal plane views of a foot 200. In FIG. 14A, the foot 200 is normal, while in FIG. 14B the foot is depicted with an uncorrected bunion deformity showing an isolated sagittal deviation of the first metatarsal 210. Solid line L8 indicates the proper alignment of the first metatarsal 210, while dotted line L9 in FIG. 14B indicates the extent of sagittal deviation.

A specific embodiment of a method in accordance with an embodiment of the invention includes the steps of engaging a bone engagement member with a first bone, placing a tip of the bone positioning guide in apposition to a second bone, the second bone being different from the first bone, and moving the bone engagement member with respect to the tip to change the position of the first bone with respect to the second bone in more than one plane. In some embodiments, after alignment, at least one of an end of the first bone and a facing end of a third bone are prepared (e.g., only the end of the first bone or both the end of the first bone and the end of the second bone), optionally using a preparation guide.

Figure 15B:
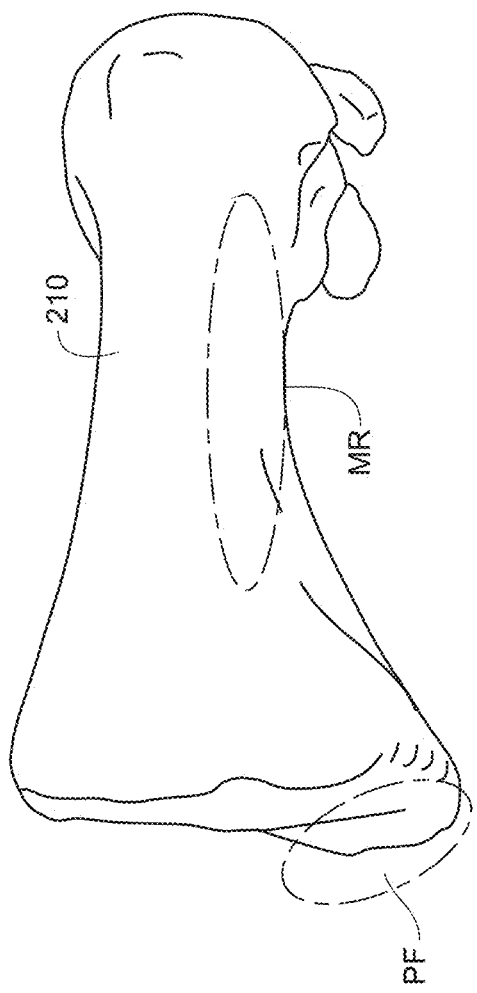
FIG. 15B is a perspective view of a first metatarsal.

In some embodiments, the method includes the step of mobilizing a joint for a corrective procedure. For example, after creating surgical access to the joint and before moving the bones into an aligned position, tissue can be released to allow a bone, such as a metatarsal, to rotate freely. In some embodiments, obstructing bone may be excised (e.g., a dorsolateral flare of the metatarsal base, a plantar flare of the metatarsal base (sometimes referred to as a plantar condyle), part of an end of a metatarsal facing a cuneiform, or osteophyte) to further promote free rotation by creating relatively flat surfaces with respect to a frontal plane. An example of a dorsolateral flare F on a first metatarsal 210 of a foot 200 is shown in FIG. 15A. An example of a plantar flare PF on a first metatarsal 210 is shown in FIG. 15B. FIG. 15B also depicts a medial ridge MR, which, in some embodiments, can be engaged by the bone engaging member of a bone positioning guide.

Embodiments of methods in accordance with the invention can also include steps performed after preparing the ends of the bones. For example, the ends of the bones may be placed in apposition and optionally compressed together and the position of the bones can be fixed with one or more bone fixation devices (e.g., compressing bone screw, bone plate, bone staple, external fixator, intramedullary implant or nail) prior to a closing of the surgical access to the joint.

An exemplary method will now be described with respect to FIGS. 16-27 depicting a foot 200 having a first metatarsal 210, a medial cuneiform 220, and a second metatarsal 292. Note, unless otherwise indicated, the steps described need not be carried out in the order described.

After customary surgical preparation and access, a bone preparation instrument 296 can be inserted into the joint (e.g., first tarsal-metatarsal joint) to release soft tissues and/or excise the plantar flare from the base of the first metatarsal 210, as shown in FIG. 16. Excising the plantar flare may involve cutting plantar flare off the first metatarsal 210 so the face of the first metatarsal is generally planar. This step helps to mobilize the joint to facilitate a deformity correction. In some embodiments, the dorsal-lateral flare of the first metatarsal may also be excised to create space for the deformity correction (e.g., with respect to rotation of the first metatarsal). In certain embodiments, a portion of the metatarsal base facing the medial cuneiform can be removed during this mobilizing step.

Figure 17:
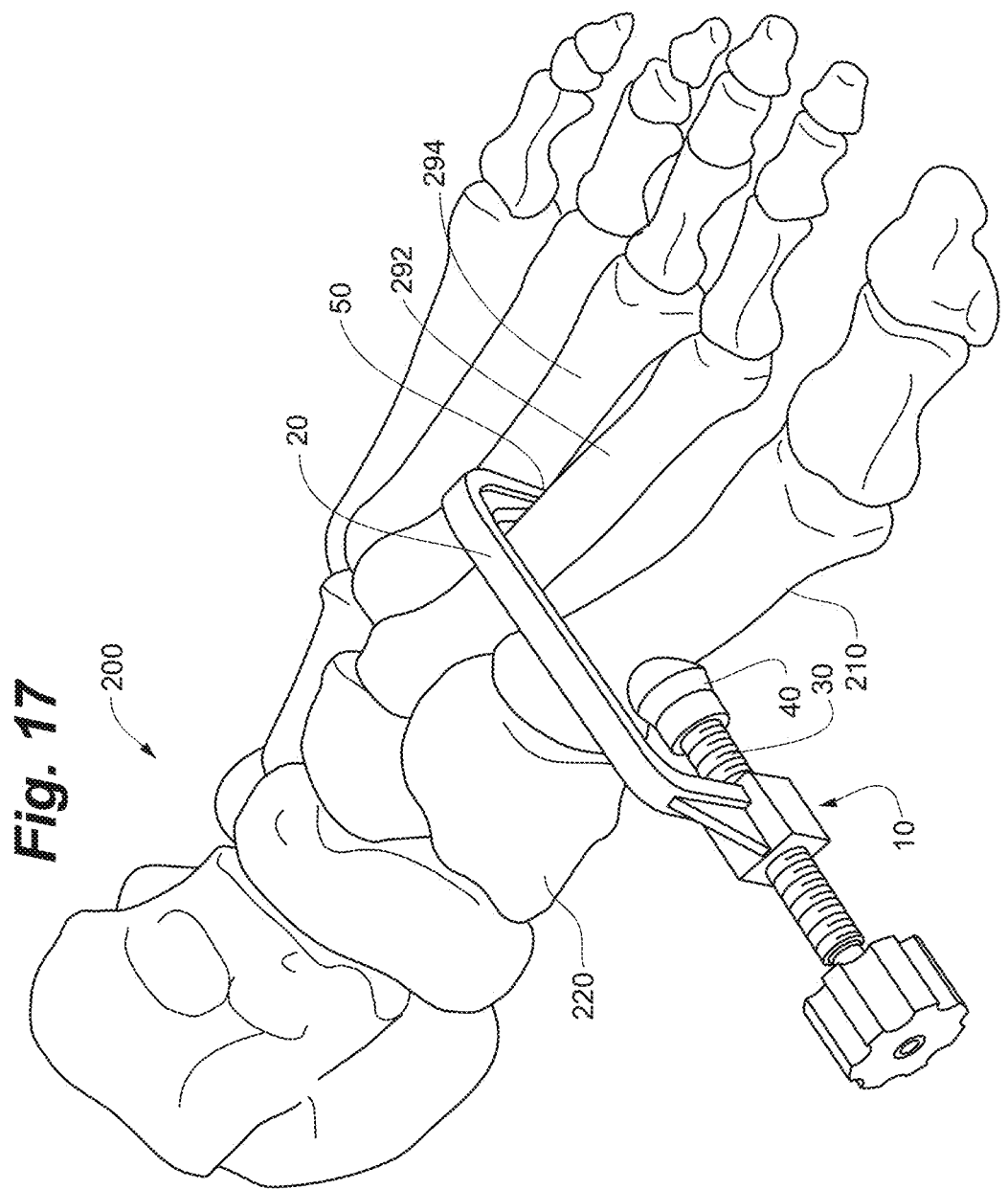
FIG. 17 is a perspective view of a foot depicting a bone positioning guide on the foot prior to an alignment of a first metatarsal.

An incision can be made and a tip 50 of a bone positioning guide 10 can be inserted on the lateral side of a metatarsal other than the first metatarsal 210, such as the second metatarsal 292. As shown in FIG. 17, the tip can be positioned proximally at a base of the second metatarsal 292 and a third metatarsal 294 interface. A surface of a bone engagement member 40 can be placed on the proximal portion of the first metatarsal 210. In some embodiments, the bone engagement member engages a medial ridge of the first metatarsal 210. As shown, the body 20 of the positioning guide can be generally perpendicular to the long axis of the second metatarsal 292.

Figure 18:
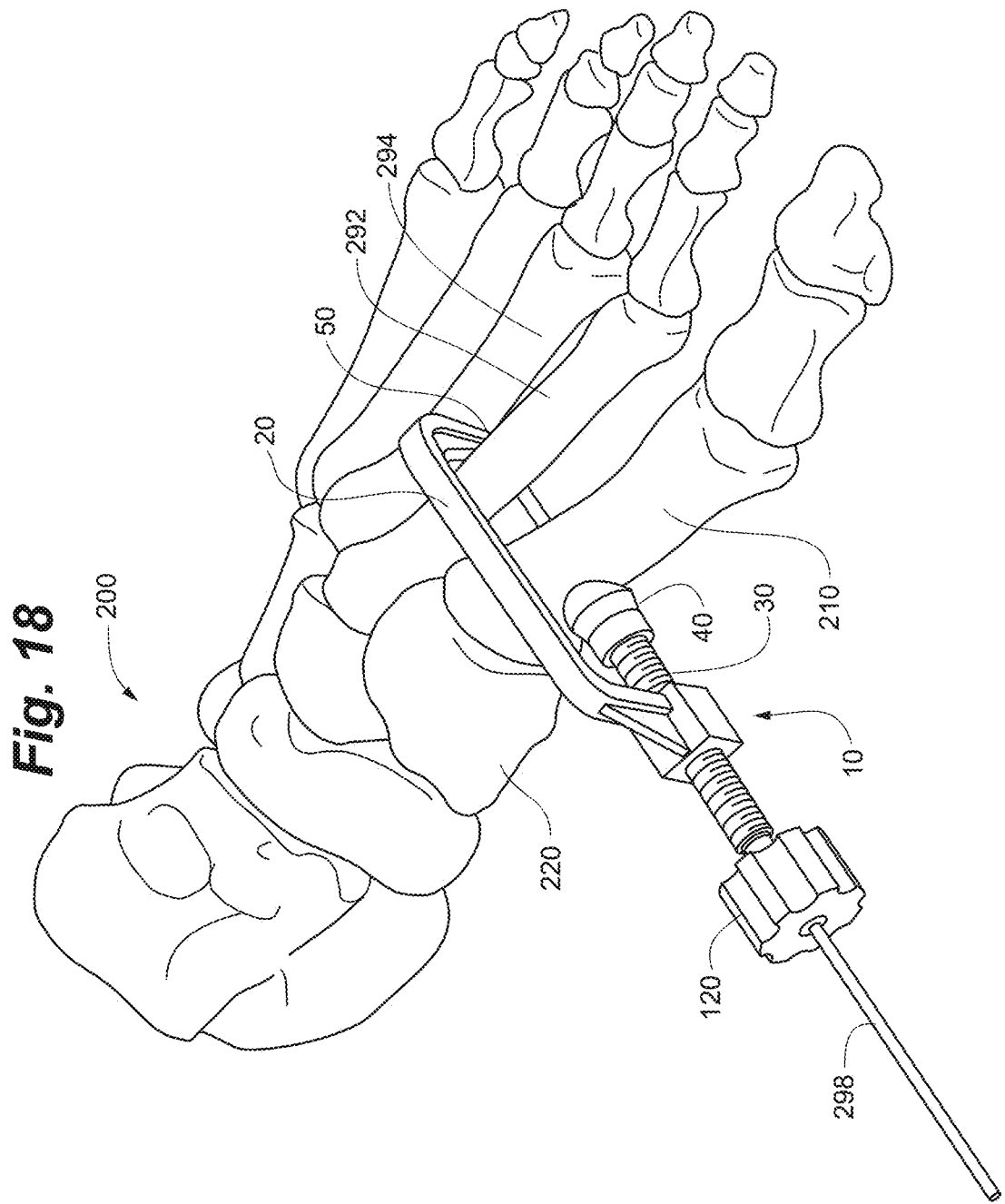
FIG. 18 is a perspective view of a foot depicting a bone positioning guide on the foot after an alignment of a first metatarsal.

As depicted in FIG. 18, the actuator 120 can be actuated to extend the shaft 30 to reduce the angle (transverse plane angle between the first metatarsal and the second metatarsal) and rotate the first metatarsal about its axis (frontal plane axial rotation). The first metatarsal 210 can be properly positioned with respect to the medial cuneiform 220 by moving the bone engagement member 40 with respect to the tip 50. In some embodiments, such movement simultaneously pivots the first metatarsal with respect to the cuneiform and rotates the first metatarsal about its longitudinal axis into an anatomically correct position to correct a transverse plane deformity and a frontal plane deformity. In certain embodiments, body 20 rotates in a generally lateral direction during this step. In some embodiments, fixation pins (not shown in FIG. 18) can be inserted into the bones prior to the positioning step (e.g., freehand or using apertures in the guide as a template), and can be used to impart additional force (transverse, sagittal, and/or frontal plane rotational) to the first metatarsal 210, if desired. The bone positioning guide 10 can hold the desired position of the first metatarsal 210 with respect to the second metatarsal 292. After the desired correction is achieved, a fixation wire 298 can be inserted through a cannulation in the shaft 30 and driven into the first metatarsal 210 and the second metatarsal 292 to hold the corrected position.

Figure 19:
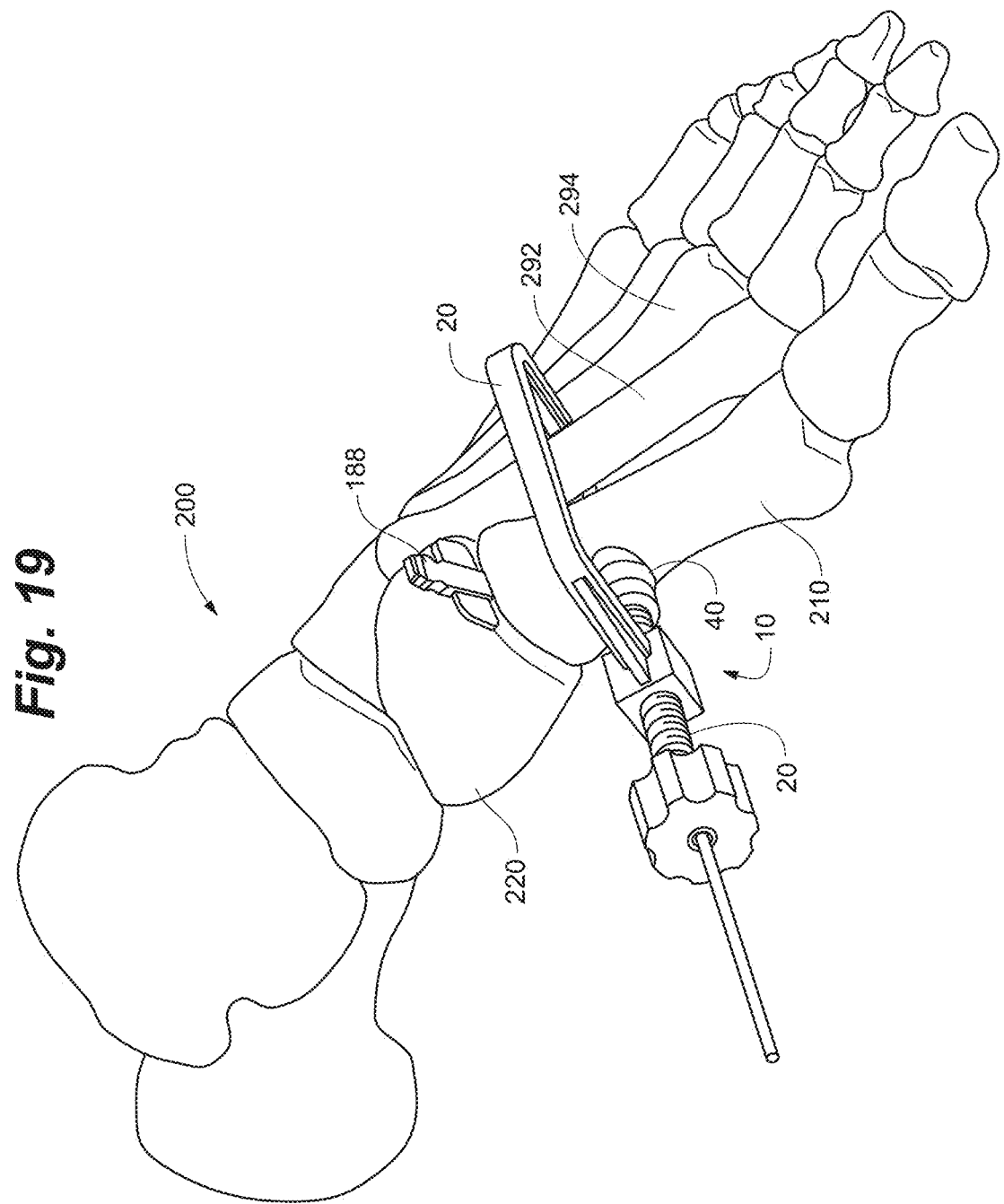
FIG. 19 is a perspective view of a foot depicting a bone positioning guide on the foot after an alignment of a first metatarsal and an insertion of a spacer into a joint space.

As depicted in FIG. 19, a joint spacer 188 can be positioned within the joint between the first metatarsal and the medial cuneiform.

Figure 20:
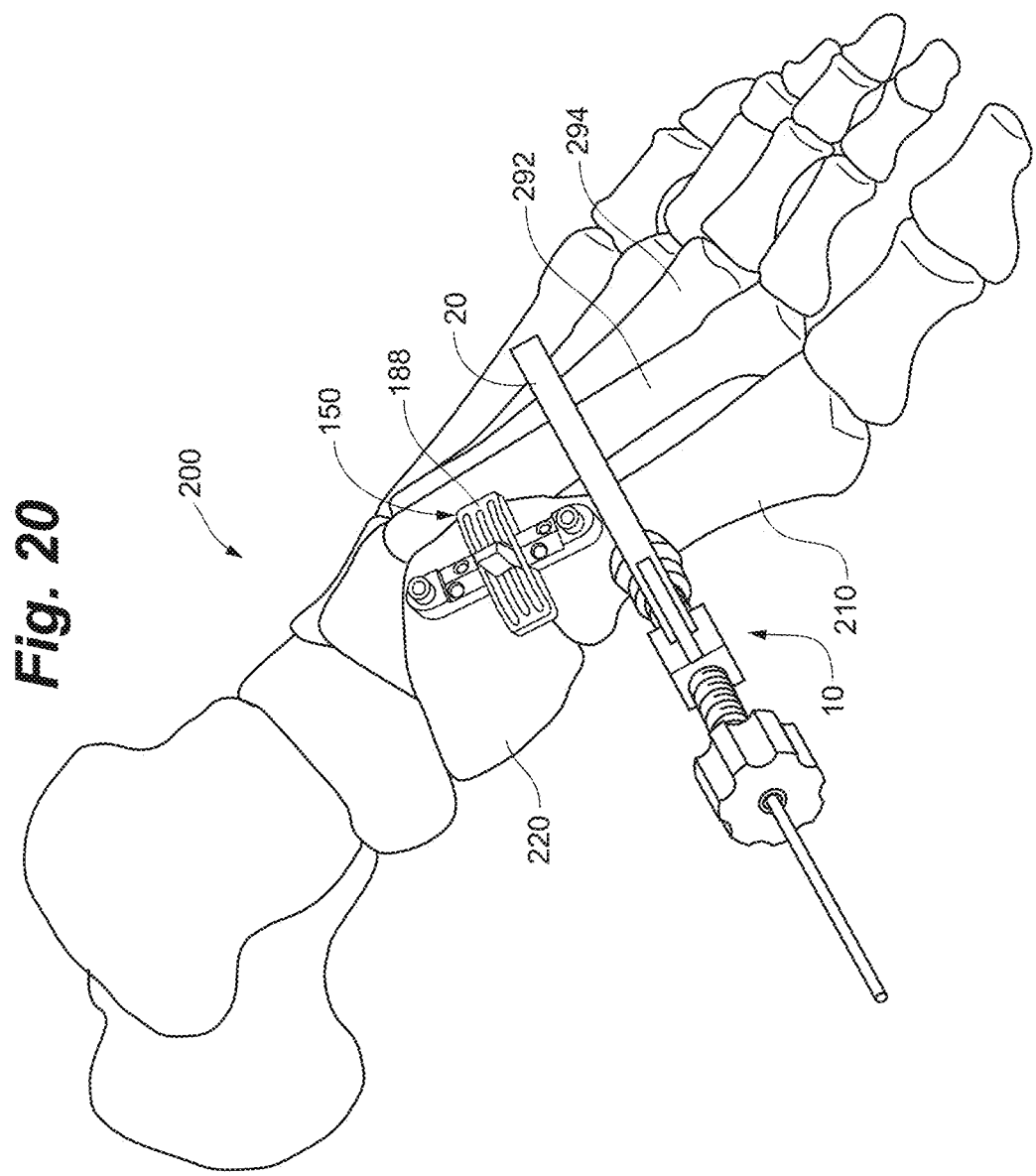
FIG. 20 is a perspective view of a foot depicting a bone positioning guide on the foot after an alignment of a first metatarsal and a positioning of a bone preparation guide.

As shown in FIG. 20, a bone preparation guide 150 can be placed over the joint spacer 188 and engaged with the joint spacer to set a position and orientation of the bone preparation guide relative to the joint. As shown, the bone preparation guide 150 can be positioned proximal to the bone positioning guide 10 in longitudinal alignment with the long axis of the first metatarsal 210 and the medial cuneiform 220, generally on the dorsal or dorsal-medial surface. In other embodiments, the spacer 188 is positioned after the guide 150 is provisionally placed on the bones. In yet other embodiments, bone preparation guide 150 and joint spacer 188 are placed simultaneously. In still other embodiments, bone preparation guide 150 is placed on the bones without using joint spacer 188 to aid with positioning.

Figure 21A:
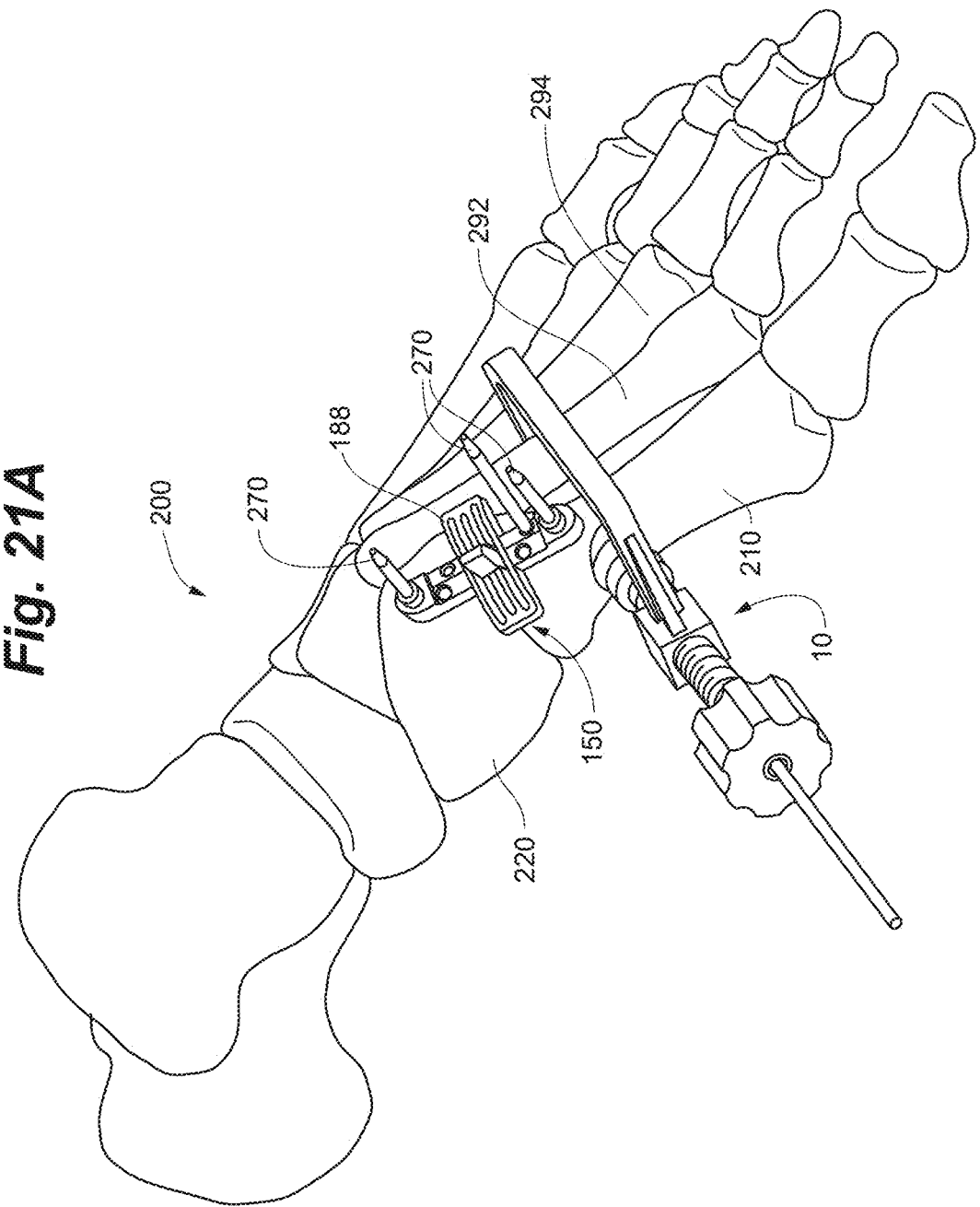
FIG. 21A is a perspective view of a foot depicting a bone positioning guide on the foot after an alignment of a first metatarsal and a positioning of a bone preparation guide with pins.

As depicted in FIGS. 21A and 21B, one or more fixation pins 270 can be inserted into apertures of the bone preparation guide 150 to secure the guide to the first metatarsal 210 and the medial cuneiform 220. As shown, some pins 270 can be inserted at an angle or in a converging orientation to help prevent movement of the bone preparation guide 150 during a tissue removing step. As shown, two of the pins 270, one on the first metatarsal and one on the medial cuneiform, are parallel to allow the bone preparation guide 150 to be removed from the foot without removing all the pins. After insertion of the pins 270, the spacer 188 can optionally be removed in embodiments having a selectively engageable spacer (e.g., a joint spacer 188 that is physically removable from bone preparation guide 150).

In some embodiments, the location of the intersection of the tissue removing instrument and the bone to be prepared is confirmed before bone preparation. In one embodiment, a tissue removing instrument location check member can be engaged with the preparation guide to visually confirm where a tissue removal instrument will contact the bone. In another embodiment, a tissue removal instrument is engaged with the preparation guide to visually confirm where the instrument will contact the bone. In either embodiment, such visual confirmation can include the use of an imaging device, such as an X-ray. If the position of the preparation guide is correct, additional fixation pins may be inserted through the apertures (e.g., angled apertures) to further fix the position of the preparation guide with respect to the first metatarsal and the medial cuneiform. In some embodiments, the spacer is reattached prior to further bone preparation steps.

In some embodiments, the end of the first metatarsal 210 facing the medial cuneiform 220 can be prepared with a tissue removing instrument 296 guided by a guide surface of bone preparation guide 150 (e.g., inserted through a slot defined by a first guide surface and a first facing surface). Additionally or alternatively, the end of the first metatarsal 210 facing the medial cuneiform 220 can be prepared by morselizing the end of the first metatarsal. In some embodiments, the first metatarsal 210 end preparation is done after the alignment of the bones, e.g., by actuating bone positioning guide 10 before preparing the end of first metatarsal 210. In other embodiments, the first metatarsal 210 end preparation is done before the alignment of the bones, e.g., by preparing the end of the first metatarsal 210 before actuating bone positioning guide 10.

In addition, as shown in FIG. 22, the end of the medial cuneiform 220 facing the first metatarsal 210 can be prepared with the tissue removing instrument 296 guided by a guide surface of bone preparation guide 150 (e.g., inserted through a slot defined by a second guide surface and a second facing surface). Additionally or alternatively, the end of the medial cuneiform 220 facing the first metatarsal 210 can be prepared by morselizing the end of the medial cuneiform. In some embodiments, the medial cuneiform 220 end preparation is done after the alignment of the bones. In yet other embodiments, the medial cuneiform 220 end preparation is done before the alignment of the bones. In embodiments that include cutting bone or cartilage, the cuneiform cut and the metatarsal cut can be parallel, conforming cuts. In the specific embodiment shown in FIG. 22, a saw blade can be inserted through a first slot to cut a portion of the medial cuneiform and the saw blade can be inserted through a second slot to cut a portion of the first metatarsal (e.g., in some embodiments the medial cuneiform can be cut before the first metatarsal). Accordingly, in the embodiment shown, the cuts to both the first metatarsal and the medial cuneiform were preformed after the first metatarsal was positioned.

Figure 23:
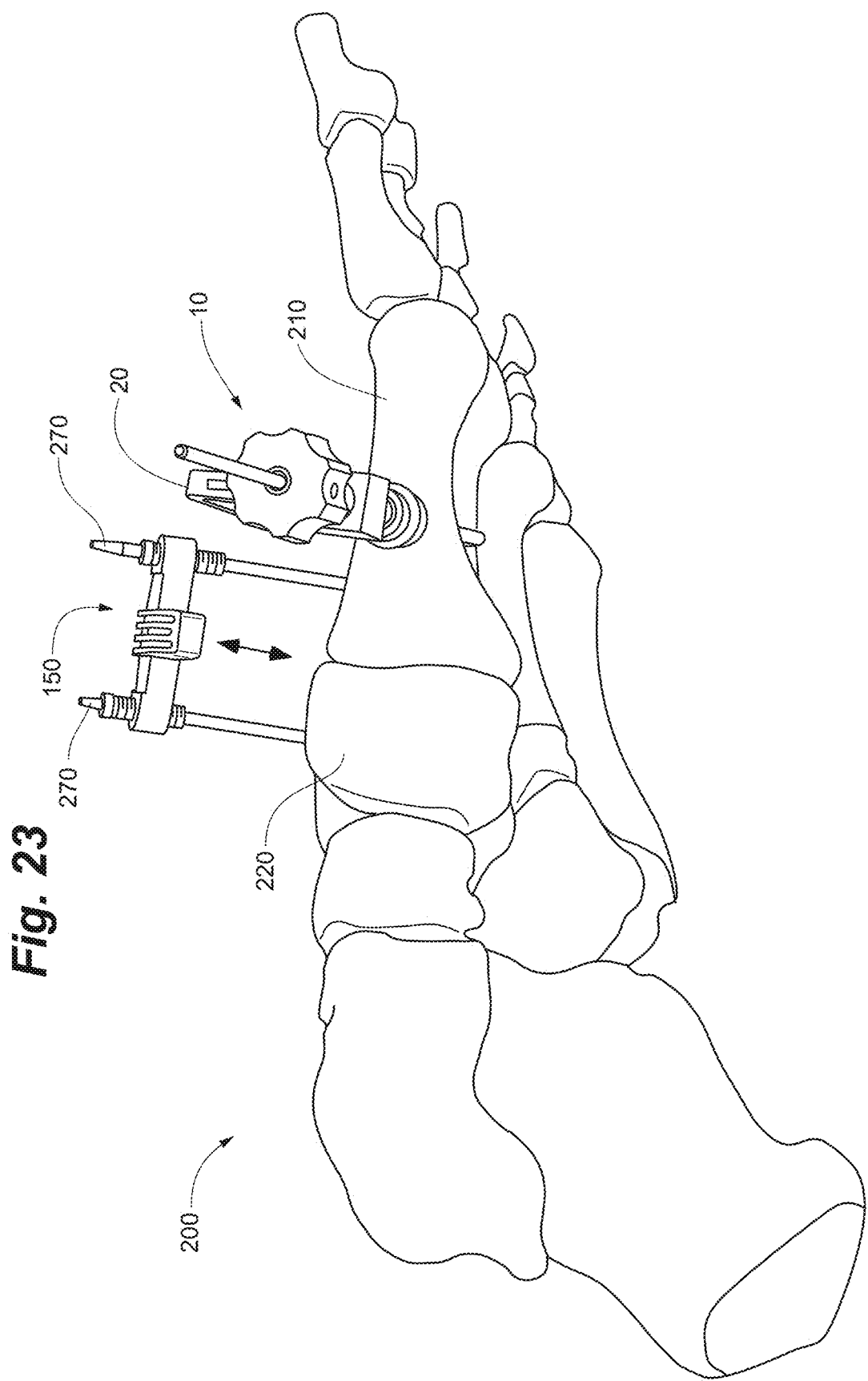
FIG. 23 is a perspective view of a foot depicting a bone positioning guide on the foot and a removal of a bone preparation guide.

Any angled/converging pins can be removed and the bone preparation guide 150 can be lifted off the parallel pins 270, as shown in FIG. 23. The parallel pins can be referred to as "reference pins" which can serve as a reference in later steps to ensure that the corrected alignment of the first metatarsal 210 has been maintained. The joint spacer can also be removed before, after, or simultaneously with the bone preparation guide. In some embodiments, the bone positioning guide 10 is also removed from the foot.

The tissue (e.g., bone or cartilage slices) from the first metatarsal and the medial cuneiform can be removed from the joint site and the joint surfaces can be fenestrated, if desired. If the bone positioning guide was taken off the foot, it can be put back on, as shown in FIG. 24, before the additional steps discussed below.

After preparation, the ends of the two bones can be placed in apposition and optionally compressed together by provisionally fixating the joint. For example, the two bones may be placed in apposition by placing the cut and/or morselized end of the first metatarsal 210 in abutment with the cut and/or morselized end of the medial cuneiform 220. In some examples, the cut and/or morselized end of the first metatarsal 210 is placed adjacent to, and optionally in contact with, the cut and/or morselized end of the medial cuneiform 220.

As shown in FIG. 25, a compression pin, such as a threaded olive pin 300 can be inserted through the first metatarsal 210 and into the medial cuneiform 220 to provide compression and provisional fixation between the first metatarsal and the medial cuneiform. Additional compression pins can be inserted to provide additional stability. As shown, the parallel reference pins should be aligned during this step. In some embodiments, a practitioner checks for alignment of the parallel reference pins prior to insertion of the compression pin, and, if they are not aligned, adjusts the position of the first metatarsal until desired alignment is achieved.

Figure 26A:
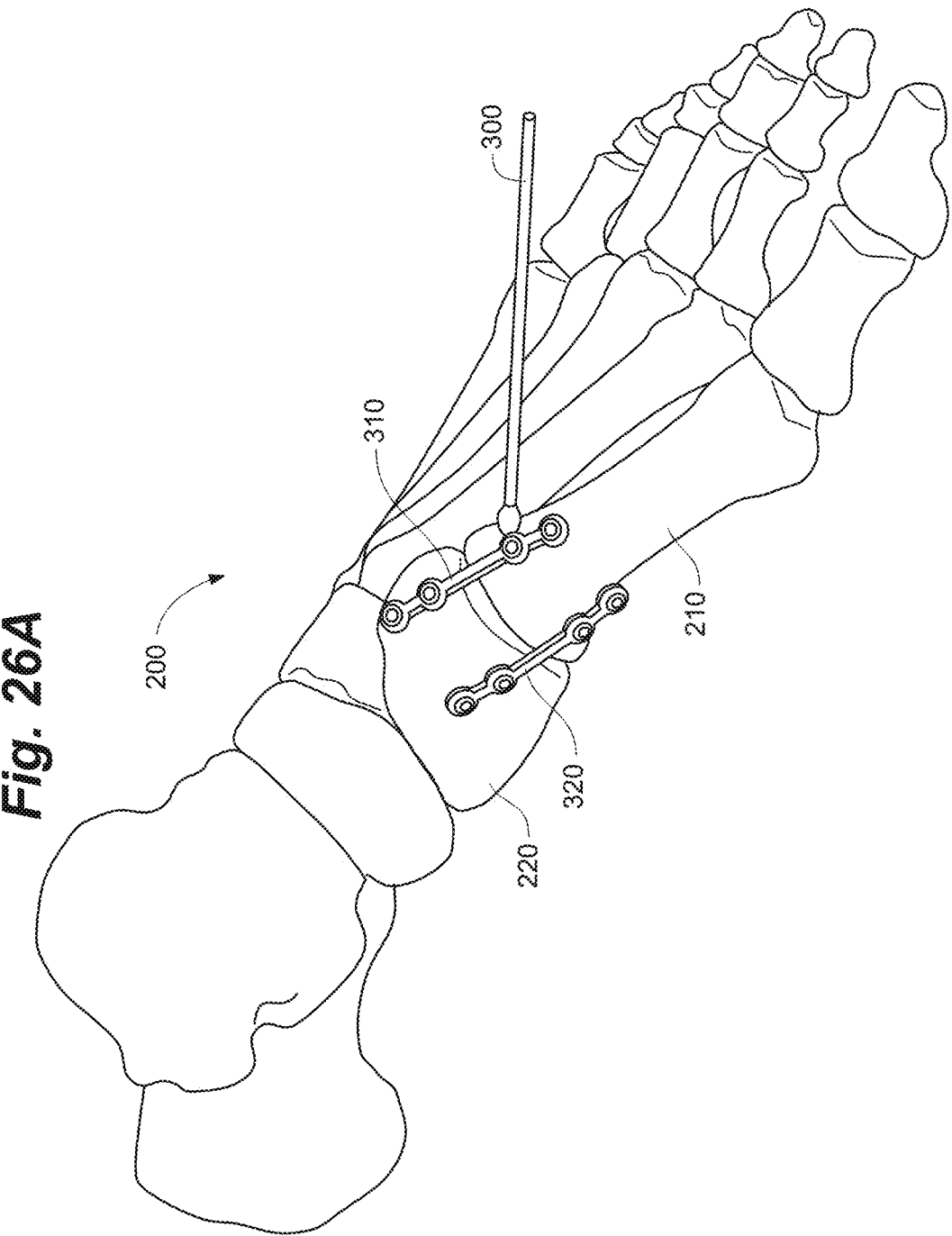
FIG. 26A is a side perspective view of a foot depicting bone plates across a joint between first and second bones and a compression pin in accordance with an embodiment of the invention.
Figure 26B:
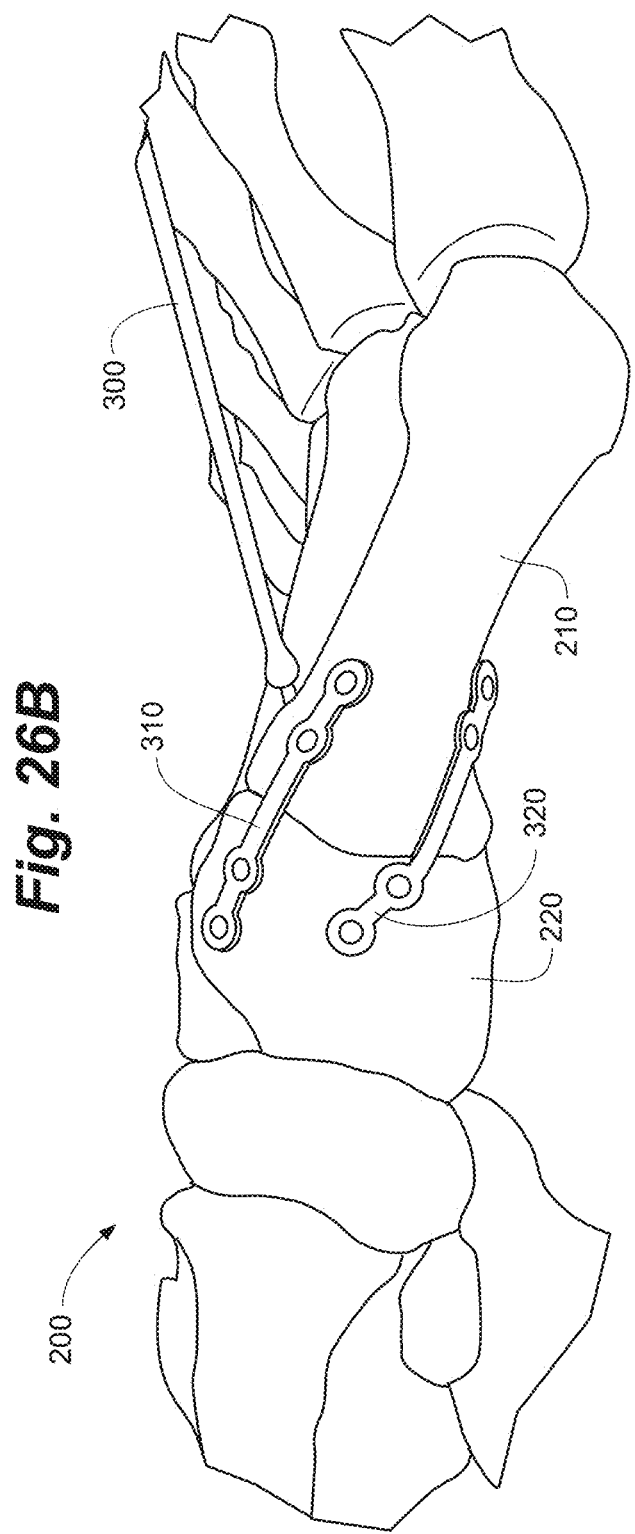
FIG. 26B is a side perspective view of a foot depicting bone plates across a joint between first and second bones and a compression pin in accordance with an embodiment of the invention.

Although they can be left in place, in some embodiments the parallel reference pins and bone positioning guide can be removed and a bone fixation device (e.g., two bone plates positioned in different planes, as shown) can be applied to stabilize the joint for fusion. FIG. 26A shows a first bone plate 310 positioned on a dorsal-medial side of the first metatarsal and medial cuneiform and a second bone plate 320 positioned on a medial-plantar side of the first metatarsal and the medial cuneiform. In other embodiments, such as the embodiment shown in FIG. 26B, the second bone plate 320 can be a helical bone plate positioned from a medial side of the cuneiform to a plantar side of the first metatarsal across the joint space. The plates can be applied with the insertion of bone screws. Example bone plates that can be used as first bone plate 310 and/or second bone plate 320 are described in US Patent Publication No. US2016/0192970, titled "Bone Plating System and Method" and filed Jan. 7, 2016, which is incorporated herein by reference.

Figure 27:
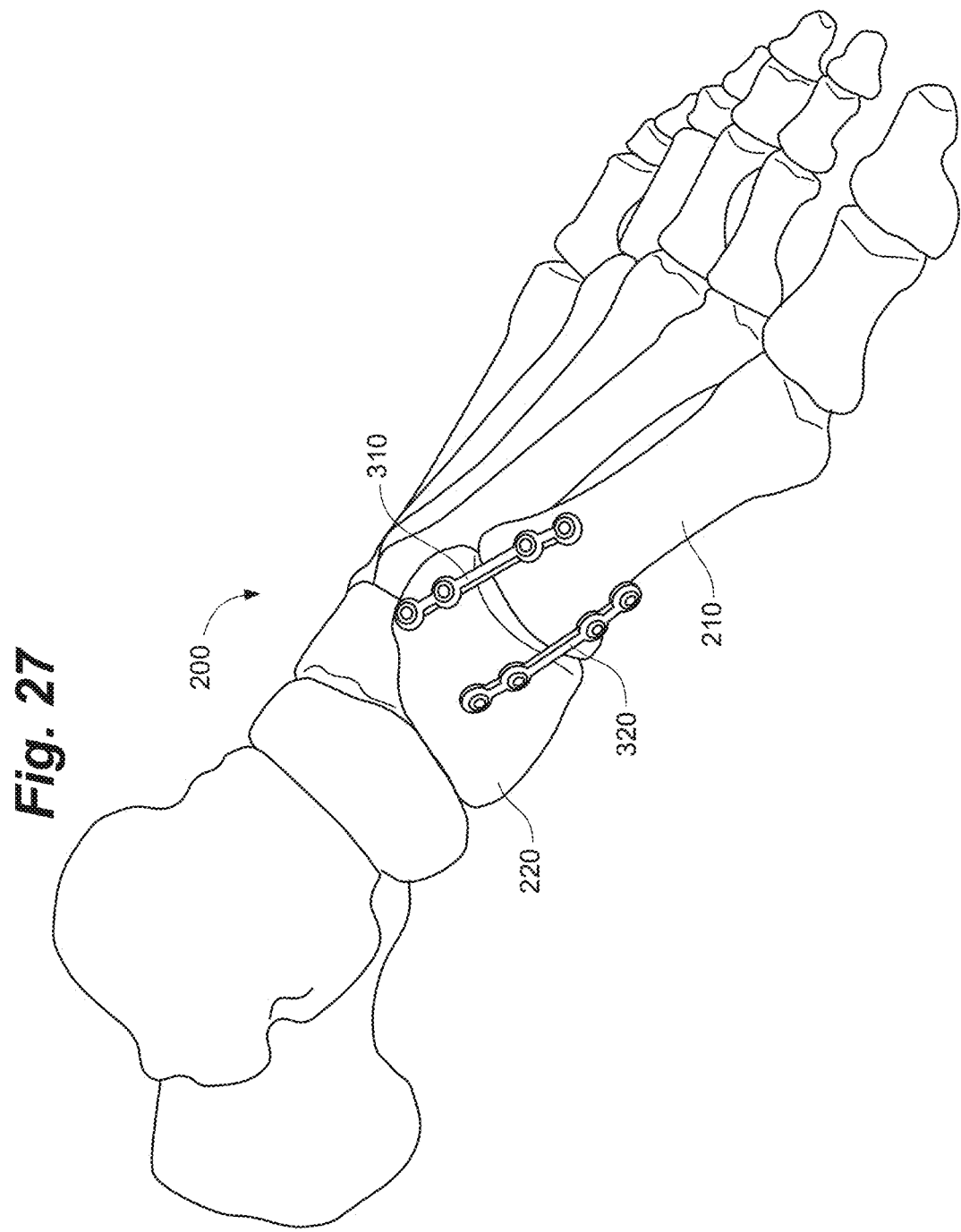
FIG. 27 is a side perspective view of a foot depicting bone plates across a joint between first and second bones in accordance with an embodiment of the invention.

As shown in FIG. 27, the compression pin can be removed and the incision can be closed.

Figure 28B:
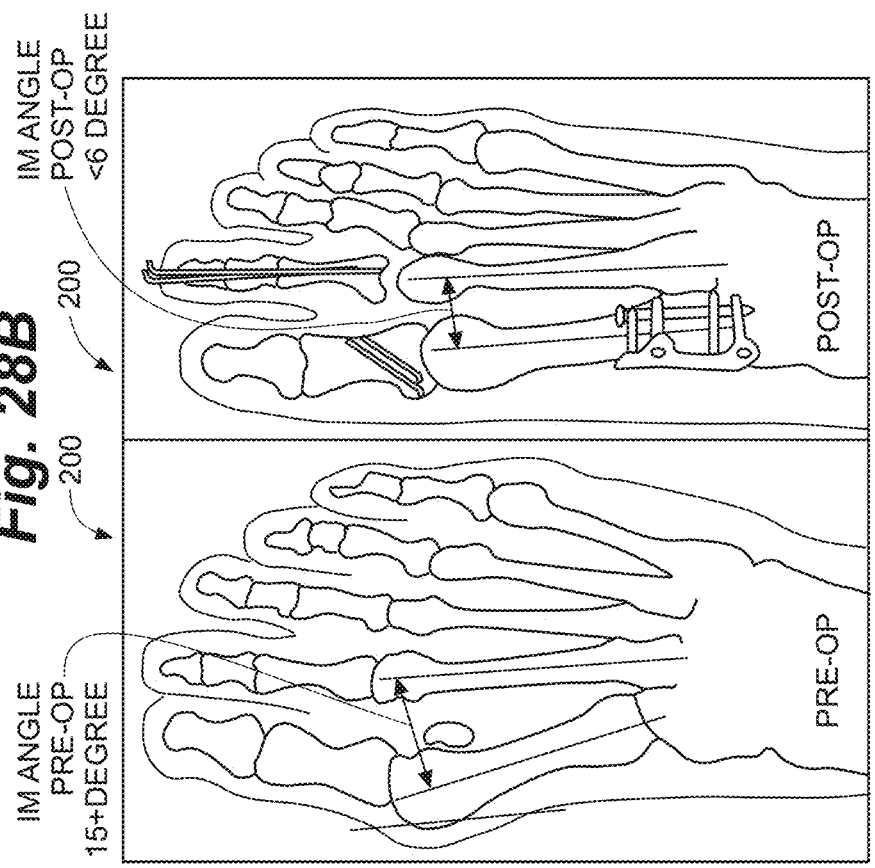
FIG. 28A and FIG. 28B depict examples of anatomically misaligned metatarsals and metatarsals that have been anatomically aligned using methods and/or instruments in accordance with the invention.
Figure 28A:
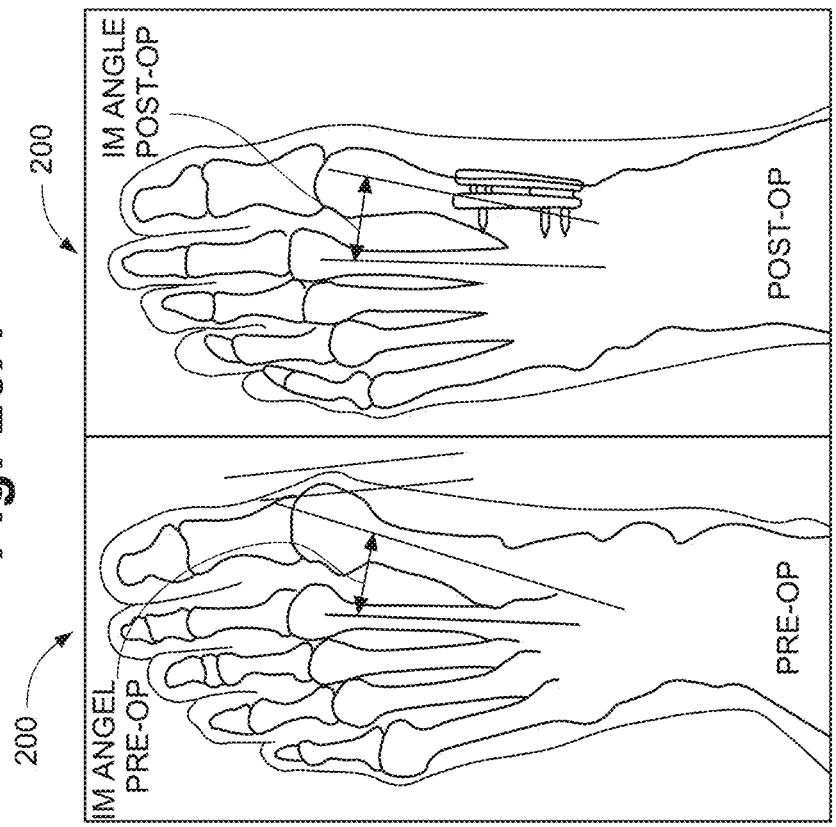
Figure 29B:
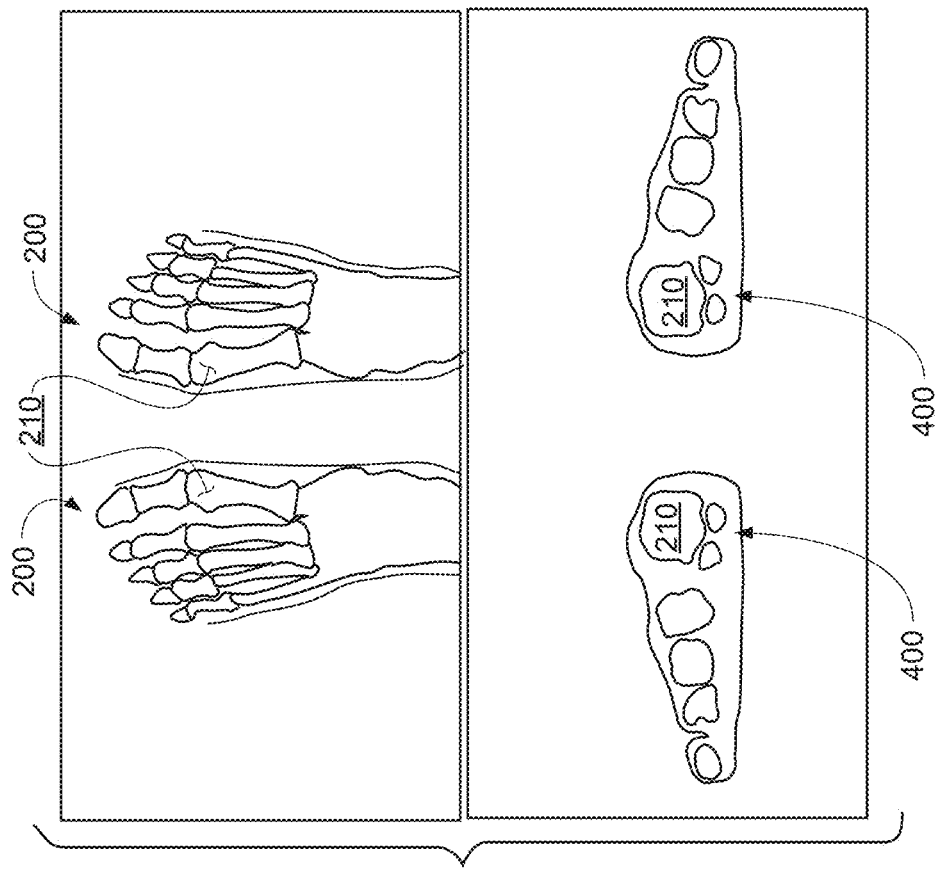
FIG. 29A and FIG. 29B depict examples of anatomically misaligned metatarsals and metatarsals that have been anatomically aligned using methods and/or instruments in accordance with the invention.
Figure 29A:
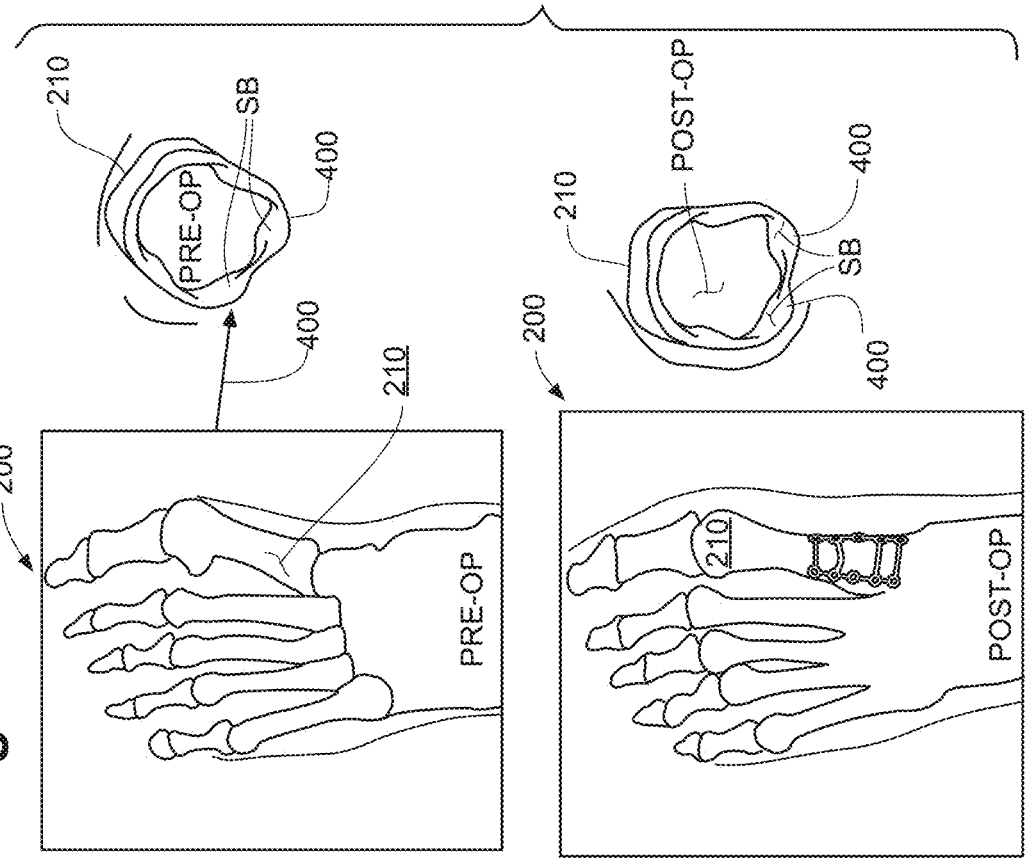

FIGS. 28A/B and 29A/B include examples of anatomically misaligned metatarsals and metatarsals that have been anatomically aligned using methods and/or instruments in accordance with the invention. FIG. 28A shows a left foot pre-operation and post-operation, while FIG. 28B shows a right foot pre-operation and post-operation. As can be seen from a comparison of the pre-operative images to the post-operative images, the patients' intermetatarsal angle (IMA) was significantly reduced. FIGS. 29A and 29B show the correction of an axial rotation in a frontal rotational plane. FIG. 29A shows a pre-operative image and a post-operative image of a right foot. Drawings of a metatarsal 210 are also provided to illustrate the rotation. The rotation of the metatarsal can be seen by the position of sesamoid bones 400, which are depicted as having been rotated under the first metatarsal 210 in the post-operative drawing. FIG. 29B shows pre-operative views of a left foot 200 and a right foot 200. Again, by comparing the location of the sesamoid bones 400 with respect to a reference location, such as ground, the planter surface of the foot, and/or a cuneiform, it can be seen this patient's metatarsal is rotated out of alignment.

Methods in accordance with embodiments of the invention can be useful for positioning a bone or bones. Bone positioning can be useful, for instance, to correct an anatomical misalignment of bones and maintain an anatomically aligned position, such as in a bone alignment and/or fusion procedure. In some embodiments, an "anatomically aligned position" means that an angle of a long axis of a first metatarsal relative to a long axis of a second metatarsal is about 10 degrees or less in the transverse plane or sagittal plane. In certain embodiments, anatomical misalignment can be corrected in both the transverse plane and the frontal plane. In the transverse plane, a normal intermetatarsal angle ("IMA") between a first metatarsal and a second metatarsal may be less than about 9 degrees (e.g., less than 6 degrees). An IMA of between about 6 degrees and about 13 degrees (e.g., between about 9 degrees and about 13 degrees) may be considered a mild or moderate misalignment of the first metatarsal relative to the second metatarsal. An IMA of greater than about 16 degrees may be considered a severe misalignment of the first metatarsal relative to the second metatarsal. In some embodiments, methods in accordance with the invention are capable of anatomically aligning the bone(s) by reducing the IMA from over 10 degrees to about 10 degrees or less (e.g., to an IMA of less than 6 degrees, such as to an IMA of about 1-5 degrees), including to negative angles of about −5 degrees or until interference with the second metatarsal, by positioning the first metatarsal at a different angle with respect to the second metatarsal.

With respect to the frontal plane, a normal first metatarsal will be positioned such that its crista prominence is generally perpendicular to the ground and/or its sesamoid bones are generally parallel to the ground and positioned under the metatarsal. This position can be defined as a metatarsal rotation of 0 degrees. In a misaligned first metatarsal, the metatarsal is axially rotated between about 4 degrees to about 30 degrees or more. In some embodiments, methods in accordance with the invention are capable of anatomically aligning the metatarsal by reducing the metatarsal rotation from about 4 degrees or more to less than 4 degrees (e.g., to about 0 to 2 degrees) by rotating the metatarsal with respect to the medial cuneiform.

While various embodiments of bone positioning and preparing guide systems and methods have been described, it should be appreciated that the concepts of the disclosure can be altered in practice, e.g., based on the needs of the clinician, the patient undergoing the bone repositioning procedure, the specific anatomy being treated, and/or the target clinical outcome. As one example, the described systems and techniques may be modified to utilize a fulcrum about which rotation and/or pivoting of one bone relative to another bone occurs, e.g., with or without use of bone positioning guide 10. The fulcrum can establish and/or maintain space between adjacent bones being moved, e.g., compressed between bone engagement member 40 and tip 50 when using bone positioning guide 10, preventing lateral translation or base shift of the bones during rotation and/or pivoting.

Figure 30B:
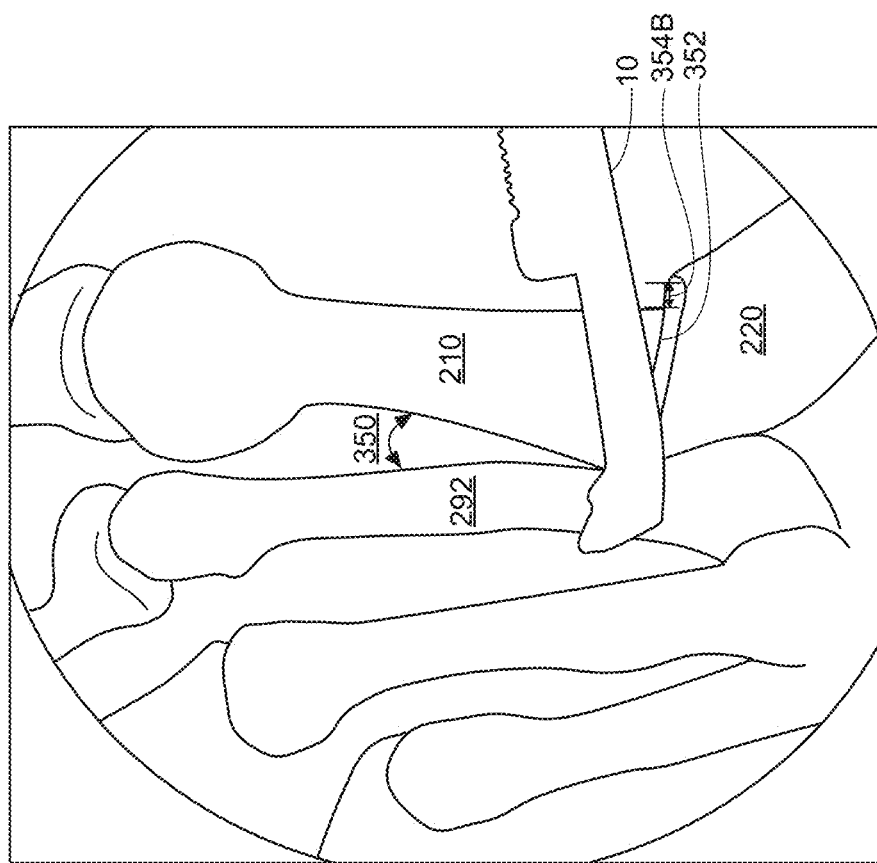
FIG. 30B shows an example base compression that can be caused after the foot of FIG. 30A is anatomically aligned.
Figure 30A:
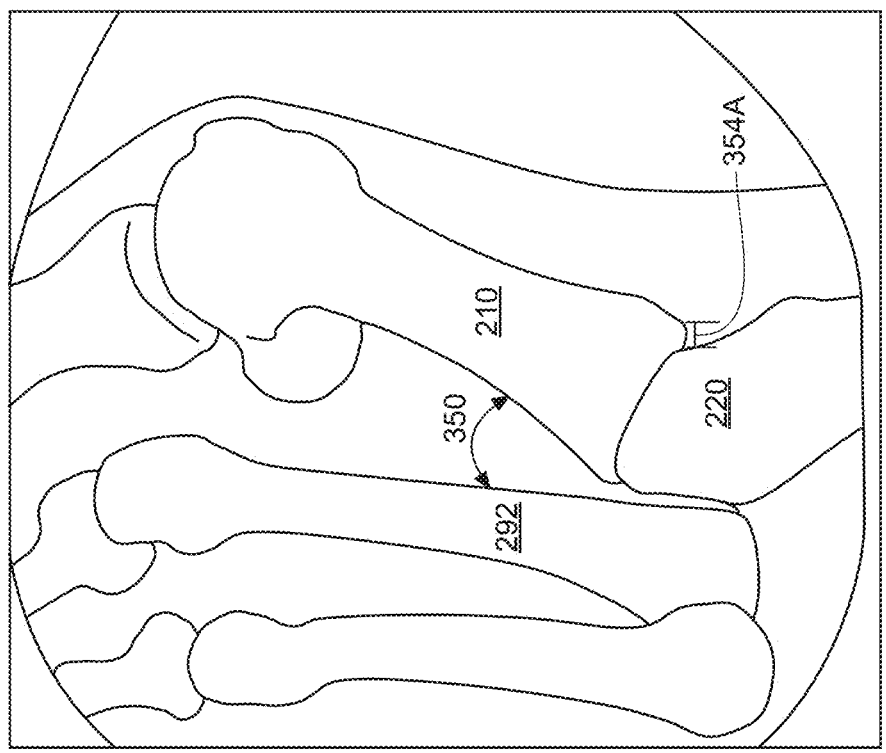
FIG. 30A illustrates a portion of a foot having a bunion caused by a misaligned first metatarsal relative to a second metatarsal.

FIG. 30A illustrates a portion of a foot having a bunion caused by a misaligned first metatarsal 210 relative to second metatarsal 292. FIG. 30B shows the foot of FIG. 30A after being anatomically aligned to correct the misalignment using bone positioning guide 10. As shown, first metatarsal 210 has been rotated counterclockwise in the frontal plane (from the perspective of a patient, clockwise from the perspective of a frontal observer) and also pivoted in the transverse plane (e.g., such that the angle 350 between the first metatarsal 210 and second metatarsal 292 is reduced). Rotation and pivoting of first metatarsal 210 can cause the base 352 of first metatarsal 210 to shift relative to medial cuneiform 220. In general, it is desirable that the offset 354A between first metatarsal 210 and medial cuneiform 220 be reduced to zero (e.g., such that there is substantially no offset) after rotation and pivoting. As shown in the illustrated application of FIG. 30B, however, the base 352 of first metatarsal 210 abutting medial cuneiform 220 has shifted toward second metatarsal 292. This results in a transverse offset 354B of first metatarsal 210 toward second metatarsal 292, causing base compression between first metatarsal 210 and second metatarsal 292.

To help avoid the base shift and offset 354B observed in FIG. 30B, a clinician can insert a fulcrum in the notch between first metatarsal 210 and second metatarsal 292 at the base of the metatarsals (e.g., adjacent respective cuneiform) before actuating bone positioning guide 10. The fulcrum can provide a point about which first metatarsal 210 can rotate and/or pivot while helping minimize or avoid base compression between the first metatarsal and the second metatarsal. In addition, use of the fulcrum may cause first metatarsal 210 and medial cuneiform 220 to be better angled relative to the guide slots of bone preparation guide 150 (once installed), providing a better cut angle through the guide slots than without use of the fulcrum. This can help reduce or eliminate unwanted spring-back, or return positioning, of first metatarsal 210 after removing bone positioning guide 10 (in instances in which bone positioning guide 10 is used with the fulcrum).

FIG. 31 illustrates a bone positioning operation in which a fulcrum 356 is positioned at an intersection between a first bone and a second bone, where the first bone is being realigned relative to the second bone. In particular, FIG. 31 illustrates fulcrum 356 being positioned between first metatarsal 210 and second metatarsal 292. Fulcrum 356 may be positioned distally of bone preparation guide 150 between first metatarsal 210 and second metatarsal 292 as shown in FIG. 31 or, in other applications, proximally of the guide (e.g., at the ends of the first and second metatarsals abutting the medial and intermediate cuneiform bones, respectively). In still other examples, fulcrum 356 can be positioned in the intermetatarsal space between first metatarsal 210 and second metatarsal 292 without using bone preparation guide 150.

When used, the clinician can insert fulcrum 356 between first metatarsal 210 and second metatarsal 292 (or other adjacent bones, when not performing a metatarsal realignment) at any time prior to moving the first metatarsal (e.g., by actuating bone positioning guide 10 or other means of manipulating the bone). In different embodiments, fulcrum 356 can be inserted between first metatarsal 210 and second metatarsal 292 before or after inserting joint spacer 188 and/or placing bone preparation guide 150 over the joint being operated upon. In one embodiment, the clinician prepares the joint being operated upon to release soft tissues and/or excise the plantar flare from the base of the first metatarsal 210, as discussed above. Either before or after installing bone positioning guide 10 over adjacent bones, for example with bone engagement member 40 positioned in contact with the medial ridge of the first metatarsal 210 and tip 50 positioned in contact with second metatarsal 292, the clinician inserts fulcrum 356 at the joint between the first metatarsal and the second metatarsal. The clinician can subsequently actuate bone positioning guide 10 (e.g., rotate knob 120). In the case of a left foot as shown in FIG. 31, actuation of bone positioning guide 10 causes the first metatarsal 210 to rotate counterclockwise in the frontal plane (from the perspective of a patient) and also pivot in the transverse plane about the fulcrum. In the case of a right foot (not shown), actuation causes the first metatarsal to rotate clockwise in the frontal plane (from the perspective of a patient) and also pivot in the transverse plane about the fulcrum. Thus, for both feet, actuation of bone positioning guide 10 can supinate the first metatarsal in the frontal plane and pivot the first metatarsal in the transverse plane about fulcrum 356. While use of fulcrum 356 can minimize or eliminate base compression between adjacent bones being operated upon, in other embodiments as discussed above, the described systems and techniques can be implemented without using the fulcrum.

Figure 32:
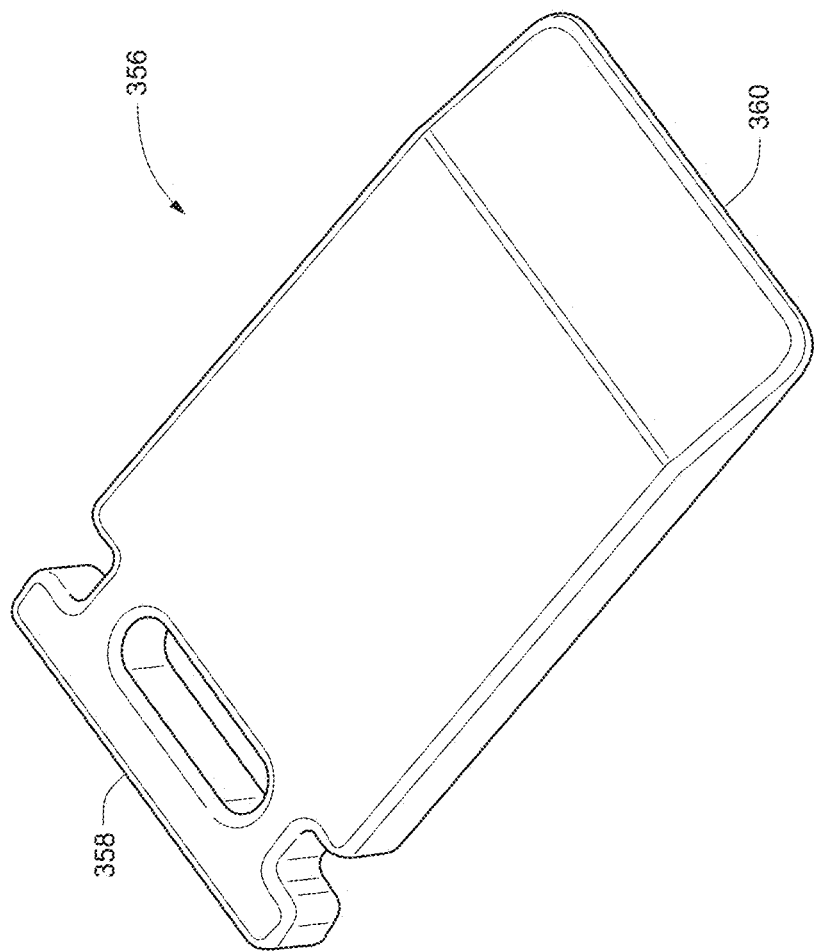
FIG. 32 is a perspective view of one example fulcrum.
Figure 33:
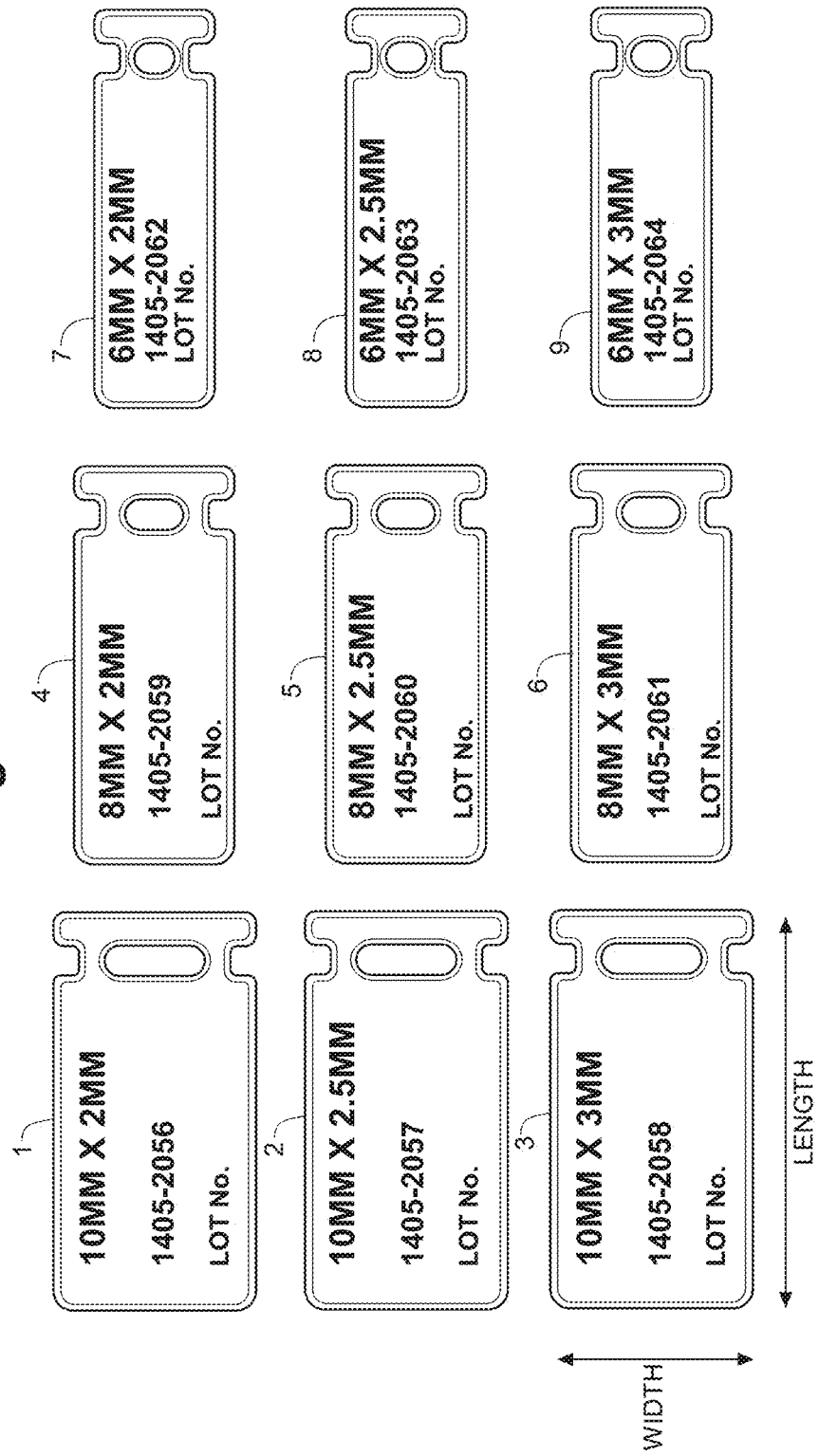
FIG. 33 illustrates an example system of different sized fulcrums.

In instances in which fulcrum 356 is used, any suitable mechanical instrument that maintains a spacing between adjacent bones can be used for the fulcrum. FIG. 32 is a perspective view of one example instrument that can be used as fulcrum 356. In this embodiment, fulcrum 356 has a generally rectangular shape and tapers in thickness along at least a portion of the length from the trailing end 358 to the leading end 360. Fulcrum 356 may be sized sufficiently small so that it does not interfere with placement of bone preparation guide 150 on the joint being worked upon. In some embodiments, the clinician is provided a system containing multiple different size and/or shape fulcrums and allowed to choose the specific size and/or shape fulcrum desired for the specific procedure being performed. FIG. 33 illustrates an example kit or system of different sized fulcrums, labeled with exemplary "width×thickness" sizes, that may be provided to a clinician in such an embodiment. In some examples, fulcrum 356 has a width ranging from 5 millimeters to 15 millimeters (e.g., about 6 millimeters to about 10 millimeters) and a thickness ranging 1 millimeter to 12 millimeters (e.g., about 2 millimeters to about 3 millimeters), although fulcrums with different dimensions can be used.

While FIGS. 32 and 33 illustrate one example style of fulcrum, other mechanical instruments providing a fulcrum functionality can be used without departing from the scope of the disclosure. For instance, as alternative examples, a surgical pin or rod, a screw driver head/shaft, an osteotome, or a retractor may be used as fulcrum 356. Depending on the instrument used as a fulcrum, the fulcrum may have a variety of cross-sectional shapes, such as a generally polygonal shape (e.g., square, hexagonal), a generally arcuate shape (e.g., circular, elliptical), or combinations of polygonal and arcuate shapes.

Figure 34:
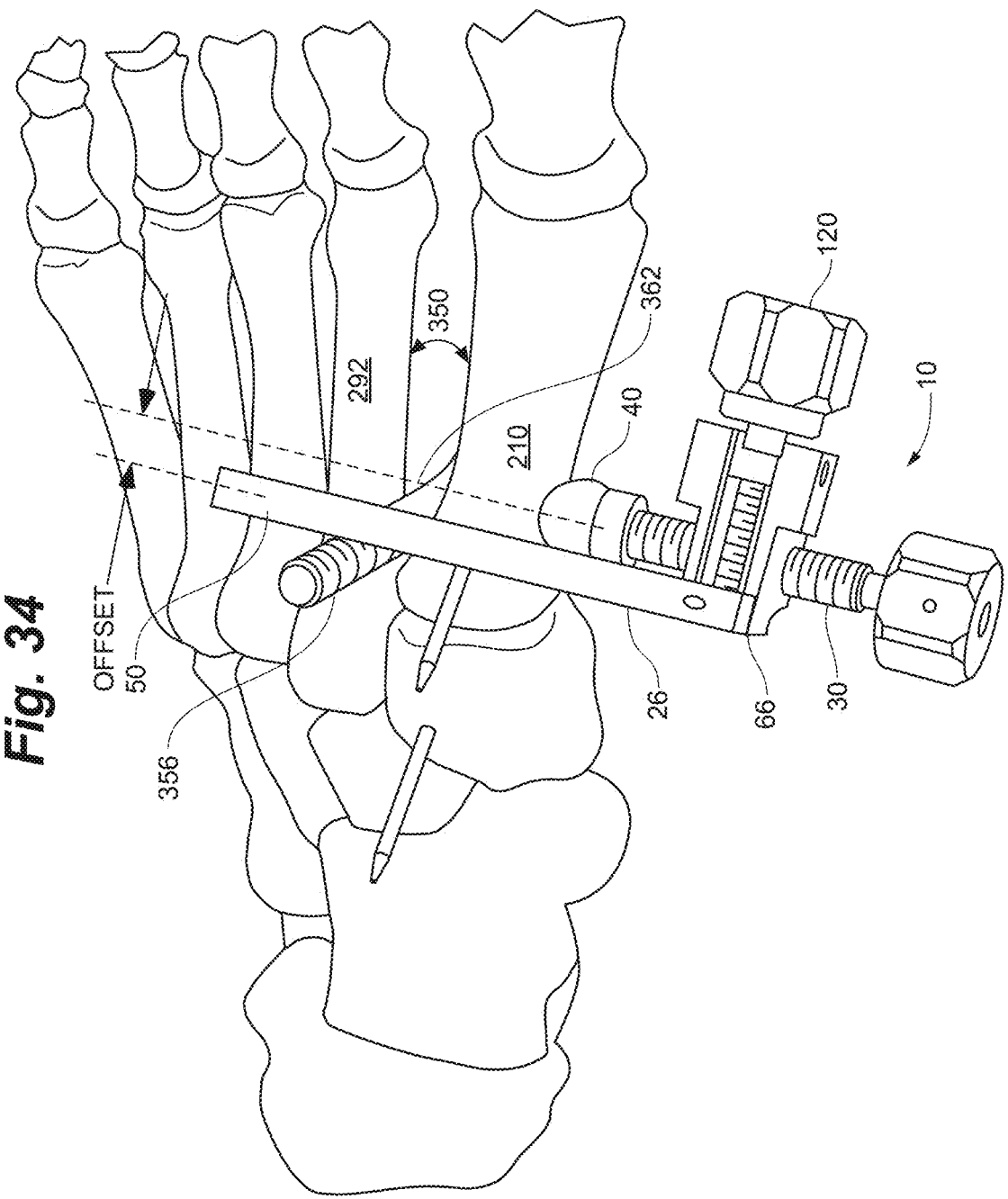
FIG. 34 is a perspective view of another bone positioning guide according to an embodiment of the invention.

As discussed above, bone positioning guide 10 can have a variety of different configurations, including a configuration in which bone engagement member 40 is laterally offset from tip 50. FIG. 34 is a perspective view of bone positioning guide 10 showing an example arrangement in which bone engagement member 40 is laterally offset from tip 50. In this embodiment, the first end 60 of main body member 20 is laterally offset from an axis 362 extending through shaft 30 and a geometric center of bone engagement member 40. In particular, in the illustrated configuration, tip 50 is offset laterally in the direction of the cuneiform relative to bone engagement member 40. As a result, when bone positioning guide 10 is actuated, e.g., by rotating knob 120, a moment can be created by the offset tip. This can cause the end of the first metatarsal 210 adjacent the proximal phalange to pivot toward the second metatarsal 292 and close angle 350, e.g., while the opposite end of the first metatarsal adjacent the medial cuneiform pivots away from the second metatarsal. This can also help avoid base compression between the first and second metatarsals.

As discussed above with respect to FIGS. 19 and 20, a joint spacer 188 can be positioned in a joint between a first metatarsal and a medial cuneiform before placing bone preparation guide 150 over the joint spacer. Bone preparation guide 150 can have an opening 170 (FIG. 5) sized to receive joint spacer 188. In some examples, opening 170 of bone preparation guide 150 is size and/or shaped indexed to joint spacer 188 such that there is substantially no, or no, relative movement between the guide and spacer (once bone preparation guide 150 is placed over joint spacer 188). This arrangement can ensure that bone preparation guide 150 is positioned precisely at the location where guided by joint spacer 188.

In practice, once bone preparation guide 150 is placed over joint spacer 188, the guide slots of the bone positioning guide may not be perfectly aligned with the ends of the bones (e.g., first metatarsal 210 and medial cuneiform 220) to be cut through the guide slots. Accordingly, in other configurations, opening 170 of bone preparation guide 150 may not be sized and/or shaped and/or indexed to joint spacer 188. In other words, opening 170 of bone preparation guide 150 may have a different cross-sectional size and/or shape than the cross-sectional size and/or shape of joint spacer 188. In these configurations, bone preparation guide 150 may actuate or rotate about an axis extending through the length of joint spacer 188. As a result, after the clinician places bone preparation guide 150 over joint spacer 188, the clinician may rotate bone preparation guide 150 around joint spacer 188 until the guide slots of the bone preparation guide are better aligned with the ends of the bones to be cut (e.g., first metatarsal 210 and medial cuneiform 220). Depending on the configuration of opening 170 of bone preparation guide 150 and the configuration of joint spacer 188, the guide may rotate freely (e.g., 360 degrees) around the joint spacer (e.g., seeker) or within a bounded angular range (e.g., from plus 20 degrees to minus 20 degrees from a normal position).

Figure 35:
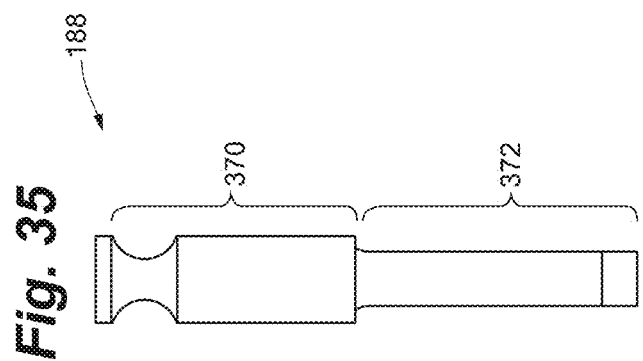
FIG. 35 illustrates an example configuration of a joint spacer that can allow a bone preparation guide to rotate around the spacer.

FIG. 35 illustrates one example configuration of a joint spacer 188 that can allow bone preparation guide 150 to rotate around the spacer (e.g., seeker). As shown in the illustrated example, joint spacer 188 has a proximal portion 370 having a cylindrical cross-section and a distal portion 372 having a rectangular cross-section. A leading edge of the distal portion 372 is insertable into the joint between the first metatarsal 210 and the medial cuneiform 220. Once bone preparation guide 150 is inserted over joint spacer 188, body 154 of the guide (FIG. 5) may be positioned about the proximal portion 370. This can allow the guide to be rotated around the proximal portion.

Figure 36B:
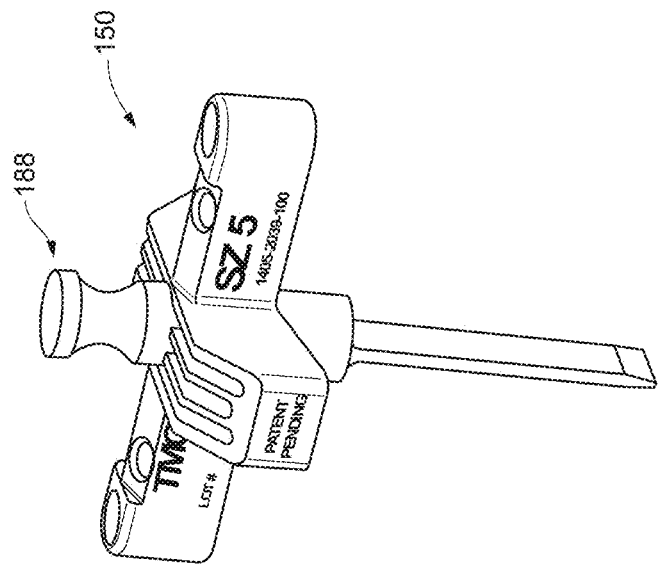
FIG. 36B is a perspective view of the example bone positioning guide of FIG. 36A shown with the joint spacer from FIG. 35 inserted into the guide.
Figure 36A:
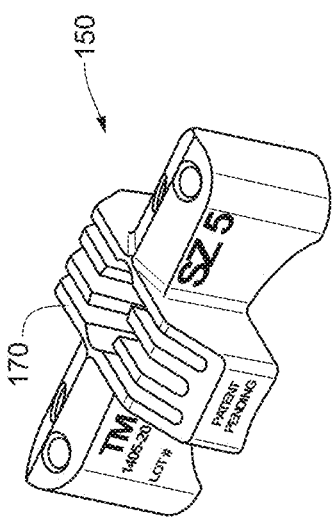
FIG. 36A is a perspective view of an example configuration of a bone positioning guide having an opening with circular cross-sectional shape.

In other configurations, opening 170 of bone preparation guide 150 may be size and/or shape indexed to the cross-sectional size and/or shape of joint spacer 188 but still provide relative rotation between the two components. For example, opening 170 may have a circular cross-section sized and shaped to receive proximal portion 370 of joint spacer 188 from FIG. 35. Because both opening 170 of bone preparation guide 150 and proximal portion 370 of joint spacer 188 have circular cross-sections in such an embodiment, the two components may rotate relative to each other. FIG. 36A is a perspective view of an example configuration of bone preparation guide 150 having an opening 170 with circular cross-sectional shape. FIG. 36B is a perspective view of the example bone positioning guide of FIG. 36A shown with joint spacer 188 from FIG. 35 inserted into the guide.

In embodiments where bone preparation guide 150 can rotate relative to joint spacer 188, the bone positioning guide and/or joint spacer may include a locking mechanism that is engageable to lock the rotational angle of the bone positioning guide relative to the joint spacer. For example, bone preparation guide 150 may include a set screw with thumb wheel that can be rotated, causing a distal end of the set screw to bear against or retract away from joint spacer 188. In use, a clinician can rotate bone preparation guide 150 around joint spacer 188 until the guide slots of the bone preparation guide are best aligned with the ends of the bones to be cut (e.g., first metatarsal 210 and medial cuneiform 220). The clinician can then engage the locking mechanism to prevent further rotation of bone preparation guide 150 relative to joint spacer 188 before performing further steps of the procedure.

A bone correction procedure can be accomplished using one or more instruments according to the disclosure. In some applications, a bone correction procedure, such as a tarsal-metatarsal joint fusion procedure to correct a bunion deformity, is performed utilizing a fulcrum as a pivot point. The first metatarsal is moved relative to a second metatarsal about the fulcrum without utilizing bone positioning guide 10. In these applications, the clinician can insert the fulcrum into an intermetatarsal space between the first and second metatarsals and physically grasp the first metatarsal and move the metatarsal about the fulcrum. For example, the clinician may directly grasp the first metatarsal with his hand or indirectly grasp the first metatarsal through an intermediate tool, such as a K-wire or pin inserted into the first metatarsal, a tenaculum or tongs, or other grasping instrument. Thereafter, the clinician may translate his hand relative to the foot of the patient being operated upon to move the first metatarsal about the fulcrum and relative to the second metatarsal, e.g., to anatomically align the first metatarsal with respect to the second metatarsal.

Figure 37:
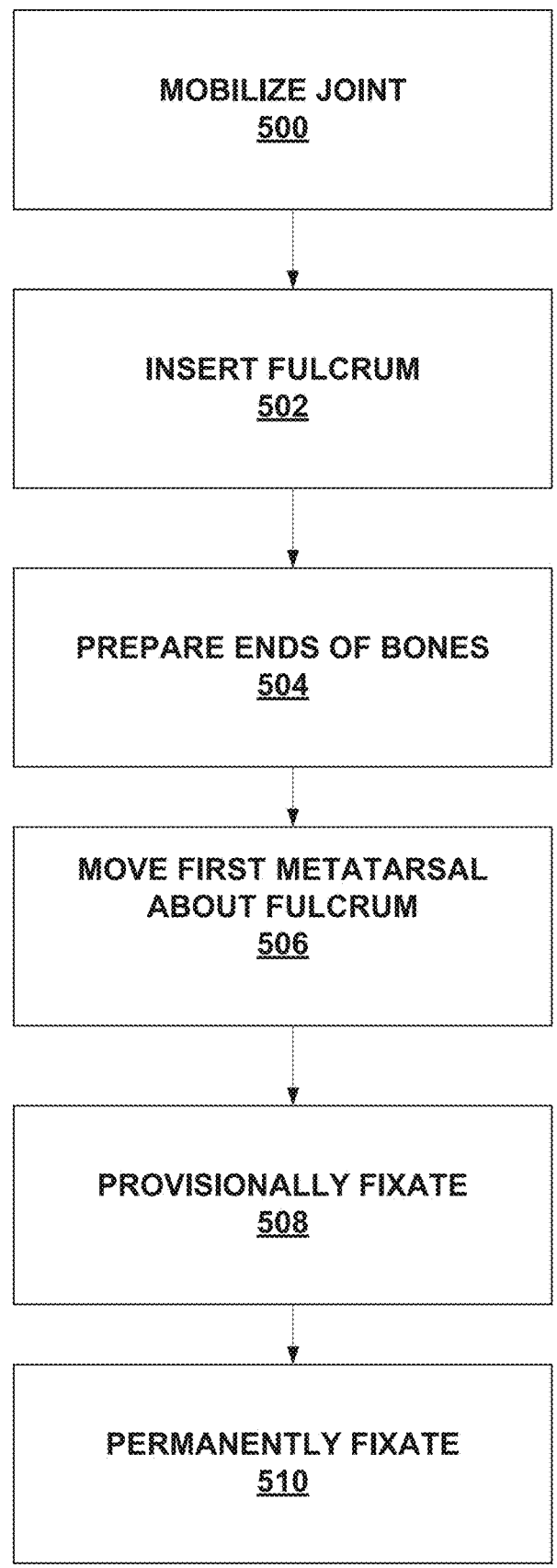
FIG. 37 is a block flow diagram of an example bone correction technique utilizing a fulcrum.

FIG. 37 is a block flow diagram of an example bone correction technique utilizing a fulcrum. Specific steps of the technique of FIG. 37 can be performed utilizing techniques and/or instruments discussed above. As shown, the example technique of FIG. 37 includes mobilizing a tarsal-metatarsal joint by releasing soft tissue and/or obstructing bone (500). After customary surgical preparation and access, the clinician may mobilize the tarsal-metatarsal joint by inserting a cutting instrument (e.g., saw, rotary bur, osteotome) at least partially between the first metatarsal and medial cuneiform. The clinician may use the cutting instrument to release soft tissues and/or excise the plantar flare from the base of the first metatarsal. Excising the plantar flare may involve cutting plantar flare off the first metatarsal so the face of the first metatarsal is generally planar. In some applications, the dorsal-lateral flare of the first metatarsal may also be excised to create space for the correction procedure.

The technique of FIG. 37 further involves inserting a fulcrum between the first metatarsal and the second metatarsal (502). The fulcrum may be inserted from the dorsal side of the foot toward the plantar side of the foot in the intermetatarsal space between the first metatarsal and second metatarsal. Although the fulcrum may be positioned at any desired location in the intermetatarsal space, in some applications, the fulcrum is positioned adjacent to, and optionally in contact with, a proximal portion of the first metatarsal and/or the second metatarsal. For example, the fulcrum may be positioned adjacent to, and optionally in contact with, a proximal-most half of the first metatarsal and/or proximal-most half of the second metatarsal, such as the proximal-most third or proximal-most quarter of the first metatarsal and/or the second metatarsal. In one application, the fulcrum is positioned in the intermetatarsal space adjacent to, and optionally in contact with, the base of the first metatarsal facing the medial cuneiform and the base of the second metatarsal facing the intermediate cuneiform. This positioning can help prevent or minimize lateral translation of the base of the first metatarsal toward the base of the second metatarsal during alignment of the first metatarsal. In some applications, the clinician inserts the fulcrum from the dorsal toward the plantar side of the foot in the intermetatarsal space and then translates the fulcrum proximally in the intermetatarsal space.

The technique of FIG. 37 also involves preparing the end of the first metatarsal and/or the opposed end of the medial cuneiform (504). Typically, bone preparation is performed after inserting the fulcrum in the intermetatarsal space (502), although bone preparation can be performed prior to inserting the fulcrum. To prepare the end of the first metatarsal and the end of the medial cuneiform, a tissue removing instrument can be applied to the ends of the bones. In one example, a cutting instrument is applied to transect each bone and thereby form a new end surface, e.g., by inserting the cutting instrument through a slot defined bone preparation guide 150. Additionally or alternatively, the tissue removing instrument can be applied to the end face of each bone to morselize at least a portion of the end face.

Independent of the specific technique used to prepare the end of the first metatarsal and/or the opposed end of the medial cuneiform (504), the technique of FIG. 37 includes moving the first metatarsal to help correct the anatomical misalignment (506). The first metatarsal can be moved relative to the second metatarsal before and/or after preparing the end of the first metatarsal and/or the opposed end of the medial cuneiform. To move the first metatarsal relative to the second metatarsal, the clinician may directly or indirectly grasp the first metatarsal and translate a distal portion of the first metatarsal toward the second metatarsal (e.g., a distal portion of the second metatarsal) in the transverse plane. As the distal end of the first metatarsal moves toward the second metatarsal in the transverse plane, the proximal portion of the first metatarsal can pivot about the fulcrum. For example, the fulcrum can function as a central point around which the proximal portion of the first metatarsal turns as the distal portion of the first metatarsal translates laterally. Accordingly, moving the distal portion of the first metatarsal toward the second metatarsal can reduce the intermetatarsal space, and hence intermetatarsal angle, between the first metatarsal and the second metatarsal.

As the first metatarsal pivots in the transverse plane toward the second metatarsal, closing the intermetatarsal space, a proximal portion of the first metatarsal may contact and press against the fulcrum, thereby causing the fulcrum to contact and press against a proximal portion of the second metatarsal. The fulcrum may function to maintain spacing between the proximal portion of the first metatarsal and proximal portion of the second metatarsal, e.g., such a spacing equal to the width of the fulcrum. This may help reduce or eliminate shifting or translation of the base of the first metatarsal toward the base of the second metatarsal during pivoting.

In some applications of the technique of FIG. 37, the clinician may rotate the first metatarsal in the frontal plane in addition to or in lieu of translating the first metatarsal in the transverse plane. For example, either before, after, or concurrent with moving the distal portion of the first metatarsal toward the second metatarsal in the frontal plane, the clinician can directly or indirectly grasp the first metatarsal and rotate the metatarsal in the frontal plane. The clinician may rotate the first metatarsal about its longitudinal axis into an anatomically correct frontal plane position to correct a frontal plane deformity. Rotating the first metatarsal in the frontal plane may further rotate the sesamoid bones (e.g., tibial sesamoid bone and fibular sesamoid bone) from a misaligned position to an aligned position under the first metatarsal. In some examples, the clinician additionally or alternatively moves the first metatarsal in the sagittal plane to correct a misalignment in the sagittal plane.

In some applications of the technique of FIG. 37, the clinician moves the first metatarsal in at least one plane from an anatomically misaligned position with respect to the second metatarsal to an anatomically aligned position. The at least one plane may be one or more planes selected from the frontal plane, the transverse plane, and the sagittal plane. For example, the clinician may move the first metatarsal in any two of the three planes or even in all three of the planes to adjust the first metatarsal from an anatomically misaligned position to an anatomically aligned position.

After suitably moving the first metatarsal relative to the second metatarsal, the joint between the first metatarsal and medial cuneiform may be provisionally fixated (508). In one example, a fixation wire is driven into the first metatarsal and the medial cuneiform to provisionally fixate the joint. In another example, a compression pin, such as a threaded olive pin, is inserted through the first metatarsal and into the medial cuneiform to provide compression and provisional fixation between the first metatarsal and the medial cuneiform. The fulcrum can be removed from the intermetatarsal space before or after provisionally fixating the joint.

Following optional provisional fixation, the corrected position of the first metatarsal can be permanently fixated by fixing the position of the first metatarsal with respect to the medial cuneiform (510). One or more bone plates can be applied across the tarsal-metatarsal joint and the provisional fixation hardware removed. For example, a first bone plate may be positioned on a dorsal-medial region of the first metatarsal and on the medial cuneiform while a second bone plate is positioned on a medial-plantar region of the first metatarsal and on the medial cuneiform. In these applications, the second bone plate may or may not be a helical-shaped bone plate extending from a medial region of the medial cuneiform to a plantar region of the first metatarsal across the joint.

FIG. 38 is a perspective view of a foot showing an example position of a fulcrum during a bone correction procedure according to the method of FIG. 37. As shown, fulcrum 356 is positioned in the intermetatarsal space between the first metatarsal 210 and the second metatarsal 292. In particular, fulcrum 356 is illustrated as being positioned between a proximal portion of first metatarsal 210 adjacent base 352 and an opposed proximal portion of second metatarsal 292. An optional pin 512 is inserted into the first metatarsal 210, providing a structure that a clinician can grab to move and manipulate the first metatarsal relative to the second metatarsal. As discussed with respect to FIG. 37, the clinician may pivot the first metatarsal 210 about fulcrum 356 toward the second metatarsal 292, reducing the intermetatarsal angle 350 between the first and second metatarsals. The clinician may also rotate the first metatarsal 210 in the frontal plane. The use of fulcrum 356 can provide a pivot surface that also maintains a defined spacing between first metatarsal 210 and second metatarsal 292, potentially leading to a more anatomically correct realignment than when moving first metatarsal 210 without using the fulcrum.

Figure 39A:
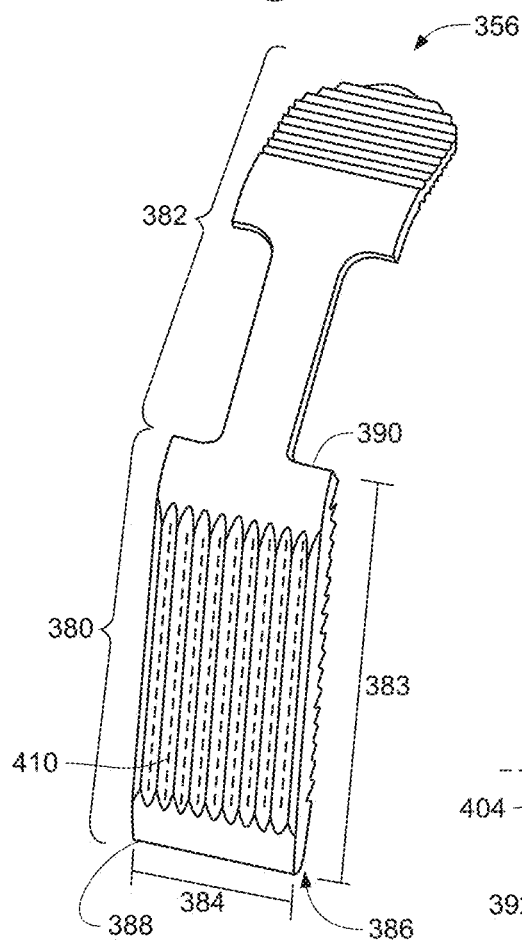
FIGS. 39A and 39B are different perspective views of another example fulcrum that can be used during a bone correction procedure.
Figure 39B:
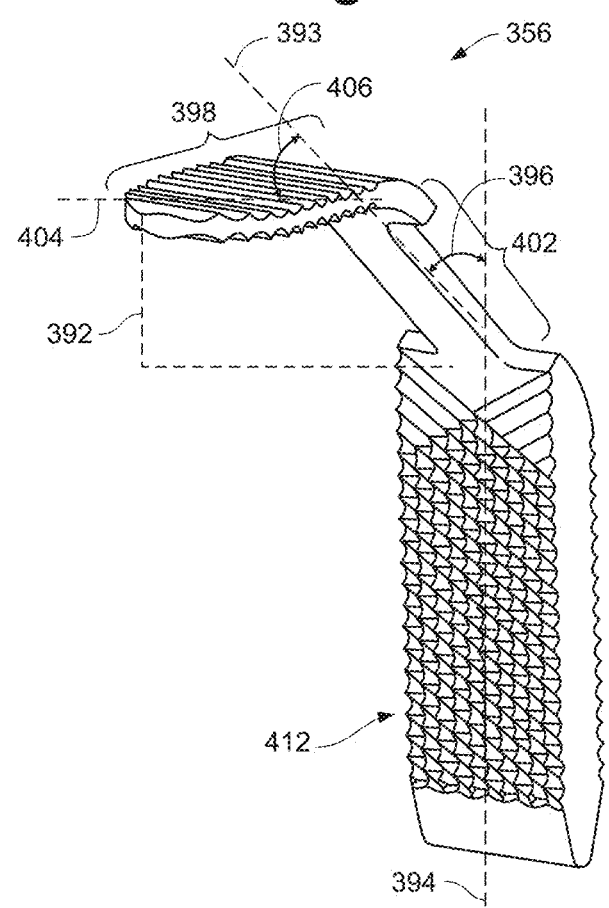

As discussed above with respect to FIGS. 32 and 33, fulcrum 356 can have a variety of different configurations that provide a fulcrum functionality. FIGS. 39A and 39B illustrate another example configuration of fulcrum 356 that can be used according to the disclosure. FIG. 39A is a perspective view of one side of fulcrum 356, while FIG. 39B is a perspective view of the fulcrum from the opposite side. In the illustrated configuration, fulcrum 356 includes a body 380 and a handle 382 operatively connected to the body. Typically, body 380 and handle 382 will be formed as a unitary structure, e.g., by milling, casting, or molding the components to be permanently and structurally integrated together. However, body 380 and handle 382 may be fabricated as separate components that are subsequently joined together.

Body 380 can be configured (e.g., sized and shaped) to be inserted into an intermetatarsal space between adjacent metatarsals. For example, body 380 may be configured to be inserted between a first metatarsal and a second metatarsal. Body 380 is illustrated as having a rectangular shape with a length 383 greater than its width 384 and thickness 386. Moreover, in this configuration, body 380 has a constant width 384 across its length but has a thickness 386 that that tapers along at least a portion of the length from the leading end 388 to the trailing end 390. For example, body 380 may have a tapered leading end 388 to facilitate insertion of fulcrum 356 in a space between adjacent metatarsals. In other configurations, body 380 may have a constant thickness across is length or may define a different generally polygonal shape (e.g., square, hexagonal) and/or generally arcuate shape (e.g., circular, elliptical).

Figure 40:
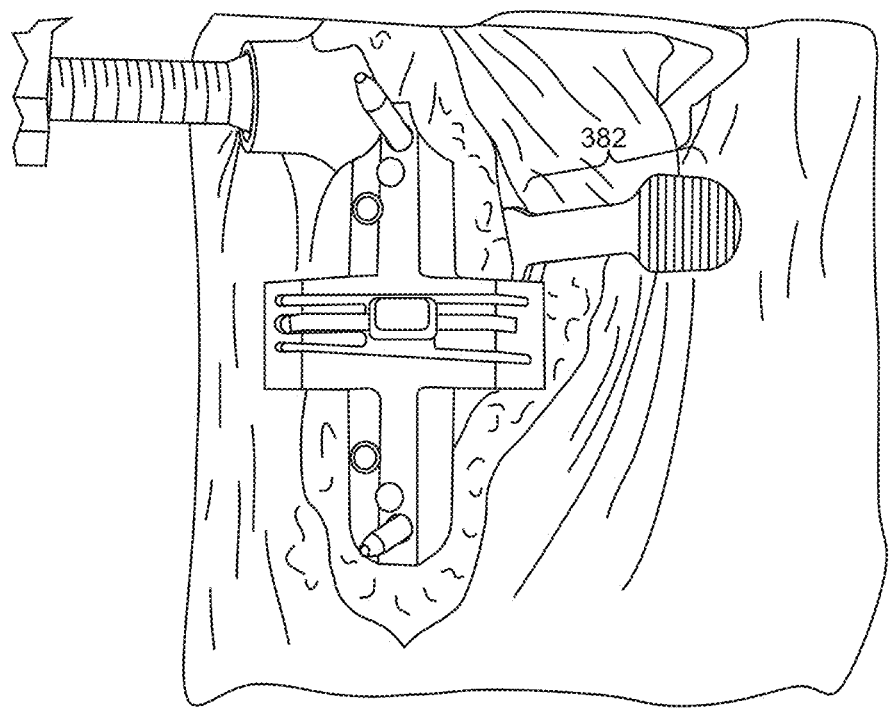
FIG. 40 is an image of the example fulcrum of FIGS. 39A and 39B inserted between a first metatarsal and a second metatarsal.

Fulcrum 356 in FIGS. 39A and 39B includes handle 382. Handle 382 can project angularly away from body 380 to define a tissue retraction space 392. Tissue retraction space 392 may be a region bounded on one side by body 380 and one or more other sides by handle 382. In use, fulcrum 356 may be inserted into an intermetatarsal space with handle 382 extending out of the surgical incision and over an epidermal layer with tissue captured in tissue retraction space 392. For example, fulcrum 356 may be inserted into an intermetatarsal space with handle 382 projecting toward the lateral side of the foot being operated upon. Tissue retraction space 392 may help retract tissue and push the tissue laterally away from a first metatarsal and/or medial cuneiform being operated upon. FIG. 40 illustrates fulcrum 356 in such an application with the fulcrum inserted between a first metatarsal and a second metatarsal and handle 382 extending toward the lateral side of the foot being operated upon. As shown, handle 382 pushes the skin of the foot away from the surgical incision line, helping to provide access to the surgical site in addition to providing fulcrum functionality.

With further reference to FIGS. 39A and 39B, handle 382 is illustrated as projecting laterally at a non-zero degree angle away from body 380. The specific angular orientation of the handle 382 relative to the body 380 may vary. However, in some examples, handle 382 is oriented relative to the body 380 so a handle axis 393 intersects an axis 394 extending along the length of the body at an acute angle 396 ranging from 20 degrees to 75 degrees, such as 35 degrees to 55 degrees. Moreover, handle 382 may be composed of a single linear portion that intersects body 380 at a specific angular orientation or may be composed of multiple linear portions oriented at different angles relative to each other.

In the illustrated example, handle 382 includes a grip portion 398 and a handle body 402. The grip portion 398 can provide a surface that a clinician physically grips to insert fulcrum 356 into an intermetatarsal space. For example, grip portion 398 may contain knurling or other anti-friction surfacing texturing to allow the clinician to help grip the fulcrum. Handle body 402 may be positioned between the body 380 of fulcrum 356 and grip portion 398. Handle body 402 may or may not have a reduced cross-sectional width compared to body 380 and/or grip portion 398, as illustrated.

When configured with grip portion 398, the grip portion can be co-linear with handle body 402 or may be offset relative to the handle body. When grip portion 398 is offset from handle body 402, a grip axis 404 extending along the length of the grip portion may intersect the handle axis 393 at an acute ranging from 20 degrees to 75 degrees, such as 35 degrees to 55 degrees, although other angular arrangements can also be used. In the illustrated configuration, grip axis 404 is perpendicular to the axis 394 defined by body 380. Accordingly, when inserted into an intermetatarsal space, retracted tissue may be bounded by a laterally-facing side of body 380, by the lower surface of grip portion 393, and in the dorsal-lateral direction by handle portion 392.

In some examples, the bone-contacting faces of body 380 are configured to inhibit and/or facilitate relative motion between a bone and the respective bone-contacting face. With reference to FIG. 39A, body 380 of fulcrum 356 has a first face 410, which may be positioned in contact with a first metatarsal. First face 410 may have surface features which allow the contacting metatarsal (e.g., first metatarsal) to rotate in the frontal plane while contacting the face but inhibit movement of the metatarsal in the proximal to distal direction. The surface features may be implemented as directionally-oriented ribs and/or grooves, which are illustrated in FIG. 39A as being multiple grooves extending lengthwise across body 380. By orienting the grooves lengthwise, the edges of the grooves may have a tendency to engage or bite into the metatarsal if the metatarsal is moved proximally or distally, thereby inhibiting such movement. However, the grooves can allow the metatarsal to rotate in the frontal plane against first face 410 without inhibiting such rotation.

Figure 41:
FIG. 41 illustrates an alternative arrangement of surface features that may be used on the example fulcrum of FIGS. 39A and 39B.

Additionally or alternatively, the body 380 may have different surface features on the opposite face from first face 410. With reference to FIG. 39B, for example, body 380 of fulcrum 356 has a second face 412 that is opposite first face 410. Second face 412 may have surface features that inhibit movement between fulcrum 356 and the contacting metatarsal (e.g., second metatarsal) in the dorsal-to-plantar direction. The surface features may be implemented as directionally-oriented ribs and/or grooves. For example, in FIG. 39B, second face 412 is illustrated as having knurling, or a series of intersecting and overlapping ridges. FIG. 41 is perspective view of the second face 412 of fulcrum 356 showing an alternative arrangement of surface features that may be used. In this alternative configuration, the surface features on second face 412 are illustrated as being multiple grooves extending widthwise across body 380. By orienting the grooves widthwise, the edges of the grooves may have a tendency to engage or bite into the metatarsal if the metatarsal is moved plantarly or dorsally, thereby inhibiting such movement. The knurling illustrated on FIG. 39B can also achieve this functionality.

In the configuration of FIGS. 39A and 39B, handle 382 includes grip portion 398 that can provide a surface a clinician physically grips to insert fulcrum 356. In other configurations, handle 382 may be implemented using a second fulcrum body that is a different size and/or shape than body 380. This arrangement can provide a clinician with a single instrument having two functional ends, either one of which can be selected and used by the clinician, e.g., depending on the characteristics of the patient undergoing a surgical procedure.

Figure 42A:
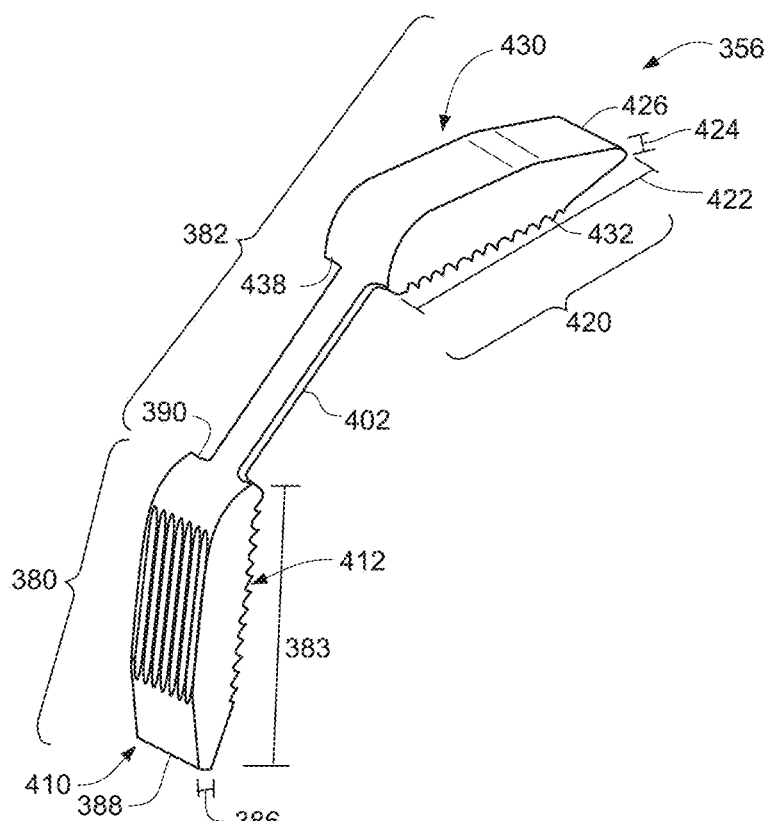
FIGS. 42A and 42B are perspective and side views, respectively, of an example fulcrum having two fulcrum bodies.
Figure 42B:
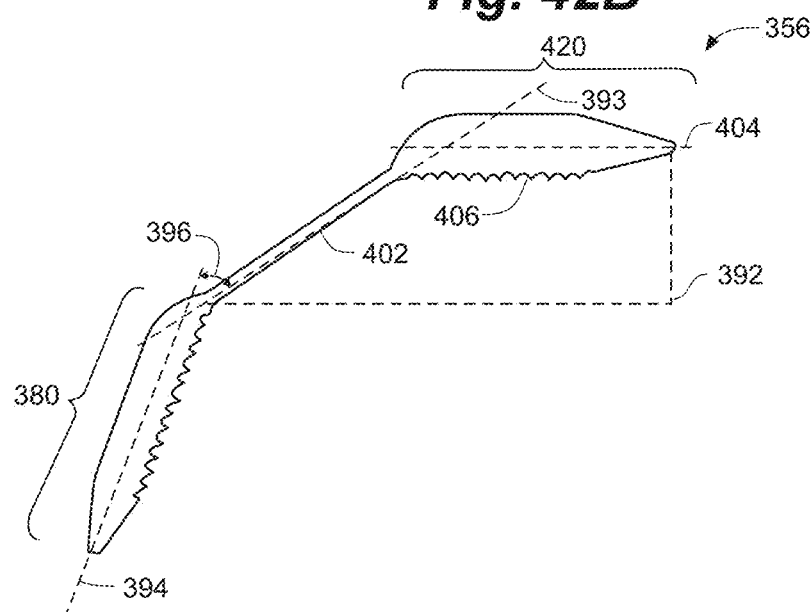

FIGS. 42A and 42B are perspective and side views, respectively, of such an example fulcrum 356 having two fulcrum bodies. As shown in this example, fulcrum 356 includes the body 380 and the handle 382 projecting at a non-zero degree angle away from the body. The body 380 provides a first fulcrum body configured (e.g., sized and/or shaped) to be inserted into an intermetatarsal space. In addition, handle 382 in this example is defined at least in part by a second fulcrum body 420. The second fulcrum body 420 may also be configured (e.g., sized and/or shaped) to be inserted into an intermetatarsal space. The first fulcrum body 380 can differ from the second fulcrum 420 body by having a different size and/or shape.

In FIGS. 42A and 42B, the first fulcrum body 380 and the second fulcrum body 420 are shown as having the same shape but different sizes. In particular, first fulcrum body 380 has a length 383, a thickness 386, and a width orthogonal to the length and thickness. Further, the second fulcrum body 420 has a length 422, a thickness 424, and a width orthogonal to the length and thickness. The thickness 422 of the second fulcrum body 420 is illustrated as being greater than the thickness 386 of the first fulcrum body 380. The length and width of the first and second fulcrum bodies 380, 420 are illustrated as being the same but may be different in other examples (e.g., different width with same length, different length but same width, or different length and width).

In general, configuring the first fulcrum body 380 and second fulcrum body 420 with different thicknesses can be useful to facilitate use in different sized intermetatarsal spaces. For example, the clinician may select one sized fulcrum body over the other sized fulcrum body based on the anatomy (e.g., intermetatarsal space sizing) of the patient undergoing a surgical procedure. If the clinician determines upon beginning to insert the selected fulcrum that the selected fulcrum is inappropriately sized, the clinician may retract the fulcrum, flip the instrument, and insert the fulcrum on the opposite side of the instrument.

While the first fulcrum body 380 and second fulcrum body 420 can be configured with a variety of different sizes, in some examples, each fulcrum body has a thickness ranging from 0.5 millimeters to 12 millimeters, such as from 1 millimeter to 10 millimeters, or from 1 millimeter to 5 millimeters. The thickness 424 of the second fulcrum body 420 may be at least 0.2 millimeters thicker than the thickness 386 of the first fulcrum body, such as at least 0.5 millimeters thicker, at least 1 millimeter thicker, or at least 2 millimeters thicker. In some examples, first fulcrum body 380 and second fulcrum body 420 each have a width within a range from 5 millimeters to 15 millimeters (e.g., about 6 millimeters to about 10 millimeters) and a length ranging from 10 millimeters to 30 millimeters, although other dimensions can be used.

In the illustrated example of FIGS. 42A and 42B, the first fulcrum body 380 has a leading end 388 and a trailing end 390 and the second fulcrum body 420 has a leading end 426 and a trailing end 428. In some examples as shown, the leading end 388 of the first fulcrum body 380 and/or the leading end 426 of the second fulcrum body 420 has a thickness that tapers adjacent the leading end. This configuration can be useful to facilitate insertion of a fulcrum body into an intermetatarsal space. When configured with a tapered leading end, the exemplary thickness ranges discussed above may be measured as the maximum thickness of the fulcrum body at any location along the length of the body.

When fulcrum 356 is implemented with first fulcrum body 380 and second fulcrum body 420, the bone-contacting faces of one or both of the fulcrum bodies may be configured to inhibit and/or facilitate relative motion between a bone and the respective bone-contacting face, as discussed with respect to FIGS. 39A, 39B, and 41. For example, a first face 410 of first fulcrum body 380 and/or a first face 430 of second fulcrum body 420 may have surface features which allow a contacting metatarsal (e.g., first metatarsal) to rotate in the frontal plane while contacting the face but inhibit movement of the metatarsal in the proximal to distal direction, as discussed above. Similarly, a second face 412 of first fulcrum body 380 and/or a second face 432 of second fulcrum body 420 may have surface features that inhibit movement between fulcrum 356 and a contacting metatarsal (e.g., second metatarsal) in the dorsal-to-plantar direction, as also discussed above.

In the illustrated example, first fulcrum body 380 and second fulcrum body 420 are oriented at a non-zero degree relative to each other and separated by a handle body 402, e.g., of lesser cross-sectional width. For example, as discussed with respect to FIGS. 39A and 39B, handle 382 may be oriented relative to first fulcrum body 380 such that handle axis 393 intersects an axis 394 extending along the length of the body at an acute angle 396. When handle 382 includes the handle body 402 and the second fulcrum body 420, the second fulcrum body can be co-linear with handle body 402 or may be offset relative to the handle body. For example, an axis 404 extending along the length of the second fulcrum body may intersect the handle axis 393 at an acute angle 406 ranging from 20 degrees to 75 degrees, such as 35 degrees to 55 degrees, as discussed above.

In yet other configurations where fulcrum 356 is configured with multiple ends of different dimensions, the ends may or may not be separated by a separate handle body 402. For example, first fulcrum body 380 and second fulcrum body 420 may be formed as a unitary structure (e.g., as opposed ends of a linear or curved unitary body).

Figure 43A:
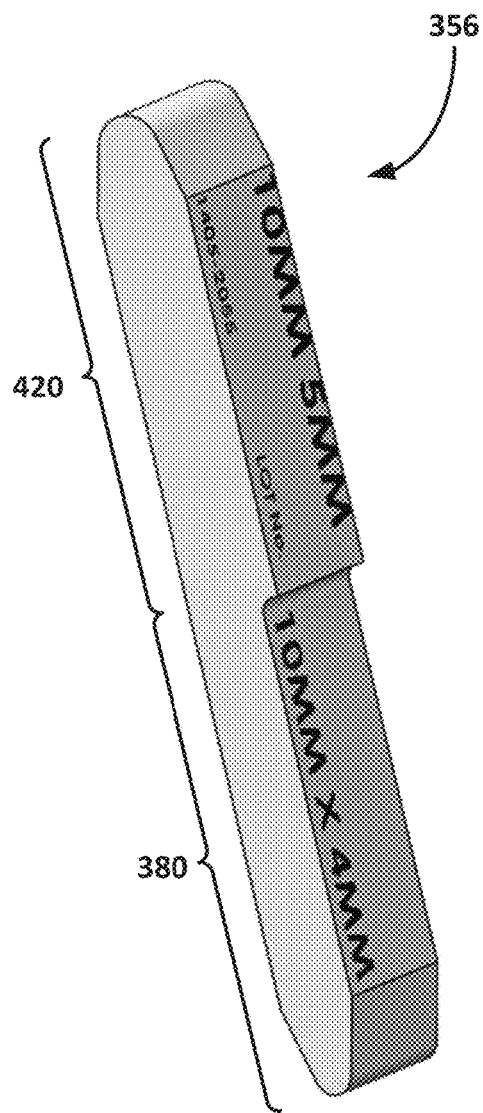
FIGS. 43A and 43B are perspective and side views, respectively, of an example multidimensional fulcrum having ends of different dimensions and a unitary body.
Figure 43B:
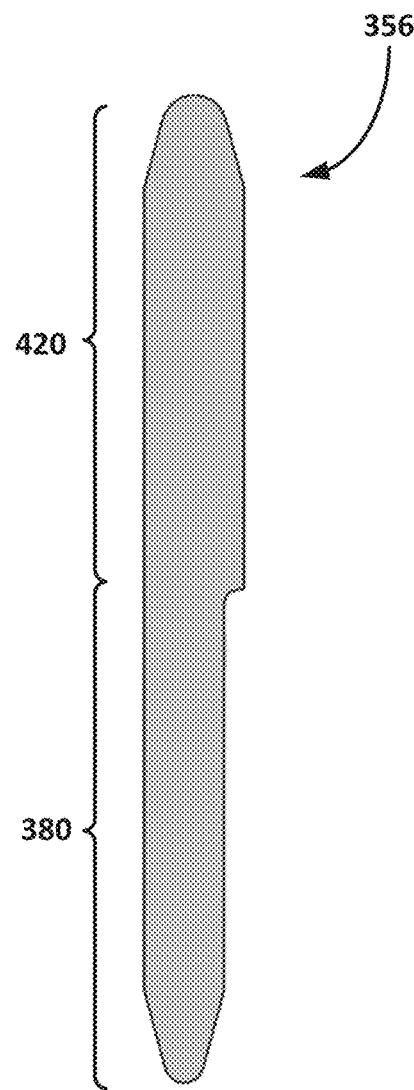

FIGS. 43A and 43B are perspective and side views, respectively, of an example multidimensional fulcrum having ends of different dimensions. As shown, fulcrum 356 is composed of first fulcrum body 380 and second fulcrum body 420 as discussed above with respect to FIGS. 42A and 42B. In the configuration illustrated in FIGS. 43A and 43B, however, the first fulcrum body 380 and the second fulcrum body 420 are integrated together to form a unitary fulcrum body having two opposed ends of different dimensions. As illustrated, the unitary fulcrum body has a generally rectangular shape such that opposed ends of the fulcrum are separated by a linear length of the body. However, the body may be curved or non-linear in alternative configurations. As discussed above, the first fulcrum body 380 and the second fulcrum body 420 forming the respective portions of the unitary body can have a variety of different dimensions, and may or may not have surface features, to provide a clinician with a variety of fulcrum options in a single instrument.

Embodiments of the invention also include a disposable, sterile kit that includes an embodiment of a bone positioning guide and/or bone preparation guide and/or fulcrum described herein. Other components that may be included within the sterile kit include bone fixation devices.

Thus, embodiments of the invention are disclosed. Although the present invention has been described with reference to certain disclosed embodiments, the disclosed embodiments are presented for purposes of illustration, and not limitation, and other embodiments of the invention are possible. One skilled in the art will appreciate that various changes, adaptations, and modifications may be made without departing from the spirit of the invention.

The invention claimed is:

1. A method of correcting a bunion deformity comprising:
making an incision on a foot to provide access to a tarsal-metatarsal joint;
inserting a fulcrum between a first metatarsal and a second metatarsal;
moving the first metatarsal relative to a medial cuneiform to establish a moved position of the first metatarsal, wherein moving the first metatarsal relative to the medial cuneiform comprises moving the first metatarsal against the fulcrum; and
fixing the moved position of the first metatarsal relative to the medial cuneiform by inserting a fixation device across the tarsal-metatarsal joint.

2. The method of claim 1, wherein moving the first metatarsal against the fulcrum comprises maintaining a separation distance between the first metatarsal and the second metatarsal during movement.

3. The method of claim 2, wherein the second metatarsal contacts the fulcrum and the separation distance is a width of the fulcrum.

4. The method of claim 1, wherein positioning the fulcrum between the first metatarsal and the second metatarsal comprises positioning the fulcrum between a proximal portion of the first metatarsal and a proximal portion of the second metatarsal.

5. The method of claim 4, wherein
positioning the fulcrum between the proximal portion of the first metatarsal and the proximal portion of the second metatarsal comprises positioning the fulcrum between a base of the first metatarsal and a base of the second metatarsal, and
moving the first metatarsal relative to the medial cuneiform comprises moving the first metatarsal without shifting the base of the first metatarsal toward the base of the second metatarsal.

6. The method of claim 4, wherein the proximal portion of the first metatarsal is a proximal-most third of the first metatarsal and the proximal portion of the second metatarsal is a proximal-most third of the second metatarsal.

7. The method of claim 1, wherein moving the first metatarsal relative to the medial cuneiform comprises moving the first metatarsal relative to the medial cuneiform in a frontal plane, and moving the first metatarsal against the fulcrum comprises rotating the first metatarsal against the fulcrum.

8. The method of claim 1, wherein moving the first metatarsal relative to the medial cuneiform comprises moving the first metatarsal relative to the medial cuneiform in a transverse plane, and moving the first metatarsal against the fulcrum comprises pivoting the first metatarsal against the fulcrum.

9. The method of claim 1, wherein moving the first metatarsal relative to the medial cuneiform comprises moving the first metatarsal relative to the medial cuneiform in three planes.

10. The method of claim 1, further comprising:
preparing an end of the first metatarsal; and
preparing an end of the medial cuneiform opposing the end of the first metatarsal.

11. The method of claim 10, wherein:
preparing the end of the first metatarsal comprises preparing the end of the first metatarsal after moving the first metatarsal relative to the medial cuneiform, and
preparing the end of the medial cuneiform comprises preparing the end of the medial cuneiform after moving the first metatarsal relative to the medial cuneiform.

12. The method of claim 10, wherein:
preparing the end of the first metatarsal comprises cutting the end of the first metatarsal; and
preparing the end of the medial cuneiform comprises cutting the end of the medial cuneiform.

13. The method of claim 12, further comprising attaching a bone preparation guide to at least one of the first metatarsal and the medial cuneiform, wherein cutting the end of the first metatarsal comprises cutting the end of first metatarsal using the bone preparation guide, and cutting the end of the medial cuneiform comprises cutting the end of the medial cuneiform using the bone preparation guide.

14. The method of claim 10, further comprising, after preparing the end of the first metatarsal and after preparing the end of the medial cuneiform but prior to fixing the moved position of the first metatarsal, provisionally fixing the moved position of the first metatarsal relative to the medial cuneiform.

15. The method of claim 1, further comprising engaging a bone positioning guide with the first metatarsal, wherein moving the first metatarsal relative to the medial cuneiform comprises moving the first metatarsal with the bone positioning guide.

16. The method of claim 1, wherein the fulcrum has a length extending from a leading end to a trailing end and tapers in thickness along at least a portion of the length from the trailing end to the leading end.

17. The method of claim 1, wherein the fulcrum has a generally rectangular cross-sectional shape or a generally circular cross-sectional shape.

18. The method of claim 1, wherein
the fulcrum has a body and a handle operatively connected to the body,
the handle projects at a non-zero degree angle from the body to define a tissue retraction space between the handle and the body, and
inserting the fulcrum between the first metatarsal and the second metatarsal comprises retracting tissue away from the tarsal-metatarsal joint with the handle.

19. The method of claim 1, wherein inserting the fulcrum between the first metatarsal and the second metatarsal comprises positioning the first metatarsal in contact with a first face of the fulcrum and the second metatarsal in contact with a second face of the fulcrum, the first face having surface features different than the second face.

20. The method of claim 1, wherein the fixation device comprises at least one of a bone plate and an intramedullary implant.

* * * * *